US008541403B2

(12) United States Patent
Chu et al.

(10) Patent No.: US 8,541,403 B2
(45) Date of Patent: Sep. 24, 2013

(54) DIHYDROPYRIDOPHTHALAZINONE INHIBITORS OF POLY(ADP-RIBOSE)POLYMERASE (PARP) FOR USE IN TREATMENT OF DISEASES ASSOCIATED WITH A PTEN DEFICIENCY

(75) Inventors: Daniel Chu, Santa Clara, CA (US); Bing Wang, San Jose, CA (US); Ying Feng, Fremont, CA (US); Yuqiao Shen, Moraga, CA (US); Leonard Edwin Post, Orinda, CA (US)

(73) Assignee: BioMarin Pharmaceutical Inc., Novato, CA (US)

( * ) Notice: Subject to any disclaimer, the term of this patent is extended or adjusted under 35 U.S.C. 154(b) by 56 days.

(21) Appl. No.: 13/020,619

(22) Filed: Feb. 3, 2011

(65) Prior Publication Data
US 2011/0190288 A1    Aug. 4, 2011

Related U.S. Application Data

(60) Provisional application No. 61/301,174, filed on Feb. 3, 2010.

(51) Int. Cl.
| | |
|---|---|
| *A01N 43/00* | (2006.01) |
| *A01N 43/58* | (2006.01) |
| *A01N 43/60* | (2006.01) |
| *A61K 31/55* | (2006.01) |
| *A61K 31/535* | (2006.01) |
| *A61K 31/50* | (2006.01) |
| *A61K 31/495* | (2006.01) |
| *C07D 413/00* | (2006.01) |

(52) U.S. Cl.
USPC .................. 514/210.21; 514/232.8; 514/248; 544/115

(58) Field of Classification Search
None
See application file for complete search history.

(56) References Cited

U.S. PATENT DOCUMENTS

| | | | |
|---|---|---|---|
| 4,526,894 | A | 7/1985 | Enomoto et al. |
| 5,328,905 | A | 7/1994 | Hamminga et al. |
| 6,903,098 | B1 | 6/2005 | Lubisch et al. |
| 7,268,138 | B2 | 9/2007 | Kalish et al. |
| 7,456,178 | B2 | 11/2008 | Kalish et al. |
| 7,601,719 | B2 | 10/2009 | Kalish et al. |
| 7,750,008 | B2 | 7/2010 | Kalish et al. |
| 8,012,976 | B2 * | 9/2011 | Wang et al. .............. 514/250 |
| 2004/0106631 | A1 | 6/2004 | Bernardelli et al. |
| 2006/0004028 | A1 | 1/2006 | Shiromizu et al. |
| 2008/0058325 | A1 | 3/2008 | Kalish et al. |
| 2009/0088407 | A1 | 4/2009 | Kalish et al. |
| 2010/0035883 | A1 | 2/2010 | Wang et al. |
| 2011/0190266 | A1 | 8/2011 | Chu et al. |
| 2011/0196153 | A1 | 8/2011 | Wang et al. |
| 2011/0237581 | A1 | 9/2011 | Wang et al. |
| 2012/0129865 | A1 | 5/2012 | Wang et al. |

FOREIGN PATENT DOCUMENTS

| | | |
|---|---|---|
| DE | 19727410 A1 | 1/1999 |
| EP | 0927718 A1 | 7/1999 |
| EP | 1340819 A1 | 9/2003 |
| JP | 2001-302669 A | 10/2001 |
| JP | 2002-284699 A | 10/2002 |
| WO | 9629327 A1 | 9/1996 |
| WO | WO 99/11645 A1 | 3/1999 |
| WO | WO 99/59975 A1 | 11/1999 |
| WO | 02/098424 A1 | 12/2002 |
| WO | WO 2004/080976 | 3/2004 |
| WO | WO 2004/105700 A1 | 12/2004 |
| WO | WO 2010/017055 A1 | 2/2010 |

(Continued)

OTHER PUBLICATIONS

ISA, PCT International Search Report and Written Opinion of the International Search Authority dated Apr. 2, 2010 for International Patent Application No. PCT/US2009/051879.

(Continued)

*Primary Examiner* — Anna Pagonakis
(74) *Attorney, Agent, or Firm* — Jones Day

(57) ABSTRACT

A compound having the structure set forth in Formula (I) and Formula (II):

Formula (I)

Formula (II)

wherein the substituents Y, Z, A, B, $R_1$, $R_2$, $R_3$, $R_4$ and $R_5$ are as defined herein. Provided herein are inhibitors of poly (ADP-ribose)polymerase activity. Also described herein are pharmaceutical compositions that include at least one compound described herein and the use of a compound or pharmaceutical composition described herein to treat diseases, disorders and conditions associated with a PTEN deficiency that are ameliorated by the inhibition of PARP activity.

38 Claims, 5 Drawing Sheets

(56) References Cited

FOREIGN PATENT DOCUMENTS

| WO | WO 2011/097334 A1 | 8/2011 |
| WO | WO 2011/097602 A1 | 8/2011 |
| WO | WO 2011/130661 A1 | 10/2011 |
| WO | 2012/054698 A1 | 4/2012 |

OTHER PUBLICATIONS

ISA, PCT International Preliminary Report on Patentability dated Feb. 8, 2011 for International Patent Application No. PCT/US2009/051879.

ISA, PCT International Search Report and Written Opinion dated Apr. 21, 2011 for International Patent Application No. PCT/US2011/023532.

ISA, PCT International Search Report and Written Opinion dated Apr. 18, 2011 for International Patent Application No. PCT/US2011/023965.

Karlberg et al., "Crystal Structure of the Catalytic Domain of Human PARP2 in Complex with PARP Inhibitor ABT-888," *Biochemistry* 2010, 49, pp. 1056-1058.

Mendes-Pereira et al., "Synthetic lethal targeting of PTEN mutant cells with PARP inhibitors," *EMBO Mol. Med.* 2009, 1, pp. 315-322.

Thomas, et al., "Preclinical selection of a novel poly(ADP-ribose) polymerase inhibitor for clinical trial," *Mol. Cancer Ther.* 2007, 6(3), pp. 945-956.

United Kingdom Intellectual Property Office, Patents Act 1977 Combined Search and Examination Report under Sections 17 & 18(3) dated Nov. 12, 2009 for application No. GB 0913474.3.

United Kingdom Intellectual Property Office, Patents Act 1977 Examination Report under Section 18(3) dated Sep. 14, 2010 for application No. GB 0913474.3.

Salmena, Leonardo et al., "Tenets of PTEN Tumor Suppression," Cell 133:403-414, (May 2, 2008).

Kurasawa, Yoshinori, et al., "PTEN expression and methylation status in oral squamous cell carcinoma," Oncology Reports, 19:1429-1434, (2008).

Mriouah, Jihane, et al., "Cellular response to cetuximab in PTEN-silenced head and neck squamous cell carcinoma cell line," International Journal of Oncology, 37:1555-1563, (2010).

McEllin, Brian, et al., PTEN Loss Compromises Homologous Recombination Repair in Astrocytes: Implications for Glioblastoma Therapy with Temozolomide or Poly(ADP-Ribose) Polymerase Inhibitors, Cancer Res., 70:5457-5464, (2010).

Cantley, Lewis C., et al., New insights into tumor suppression: PTEN suppresses tumor formation by restraining the phosphoinositide 3-kinase/AKT pathway, Proc. Natl. Acad. Sci., 96:4240-4245, (Apr. 1999).

Aveyard, J.S., et al., "Somatic mutation of PTEN in bladder carcinoma," British Journal of Cancer, 80(5/6):904-908, (1999).

Bruni, Paola, et al., PTEN expression is reduced in a subset of sporadic thyroid carcinomas: evidence that PTEN-growth suppressing activity in thyroid cancer cells is mediated by p27KIP1, Oncogene, 19:3146-3155, (2000).

ISA, PCT International Search Report and Written Opinion dated Nov. 30, 2011 for International Patent Application No. PCT/US2011/057039.

ISA, PCT International Search Report and Written Opinion dated Apr. 27, 2012 for International Patent Application No. PCT/US2011/039045.

Gaymes et al., "Inhibitors of poly ADP-ribose polymerase (PARP) induce apoptosis of myeloid leukemic cells: potential for therapy of myeloid leukemia and myelodysplastic syndromes," Haematologica, 94(5): 638-646, (2009).

Gaymes et al., "Microsatellite Instability (MSI)IN High Risk Myelodysplastic Syndrome (MDS) and Acute Myeloid Leukemia (AML) Cells Promotes Frameshift Mutations in DNA Repair Genes: Indications for PARP Inhibitor Therapy, Blood, 52nd Annual Meeting of American Cancer Society of Hematology (ASH) American Society of Hematology," 116(21): 513, Abstract 1194, (2010).

Ham et al., "Impairment of double-strand breaks repair and aberrant splicing of ARM and MRE11 in leukemia-lymphoma cell lines with microsatellite instability," Cancer Science, 97(3): 226-234, (Mar. 2006).

Stefanska et al., "2,7-Dihydro-3H-pyridazino[5,4,3-kl]acridin-3-one derivatives, novel type of cytotoxic agents active on multidrug-resistant cell lines. Synethesis and biological evaluation," Bioorganic & Medicinal Chemistry, 13(6): 1969-75, (2005).

Merchant, Jr., et al., "Synthesis of Benzoquinolizine Derivatives," Indian Journal of Chemistry, 26B: 471-472, (May 1987).

European Patent Office (EPO), Extended Search Report, dated Feb. 8, 2012, for European Patent Application No. 09805360.6.

ISA, PCT International Search Report and Written Opinion dated Jun. 28, 2011 for International Patent Application No. PCT/US2011/032728.

\* cited by examiner

DIHYDROPYRIDOPHTHALAZINONE INHIBITORS OF POLY(ADP-RIBOSE)POLYMERASE (PARP) FOR USE IN TREATMENT OF DISEASES ASSOCIATED WITH A PTEN DEFICIENCY

CROSS REFERENCE TO RELATED APPLICATIONS

The present application claims the benefit of priority of U.S. Provisional Application No. 61/301,174, filed Feb. 3, 2010, the content of which is hereby incorporated by reference in its entirety.

FIELD OF THE INVENTION

Described herein are compounds, methods of making such compounds, pharmaceutical compositions and medicaments containing such compounds, and methods of using such compounds to modulate the activity of PARP to treat or prevent diseases or conditions associated with a deficiency in the enzyme phosphatase and tensin homolog deleted on chromosome 10 (PTEN).

BACKGROUND OF THE INVENTION

The family of poly(ADP-ribose)polymerases (PARP) includes approximately 18 proteins, which all display a certain level of homology in their catalytic domain but differ in their cellular functions (Ame et al., *BioEssays.*, 26(8), 882-893 (2004)). PARP-1 and PARP-2 are unique members of the family, in that their catalytic activities are stimulated by the occurrence of DNA strand breaks.

PARP has been implicated in the signaling of DNA damage through its ability to recognize and rapidly bind to DNA single or double strand breaks (D'Amours, et al., *Biochem. J.*, 342, 249-268 (1999)). It participates in a variety of DNA-related functions including gene amplification, cell division, differentiation, apoptosis, DNA base excision repair as well as effects on telomere length and chromosome stability (d'Adda di Fagagna, et al., *Nature Gen.*, 23(1), 76-80 (1999)).

Phosphatase and tensin homolog deleted on chromosome 10 (PTEN) is a lipid and protein phosphatase. PTEN functions as a protein phosphatase by dephosphorylating protein substrates on serine, threonine, and tyrosine residues (Myers et al., *Proc Natl Acad Sci USA* 94:9052-9057 (1997)). PTEN functions as a lipid phosphatase by dephosphorylating phosphoinosital 3,4,5-triphosphate (PIP3), a key signaling component of the phosphoinositol-3-kinase (PI3-kinase) pathway (Maehama and Dixon, *J Biol Chem* 273:13375-13378 (1998)).

PTEN is a known tumor suppressor that has been implicated in cellular processes including mediation of the MAP kinase signaling pathway, centromeric maintenance, and is implicated in DNA repair pathways through mediation of Rad51 gene expression. (Gu et al., *J Cell Bio* 143:1375-1383 (1998); Weng et al., *Hum Mol Genet* (2001); and Shen et al., *Cell* 128:157-170 (2007)).

SUMMARY OF THE INVENTION

Provided herein are compounds, compositions and methods for modulating the activity of PARP to treat or prevent diseases or conditions associated with a PTEN deficiency. Among the compounds that are provided herein, are compounds that are inhibitors of PARP. Also described herein is the use of such compounds, compositions and methods for the treatment of diseases, disorders or conditions associated with a PTEN deficiency.

In one aspect is a method of inhibiting poly(ADP-ribose) polymerase (PARP) in a subject having a disease or disorder associated with a PTEN deficiency comprising administering to the subject a therapeutically effective amount of a compound of Formula (I) or Formula (II):

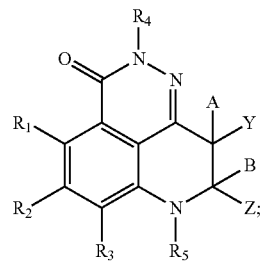

Formula (I)

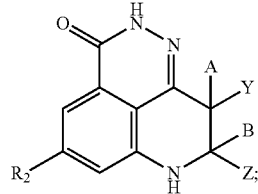

Formula (II)

where $R_1$, $R_2$, $R_3$, $R_4$, $R_5$, A, B, Y, and Z are as defined in the Detailed Description of the Invention.

In still another aspect is a method of treating a disease, disorder or condition associated with a PTEN deficiency which is ameliorated by the inhibition of PARP comprising administering to a subject in need of treatment a therapeutically effective amount of a compound of Formula (I) or Formula (II).

In one aspect is a method of treating a cancer associated with a PTEN deficiency comprising administering to a subject in need of treatment a therapeutically effective amount of a compound of Formula (I) or Formula (II). In certain aspects, the cancer is endometrial carcinoma, glioblastoma (glioblastoma multiforme/anaplastic astrocytoma), prostate cancer, renal cancer, small cell lung carcinoma, meningioma, head and neck cancer, thyroid cancer, bladder cancer, colorectal cancer, breast cancer or melanoma.

In certain other aspects, provided herein are methods of treating a cancer associated with a PTEN deficiency wherein one or more cancer cells have an abrogated or reduced ability to control the phosphoinositide 3-kinase signaling pathway, comprising administering to a subject in need of treatment a therapeutically effective amount of a compound of Formula (I) or Formula (II). In certain embodiments, the cancer comprises one or more cancer cells having a reduced or abrogated ability to control the phosphoinositide 3-kinase signaling pathway for regulation of cell growth relative to normal cells.

In yet another aspect is a method of treating a cancer deficient in Homologous Recombination (HR) dependent DNA double strand break (DSB) repair pathway, comprising administering to a subject in need of treatment a therapeutically effective amount of a compound of Formula (I) or Formula (II). In certain embodiments the cancer comprises one or more cancer cells having a reduced or abrogated ability to repair DNA DSB by FIR relative to normal cells. In one embodiment the cancer cells have a PTEN deficient phenotype. In yet another embodiment the cancer cells are deficient in PTEN. In a further embodiment the subject is heterozygous for a mutation in a gene encoding a component of the HR dependent DNA DSB repair pathway. In yet a further embodiment the subject is heterozygous for a mutation in PTEN. In certain aspects, the cancer is endometrial carcinoma, glioblastoma (glioblastoma multiforme/anaplastic astrocytoma), prostate cancer, renal cancer, small cell lung carcinoma, meningioma, head and neck cancer, thyroid cancer, bladder cancer, colorectal cancer, breast cancer or melanoma.

In another aspect is a method of treating cancer, comprising administering to a subject in need of treatment a therapeutically effective amount of a compound of Formula (I) or Formula (II) in combination with ionizing radiation, one or more chemotherapeutic agents, or a combination thereof.

In one embodiment the compound of Formula (I) or Formula (II) is administered simultaneously with ionizing radiation, one or more chemotherapeutic agents, or a combination thereof. In another embodiment the compound of Formula (I) or Formula (II) is administered sequentially with ionizing radiation, one or more chemotherapeutic agents, or a combination thereof.

In one aspect is the use of a compound of Formula (I) or Formula (II) in the formulation of a medicament for the treatment of a poly(ADP-ribose)polymerase mediated disease or condition associated with a PTEN deficiency.

In another aspect is an article of manufacture, comprising packaging material, a compound of Formula (I) or Formula (II), and a label, wherein the compound is effective for modulating the activity of the enzyme poly(ADP-ribose)polymerase, or for treatment, prevention or amelioration of one or more symptoms of a disease or condition associated with a PTEN deficiency, wherein the compound is packaged within the packaging material, and wherein the label indicates that the compound, or pharmaceutically acceptable salt, pharmaceutically acceptable N-oxide, pharmaceutically active metabolite, pharmaceutically acceptable prodrug, or pharmaceutically acceptable solvate thereof, or a pharmaceutical composition comprising such a compound is used for modulating the activity of poly(ADP-ribose)polymerase, or for treatment, prevention or amelioration of one or more symptoms of a disease or condition associated with a PTEN deficiency.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
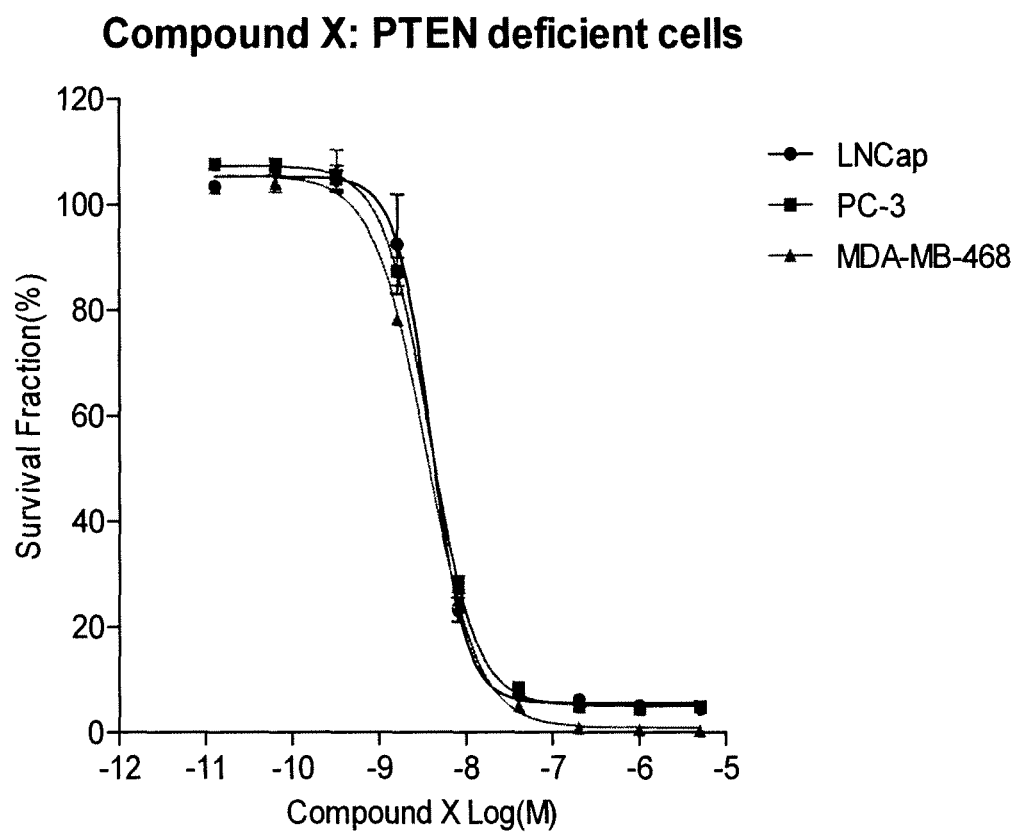
FIG. 1 provides the results of the in vitro cytotoxicity assays performed on PTEN −/− (PTEN deficient) tumor cell lines treated with a PARP inhibitor described herein (Compound X). (-●-) LNCap tumor cell line; (-■-) PC-3 tumor cell line; and (-▲-) MDA-MB-468 tumor cell line.

Provided herein are methods for the treatment of diseases or disorders associated with a PTEN deficiency, including certain cancers, comprising the administration of the poly (ADP-ribose)polymerases (PARP) inhibitors described herein. In some embodiments, the methods presented herein comprise the administration of a PARP inhibitor described herein to a subject in need thereof having a disease or disorder associated with a PTEN deficiency. In some embodiments, the disease or disorder associated with a PTEN deficiency is cancer. In certain embodiments, the disease or disorder associated with a PTEN deficiency is endometrial carcinoma. In certain embodiments, the disease or disorder associated with a PTEN deficiency is glioblastoma. In certain embodiments, the disease or disorder associated with a PTEN deficiency is prostate cancer. In certain embodiments, the disease or disorder associated with a PTEN deficiency is bladder cancer. In certain embodiments, the disease or disorder associated with a PTEN deficiency is breast cancer. In certain embodiments, the disease or disorder associated with PTEN deficiency is colorectal cancer. In certain embodiments, the disease or disorder associated with a PTEN deficiency is melanoma.

Poly(ADP-Ribose)Polymerases (PARP)

The mammalian enzyme PARP-1 is a multidomain protein. PARP-1 is implicated in the signaling of DNA damage through its ability to recognize and rapidly bind to DNA single or double strand breaks. D'Amours, et al., *Biochem. J.*, 342, 249-268 (1999); and Virag et al. *Pharmacological Reviews*, vol. 54, no. 3, 375-429 (2002) are hereby incorporated by reference for such disclosure.

The family of poly(ADP-ribose)polymerases includes approximately 18 proteins, which all display a certain level of homology in their catalytic domain but differ in their cellular functions. PARP-1 and PARP-2 are unique members of the family, in that their catalytic activities are stimulated by the occurrence of DNA strand breaks. Ame et al., *BioEssays* 26(8), 882-893 (2004) is hereby incorporated by reference for such disclosure.

PARP-1 participates in a variety of DNA-related functions including gene amplification, cell division, differentiation, apoptosis, DNA base excision repair as well as effects on telomere length and chromosome stability. d'Adda di Fagagna, et al., *Nature Gen.*, 23(1), 76-80 (1999) is hereby incorporated by reference for such disclosure.

Studies on the mechanism by which PARP-1 modulates DNA repair and other processes identifies its importance in the formation of poly(ADP-ribose) chains within the cellular nucleus. The DNA-bound, activated PARP-1 utilizes NAD+ to synthesize poly(ADP-ribose) on a variety of nuclear target proteins, including topoisomerases, histones and PARP itself. Althaus, F. R. and Richter, C., ADP-Ribosylation of Proteins: Enzymology and Biological Significance, Springer-Verlag, Berlin (1987); and Rhun, et al., *Biochem. Biophys. Res. Commun.*, 245, 1-10 (1998) are hereby incorporated by reference for such disclosure.

Poly(ADP-ribosyl)ation is also associated with malignant transformation. For example, PARP-1 activity is higher in the isolated nuclei of SV40-transformed fibroblasts, while both leukemic cells and colon cancer cells show higher enzyme activity than the equivalent normal leukocytes and colon mucosa. Furthermore, malignant prostate tumors have increased levels of active PARP as compared to benign prostate cells, which is associated with higher levels of genetic instability. Miwa, et al., *Arch. Biochem. Biophys.*, 181, 313-321 (1977); Burzio, et al., *Proc. Soc. Exp. Biol. Med.*, 149, 933-938 (1975); Hirai, et al., *Cancer Res.*, 43, 3441-3446 (1983); and Mcnealy, et al., *Anticancer Res.*, 23, 1473-1478 (2003) are hereby incorporated by reference for such disclosure.

In cells treated with alkylating agents, the inhibition of PARP leads to a marked increase in DNA-strand breakage and cell killing. PARP-1 inhibitors also enhance the effects of radiation response by suppressing the repair of potentially lethal damage. PARP inhibitors are also effective in radiosensitizing hypoxic tumor cells. In certain tumor cell lines, chemical inhibition of PARP activity is also associated with marked sensitization to very low doses of radiation.

Furthermore, PARP-1 knockout (PARP −/−) animals exhibit genomic instability in response to alkylating agents and γ-irradiation. Data indicates that PARP-1 and PARP-2 possess both overlapping and non-redundant functions in the maintenance of genomic stability, making them both interesting targets. Wang, et al., *Genes Dev.*, 9, 509-520 (1995); Menissier de Murcia, et al., *Proc. Natl. Acad. Sci. USA*, 94, 7303-7307 (1997); and Menissier de Murcia, et al., *EMBO. J.*, 22(9), 2255-2263 (2003) are hereby incorporated by reference for such disclosure.

Phosphatase and Tensin Homologue Deleted on Chromosome 10 (PTEN)

There are two major domains of PTEN, the N-terminal phosphatase domain and the C-terminal domain (Lee et al., 1999). While the role of PTEN in tumor suppression has been mostly attributed to its N-terminal lipid phosphatase activity (Cantley and Neel, *Proc Natl Acad Sci USA* 96:4240-4245 (1999)), more than 40% of PTEN tumorigenic mutations occur in the C-terminal domain (Waite and Eng, *Am J. Hum Gen* 70:829-844 (2002)). This fact indicates that PTEN may have additional functions through its C-terminal domain, which is significant in tumor suppression. The C-terminal domain contains both a C2 domain and a tail region that may be related to PTEN stability (Georgescu et al., *Proc Natl Acd Sci USA* 96:10182-10187 (1999)) and protein-protein interaction (Fanning and Anderson, *Curr Opin Cell Biol* 11:432-439 (1999)). The C2 domain is understood to play a role in PTEN stability (Georgescu et al., *Cancer Res* 60:7033-7038 (2000)) and its recruitment to phospholipid membranes (Das et al., *Proc Natl Acd Sci USA* 100:7491-7496 (2003)). Crystal structure analysis of this domain revealed a β-sandwich structure (Lee et al., *Cell* 99:323-334 (1999)), suggesting a basis for its interaction with DNA and other proteins. Additionally, it is known that PTEN uses the C2 domain to interact with the centromere (Shen et al., *Cell* 128:157-170 (2007)).

PTEN Activity

PTEN is a lipid and protein phosphatase. PTEN protein phosphatase can dephosphorylate protein substrates on serine, threonine and tyrosine residues. The lipid phosphatase activity of PTEN is known to act upon the substrate phosphoinositol 3,4,5-triphosphate (PIP3), a key signaling component of the phosphoinositol-3-kinase (PI3-kinase) pathway (Maehama and Dixon, *J Biol Chem* 273:13375-13378 (1998)). The PI3-kinase/Akt pathway is regarded as the primary physiological target of PTEN.

PTEN phosphatase also targets different proteins. Focal adhesion kinase (FAK), a nonreceptor protein tyrosine kinase, has been identified as a direct protein target of PTEN. Similarly, PTEN also reduces the tyrosine phosphorylation of p130Cas, a FAK downstream effector. By targeting and dephosphorylating FAK and p130Cas, PTEN regulates dynamic cell surface interactions and inhibits cell migration and invasion. Additionally, PTEN lipid phosphatase activity is understood to be involved in the inhibition of cell motility and phosphorylation of both Rac1 and Cdc42 (Liliental et al., *Curr Biol* 10:401-404 (2000)). In addition to FAK/p130Cas, Rac1 and Cdc42, PTEN can also regulate cell motility by directly targeting and dephosphorylating Shc kinase, thereby inhibiting the mitogen-activated protein (MAP) kinase signaling pathway.

As an important intracellular signaling pathway, the MAP kinase cascade provides multiple potential targets for PTEN. PTEN can inactivate multiple membrane proximal proteins upstream of MAP kinase such as Ras and IRS-1 (Gu et al., *J Cell Bio* 143:1375-1383 (1998); Weng et al., *Hum Mol Genet* 10:605-616 (2001b)). The prototypical MAP kinase, extracellular signal-regulated kinase, is often affected by PTEN status. The protein phosphatase activity of PTEN is known to inhibit FAK and extracellular signal-regulated kinase and subsequently block the expression and secretion of matrix metalloproteinase-9, which may contribute to the suppression of glioblastoma invasion. PTEN also inhibits phosphorylation of proteins downstream of MAP kinases. One prominent example is ETS-2, a nuclear target of the MAP kinase pathway and a transcription factor whose DNA-binding ability is controlled by phosphorylation. PTEN also regulates phosphorylation of another transcription factor Sp1, likely through its protein phosphatase activity.

In addition to intracellular signaling molecules, receptor tyrosine kinases also can serve as direct protein targets of PTEN. PTEN physically associates with the receptor of platelet-derived growth factor and directly dephosphorylates the receptor, whereas the phosphatase-deficient PTEN mutant (C124S) not only fails to dephosphorylate the platelet-derived growth factor receptor but also acts in a dominant-negative fashion to increase its phosphorylation (Mahimainathan and Choudhury, *J Biol Chem* 279:15258-15268 (2004)).

PTEN and Disease

Genome or chromosome instability is a hallmark of cancers. Tumor suppressors play roles in maintaining genome stability, and loss of function of these tumor suppressors is known to result in genomic instability. Genetic instability represents an inevitable consequence of the loss of tumor suppressors. Indeed, the frequent occurrence of PTEN mutation and genetic instability is found in a large range of PTEN-deficient cancers. Likewise, it is known that several tumor cell lines are PTEN deficient. PTEN-null embryonic stem cells were shown to exhibit DNA repair checkpoint defects in response to ionizing radiation, which results in the accumulation of unrepaired chromosomes with DNA double-strand gaps and breaks. Further mechanistic study revealed that the observed G2 checkpoint defects may result from functional impairment of the checkpoint protein, CHK1, due to lack of PTEN. PTEN deficiency directly elevates AKT kinase activity, which triggers CHK1 phosphorylation. Phosphorylated CHK1 undergoes ubiquitination, which prevents its entry into the nucleus. Sequestering CHK1 in the cytoplasm impairs its normal function in initiating a DNA repair checkpoint. In addition, CHK1 inactivation in PTEN-deficient cells leads to the accumulation of DNA double-strand breaks (Puc and Parsons, *Cell Cycle* 4:927-929 (2005)). Examination of CHK1 localization in a large panel of primary human breast carcinomas indicates an increased cytoplasmic level of CHK1 in tumor cells with lower expression of PTEN and elevated AKT phosphorylation. Furthermore, aneuploidy was frequently observed in both human breast carcinomas with low expression of PTEN and prostatic intraepithelial neoplasia from Pten +/− mice (Puc and Parsons, *Cell Cycle* 4:927-929 (2005)). Such in vitro and in vivo observations indicate that PTEN deficiencies are involved in initiation of an oncogenic signaling process by causing dysfunction of important checkpoint proteins.

Additionally, the role of nuclear PTEN in the maintenance of chromosomal stability has been demonstrated in both mouse and human systems (Shen et al., *Cell* 128:157-170 (2007)). First, PTEN interacts with centromeres and maintains their stability. It is believed that PTEN does so through its C2 domain, as mutant PTEN without this C2 domain loses the capability to interact with centromeres. Second, PTEN may be necessary for DNA repair because loss of PTEN results in a high frequency of double-strand breaks. PTEN affects double-strand breaks through regulation of Rad51, a key component for homologous recombination repair of DNA double-strand breaks. It has also been demonstrated that PTEN physically associates with an integral component of centromeres in the nucleus, disruption of which causes centromere breakage and massive chromosomal aberrations (Shen et al., *Cell* 128:157-170 (2007)).

The cytoplasm has been considered as the primary site for PTEN to elicit its tumor-suppressive function, and the ability of PTEN to block the PI3-kinase pathway through its phosphatase activity has been regarded as the key mechanism by which PTEN suppresses carcinogenesis. Although the cellular distribution of PTEN varies in different tissues, endogenous PTEN in neurons, gliomas and cells of the thyroid, pancreas and skin is found mostly in the nuclear compartment (Yin and Shen, *Oncogene* 27:5443-5453 (2008)). Growing evidence indicate that malignancies may be accompanied by translocation of PTEN from the nucleus to the cytoplasm. The function of nuclear PTEN may deviate from its role in regulating PIP3 at the plasma membrane, but is consistent with an alternative role in controlling genetic stability and involving chromatin function. In addition, high expression levels of nuclear PTEN have recently been associated with cell cycle arrest at the G0/G1 phase (Ginn-Pease and Eng, *Cancer Res* 63:282-286 (2003)), indicating a likely role of nuclear PTEN in cell growth inhibition. Similarly, multiple aspects of the anti-oncogenic function of PTEN, such as regulation of cell growth and migration, are found independent of its phosphatase activity. Indeed, somatic PTEN mutations do occur outside the phosphatase domain, implying that PTEN can function in tumor suppression through additional activities besides antagonism of the PI3-kinase pathway.

Inactivation of PTEN, either by mutations, deletions, or promoter hypermethylation, has been identified in a wide variety of tumors. The most common way to detect PTEN deficiency is by immunohistochemistry (IHC) staining of paraffin-embedded patient tumor sections (Pallares et al., *Modern Pathology* 18:719-727 (2005)). It is also possible to utilize commercial laboratories, such as Quest Diagnostics (Madison, N.J. USA) or Quintiles (Durham, N.C. USA), which provide services to analyze tumor samples by IHC for PTEN. PTEN mutations may also be identified in human tumors samples by examining the PTEN gene by single-strand conformational polymorphism (SSCP) analysis and DNA sequencing (Minaguchi et al., *Cancer Lett.* 210:57-62 (2004)). This method is particularly useful for PTEN-deficient tumors that still make a mutant protein that will show up on IHC. In addition, the expression level of PTEN can be determined using reverse transcription coupled with PCR (RT-PCR) (Mutter et al., *J. Clin. Endocrin. & Metab.* 85:2334-2338, (2000)).

PARP Inhibitors

A PTEN deficiency in certain tumor cells results in homologous recombination defects which sensitize tumor cells to treatment with PARP inhibitors. The present invention is directed to the used of a PARP inhibitor described herein for the treatment of diseases or disorders associated with a PTEN deficiency, including certain cancers. In some embodiments, a PARP inhibitor described herein reduces or inhibits the activity of one or both of PARP1 and/or PARP2. In some embodiments, a PARP inhibitor described herein reduces or inhibits the activity of PARP1 while not affecting the activity of PARP2. In some embodiments, a PARP inhibitor described herein reduces or inhibits the activity of PARP2 while not affecting the activity of PARP1. In some embodiments, a PARP inhibitor described herein is a substantially complete inhibitor of one or more PARPs. As used herein, "substantially complete inhibition" means, for example, >95% inhibition of one or more targeted PARPs. In other embodiments, "substantially complete inhibition" means, for example, >90% inhibition of one or more targeted PARPs. In other embodiments, "substantially complete inhibition" means, for example, >80% inhibition of one or more targeted PARPs. In other embodiments, a PARP inhibitor described herein is a partial inhibitor of one or more PARPs. As used herein, "partial inhibition" means, for example, between about 40% and about 60% inhibition of one or more targeted PARPs. In other embodiments, "partial inhibition" means, for example, between about 50% and about 70% inhibition of one or more targeted PARPs.

In some embodiments, compounds provided herein have the structure of Formula (I) and Formula (II) and pharmaceutically acceptable salts, solvates, esters, acids and prodrugs thereof. In certain embodiments, provided herein are compounds having the structure of Formula (I) and Formula (II) that are inhibitors of the enzyme poly(ADP-ribose)polymerase (PARP).

Described herein are 8-B,Z-2-R$_4$-4-R$_1$-5-R$_2$-6R$_3$-7R$_5$-9-A,Y-8,9-dihydro-2H-pyrido[4,3,2-de]phthalazin-3(7H)-ones, 8-B,Z-5-R$_2$-9-A,Y-8,9-dihydro-2H-pyrido[4,3,2-de] phthalazin-3(7H)-ones, in which A, B, Z, Y, R$_1$, R$_2$, R$_3$, R$_4$ and R$_5$ are further described herein. In certain embodiments, isomers including enantiomers and diastereoisomers, and chemically protected forms of compounds having a structure represented by Formula (I) and Formula (II) are also provided.

Formula (I) is as follows:

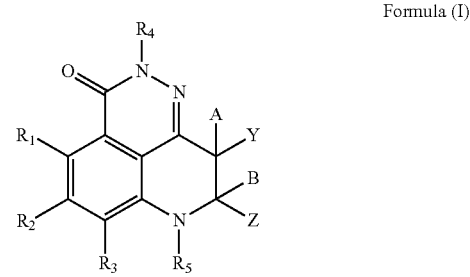

Formula (I)

wherein:
Y and Z are each independently selected from the group consisting of:
  a) an aryl group optionally substituted with 1, 2, or 3 R$_6$;
    wherein each R$_6$ is selected from OH, NO$_2$, CN, Br, Cl, F, I, C$_1$-C$_6$alkyl, C$_3$-C$_8$cycloalkyl, C$_2$-C$_8$heterocycloalkyl; C$_2$-C$_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;

b) a heteroaryl group optionally substituted with 1, 2, or 3 $R_6$;

c) a substituent independently selected from the group consisting of hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl alkylsulfonyl, arylsulfonyl, heteroarylsulfonyl, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene;

$R_1$, $R_2$, and $R_3$ are each independently selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl;

A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl, wherein B is not OH;

$R_A$, and $R_B$ are independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$-alkyl)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, and —S— or $S(O)_q$—, wherein q is 1 or 2 and the 3-10 membered heterocycle ring is optionally substituted with one or more substituents;

$R_4$ and $R_5$ are each independently selected from the group consisting of hydrogen, alkyl, cycloalkyl, alkoxyalkyl, haloalkyl, hydroxyalkylene, and $(NR_AR_B)$alkylene;

and isomers, salts, solvates, chemically protected forms, and prodrugs thereof.

Formula (II) is as follows:

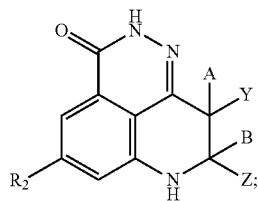

Formula (II)

wherein:

Y is an aryl or heteroaryl group optionally substituted with at least one $R_6$;

Z is an aryl group optionally substituted with at least one $R_6$;

A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl, wherein B is not OH;

$R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;

$R_2$ is selected from hydrogen, Br, Cl, I, or F;

$R_A$, and $R_B$ are independently selected from the group consisting of hydrogen, $C_1$-$C_6$alkyl, $C_3$-$C_8$cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$alkyl)-, —NCO($C_1$-$C_6$-alkyl)-, —NCO ($C_3$-$C_8$cycloalkyl)-, —N(aryl)-, —N(aryl-$C_1$-$C_6$alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$alkyl-)-, and —S— or $S(O)_q$—, wherein q is 1 or 2 and the 3-10 membered heterocycle ring is optionally substituted with one or more substituents; or a pharmaceutically acceptable salt, solvate or prodrug thereof.

In certain embodiments are provided compounds of Formula (I) or a therapeutically acceptable salt thereof wherein $R_1$, $R_2$, $R_3$ are independently selected from a group consisting of hydrogen, alkyl, and halogen; $R_4$ is hydrogen and $R_5$ is selected from the group consisting hydrogen, alkyl, cycloalkyl, alkoxyalkyl, haloalkyl, hydroxyalkylene, and $(NR_AR_B)$alkylene; $R_A$, and $R_B$ are independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$-alkyl)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$—, wherein q is 1 or 2 and the 3-10 membered heterocycle ring is optionally substituted with one or more substituents.

In one embodiment is a compound of Formula (I) wherein Y is an aryl group. In another embodiment the aryl group is a phenyl group. In yet another embodiment the phenyl group is substituted with at least one $R_6$ selected from Br, Cl, F, or I. In one embodiment $R_6$ is F. In one embodiment the phenyl group is substituted with at least one $R_6$ selected from $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In one embodiment $R_6$ is $(NR_AR_B)C_1$-$C_6$alkylene. In another embodiment $C_1$-$C_6$alkyl is selected from methylene, ethylene, n-propylene, iso-propylene, n-butylene, iso-butylene, and tert-butylene. In yet another embodiment $C_1$-$C_6$alkyl is methylene. In yet a further embodiment $R_A$ and $R_B$ are each independently hydrogen, $C_1$-$C_6$alkyl, or $C_3$-$C_8$cycloalkyl. In one embodiment $C_1$-$C_6$alkyl is selected from methyl, ethyl, n-propyl, iso-propyl, n-butyl, iso-butyl, and tert-butyl. In one embodiment $C_1$-$C_6$alkyl is methyl. In another embodiment $C_1$-$C_6$alkyl is ethyl. In yet another embodiment $C_3$-$C_8$cycloalkyl is cyclopropyl, cyclobutyl, cyclopentyl, and cyclohexyl. In a further embodiment $C_3$-$C_8$cycloalkyl is cyclopropyl. In yet a further embodiment $R_6$ is hydroxyalkylene. In one embodiment hydroxyalkylene is selected from $CH_2OH$, $CH_2CH_2OH$, $CH_2CH_2CH_2OH$, $CH(OH)CH_3$, $CH(OH)CH_2CH_3$, $CH_2CH(OH)CH_3$, and $CH_2CH_2CH_2CH_2OH$. In another embodiment $R_A$ and $R_B$ taken together with the nitrogen to which they are attached form a 6 membered heterocycle ring having 1 heteroatom or hetero functionality selected from the group consisting of —O—, —NH, or —N($C_1$-$C_6$alkyl). In yet another embodiment the hetero functionality is —N($C_1$-$C_6$alkyl). In a further embodiment $C_1$-$C_6$alkyl is selected from methyl, ethyl, n-propyl, iso-propyl, n-butyl, iso-butyl, and tert-butyl. In yet a further embodiment $C_1$-$C_6$alkyl is methyl. In one embodiment Y is a heteroaryl group optionally substituted with at least one $R_6$. In another embodiment the heteroaryl group is selected from furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In yet another embodiment the heteroaryl group is imidazole. In a further embodiment imidazole is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl. In one embodiment the heteroaryl group is furan. In another embodiment the heteroaryl group is thiazole. In yet another embodiment the heteroaryl group is 1,3,4-oxadiazole. In a further embodiment heteroaryl group is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl. In one embodiment Z is an aryl group. In another embodiment the aryl group is a phenyl group. In yet another embodiment the phenyl group is substituted with at least one $R_6$ selected from Br, Cl, F, or I. In a further embodiment $R_6$ is F. In yet a further embodiment $R_6$ is Cl. In one embodiment the phenyl group is substituted with at least one $R_6$ selected from $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In another embodiment $R_6$ is $(NR_AR_B)C_1$-$C_6$alkylene. In yet another embodiment $C_1$-$C_6$alkyl is selected from methylene, ethylene, n-propylene, iso-propylene, n-butylene, iso-butylene, and tert-butylene. In yet a further embodiment $C_1$-$C_6$alkyl is methylene. In a further embodiment $R_A$ and $R_B$ are each independently hydrogen, $C_1$-$C_6$alkyl, or $C_3$-$C_8$cycloalkyl. In one embodiment $C_1$-$C_6$alkyl is selected from methyl, ethyl, n-propyl, iso-propyl, n-butyl, iso-butyl, and tert-butyl. In another embodiment $C_1$-$C_6$alkyl is methyl. In yet another embodiment $R_A$ and $R_B$ taken together with the nitrogen to which they are attached form a 6 membered heterocycle ring having 1 heteroatom or hetero functionality selected from the group consisting of —O—, —NH, or —N($C_1$-$C_6$alkyl). In a further embodiment the hetero functionality is —N($C_1$-$C_6$alkyl). In yet another embodiment $C_1$-$C_6$alkyl is selected from methyl, ethyl, n-propyl, iso-propyl, n-butyl, iso-butyl, and tert-butyl. In yet a further embodiment $C_1$-$C_6$alkyl is methyl. In one embodiment Z is a heteroaryl group optionally substituted with at least one $R_6$. In another embodiment the heteroaryl group is selected from furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In yet another embodiment the heteroaryl group is imidazole. In a further embodiment imidazole is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl. In one embodiment the heteroaryl group is furan. In another embodiment the heteroaryl group is thiazole. In yet another embodiment the heteroaryl group is 1,3,4-oxadiazole. In a further embodiment heteroaryl group is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl. In another embodiment $R_2$ is hydrogen. In yet another embodiment $R_2$ is selected from F, Cl, Br, and I. In a further embodiment $R_2$ is F.

In one embodiment is a compound of Formula (I) wherein A is hydrogen. In another embodiment A is $C_1$-$C_6$alkyl. In a further embodiment, A is selected from methyl, ethyl, n-propyl, iso-propyl, n-butyl, iso-butyl, tert-butyl, n-pentyl, and n-hexyl. In yet another embodiment, methyl, ethyl, n-propyl, iso-propyl, n-butyl, iso-butyl, tert-butyl, n-pentyl, and n-hexyl are optionally substituted with OH, $NO_2$, CN, Br, Cl, F, and I. In a further embodiment A is methyl. In yet another embodiment, A is selected from F, Cl, Br, and I. In another embodiment, A is $C_3$-$C_8$cycloalkyl. In another embodiment, A is cyclopropyl, cyclobutyl, cyclopentyl, or cyclohexyl. In one embodiment, A is substituted with OH, $NO_2$, or CN. In a further embodiment, B is $C_1$-$C_6$alkyl. In a further embodiment, B is selected from methyl, ethyl, n-propyl, iso-propyl, n-butyl, iso-butyl, tert-butyl, n-pentyl, and n-hexyl. In yet another embodiment, methyl, ethyl, n-propyl, iso-propyl, n-butyl, iso-butyl, tert-butyl, n-pentyl, and n-hexyl are optionally substituted with OH, $NO_2$, CN, Br, Cl, F, and I. In one embodiment is a compound of Formula (I) wherein B is hydrogen. In a further embodiment B is methyl. In yet another embodiment, B is selected from F, Cl, Br, and I. In another embodiment, B is $C_3$-$C_8$cycloalkyl. In another embodiment, B is cyclopropyl, cyclobutyl, cyclopentyl, or cyclohexyl. In one embodiment, A is substituted with OH, $NO_2$, or CN. In a further embodiment, is a compound of Formula (I) wherein A is hydrogen and B is selected from Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl. In another embodiment, is a compound of Formula (I) wherein B is hydrogen and A is selected from Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl. In yet another embodiment, both A and B are hydrogen. In a further embodiment, both A and B are selected from Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl.

In one embodiment is a compound of Formula (II) wherein Y is an aryl group. In another embodiment the aryl group is a phenyl group. In yet another embodiment the phenyl group is substituted with at least one $R_6$ selected from Br, Cl, F, or I. In one embodiment $R_6$ is F. In one embodiment the phenyl group is substituted with at least one $R_6$ selected from $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In one embodiment $R_6$ is $(NR_AR_B)C_1$-$C_6$alkylene. In another embodiment $C_1$-$C_6$alkyl is selected from methylene, ethylene, n-propylene, iso-propylene, n-butylene, iso-butylene, and tert-butylene. In yet another embodiment $C_1$-$C_6$alkylene is methylene. In yet a further embodiment $R_A$ and $R_B$ are each independently hydrogen, $C_1$-$C_6$alkyl, or $C_3$-$C_8$cycloalkyl. In one embodiment $C_1$-$C_6$alkyl is selected from methyl, ethyl, n-propyl, iso-propyl, n-butyl, iso-butyl, and tert-butyl. In one embodiment $C_1$-$C_6$alkyl is methyl. In another embodiment $C_1$-$C_6$alkyl is ethyl. In yet another embodiment $C_3$-$C_8$cycloalkyl is cyclopropyl, cyclobutyl, cyclopentyl, and cyclohexyl. In a further embodiment $C_3$-$C_8$cycloalkyl is cyclopropyl. In yet a further embodiment $R_6$ is hydroxyalkylene. In one embodiment hydroxyalkylene is selected from $CH_2OH$, $CH_2CH_2OH$, $CH_2CH_2CH_2OH$, $CH(OH)CH_3$, $CH(OH)CH_2CH_3$, $CH_2CH(OH)CH_3$, and $CH_2CH_2CH_2CH_2OH$. In another embodiment $R_A$ and $R_B$ taken together with the nitrogen to which they are attached form a 6 membered heterocycle ring having 1 heteroatom or hetero functionality selected from the group consisting of —O—, —NH, or —N($C_1$-$C_6$alkyl). In yet another embodiment the hetero functionality is —N($C_1$-$C_6$alkyl). In a further embodiment $C_1$-$C_6$alkyl is selected from methyl, ethyl, n-propyl, iso-propyl, n-butyl, iso-butyl, and tert-butyl. In yet a further embodiment $C_1$-$C_6$alkyl is methyl. In one embodiment Y is a heteroaryl group optionally substituted with at least one $R_6$. In another embodiment the heteroaryl group is selected from furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In yet another embodiment the heteroaryl group is imidazole. In a further embodiment imidazole is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl. In one embodiment the heteroaryl group is furan. In another embodiment the heteroaryl group is thiazole. In yet another embodiment the heteroaryl group is 1,3,4-oxadiazole. In a further embodiment heteroaryl group is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl. In one embodiment Z is an aryl group. In another embodiment the aryl group is a phenyl group. In yet another embodiment the phenyl group is substituted with at least one $R_6$ selected from Br, Cl, F, or I. In a further embodiment $R_6$ is F. In yet a further embodiment $R_6$ is Cl. In one embodiment the phenyl group is substituted with at least one $R_6$ selected from $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In another embodiment $R_6$ is $(NR_AR_B)C_1$-$C_6$alkylene. In yet another embodiment $C_1$-$C_6$alkylene is selected from methylene, ethylene, n-propylene, iso-propylene, n-butylene, iso-butylene, and tert-butylene. In yet a further embodiment $C_1$-$C_6$alkyl is methylene. In a further embodiment $R_A$ and $R_B$ are each independently hydrogen, $C_1$-$C_6$alkyl, or $C_3$-$C_8$cycloalkyl. In one embodiment $C_1$-$C_6$alkyl is selected from methyl, ethyl, n-propyl, iso-propyl, n-butyl, iso-butyl, and tert-butyl. In another embodiment $C_1$-$C_6$alkyl is methyl. In yet another embodiment $R_A$ and $R_B$ taken together with the nitrogen to which they are attached form a 6 membered heterocycle ring having 1 heteroatom or hetero functionality selected from the group consisting of —O—, —NH, or —N($C_1$-$C_6$alkyl). In a further embodiment the hetero functionality is —N($C_1$-$C_6$alkyl). In one embodiment $C_1$-$C_6$alkyl is selected from methyl, ethyl, n-propyl, iso-propyl, n-butyl, iso-butyl, and tert-butyl. In yet a further embodiment $C_1$-$C_6$alkyl is methyl.

In another embodiment $R_2$ is hydrogen. In yet another embodiment $R_2$ is selected from F, Cl, Br, and I. In a further embodiment $R_2$ is F.

In one embodiment is a compound of Formula (II) wherein A is hydrogen. In another embodiment A is $C_1$-$C_6$alkyl. In a further embodiment, A is selected from methyl, ethyl, n-propyl, iso-propyl, n-butyl, iso-butyl, tert-butyl, n-pentyl, and n-hexyl. In yet another embodiment, methyl, ethyl, n-propyl, iso-propyl, n-butyl, iso-butyl, tert-butyl, n-pentyl, and n-hexyl are optionally substituted with OH, $NO_2$, CN, Br, Cl, F, and I. In a further embodiment A is methyl. In yet another embodiment, A is selected from F, Cl, Br, and I. In another embodiment, A is $C_3$-$C_8$cycloalkyl. In another embodiment, A is cyclopropyl, cyclobutyl, cyclopentyl, or cyclohexyl. In one embodiment, A is substituted with OH, $NO_2$, or CN. In one embodiment is a compound of Formula (II) wherein B is hydrogen. In a further embodiment, B is $C_1$-$C_6$alkyl. In a further embodiment, B is selected from methyl, ethyl, n-propyl, iso-propyl, n-butyl, iso-butyl, tert-butyl, n-pentyl, and n-hexyl. In yet another embodiment, methyl, ethyl, n-propyl, iso-propyl, n-butyl, iso-butyl, tert-butyl, n-pentyl, and n-hexyl are optionally substituted with OH, $NO_2$, CN, Br, Cl, F, and I. In a further embodiment B is methyl. In yet another embodiment, B is selected from F, Cl, Br, and I. In another embodiment, B is $C_3$-$C_8$cycloalkyl. In another embodiment, B is cyclopropyl, cyclobutyl, cyclopentyl, or cyclohexyl. In one embodiment, A is substituted with OH, $NO_2$, or CN. In a further embodiment, is a compound of Formula (II) wherein A is hydrogen and B is selected from Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl. In another embodiment, is a compound of Formula (II) wherein B is hydrogen and A is selected from Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl. In yet another embodiment, both A and B are hydrogen. In a further embodiment, both A and B are selected from Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl.

In yet a further aspect is a compound selected from:

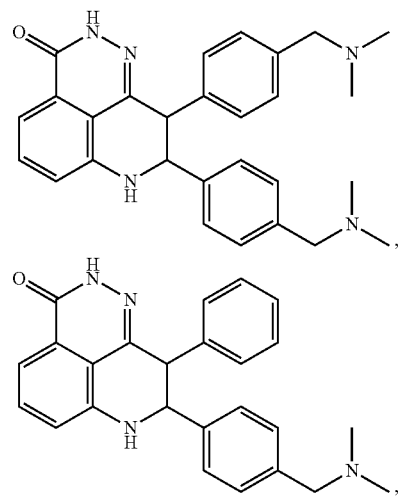

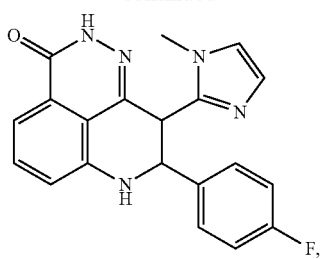
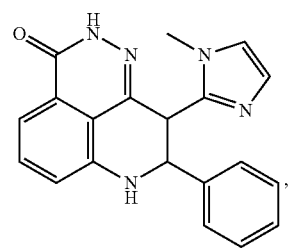
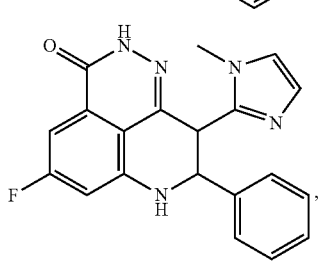
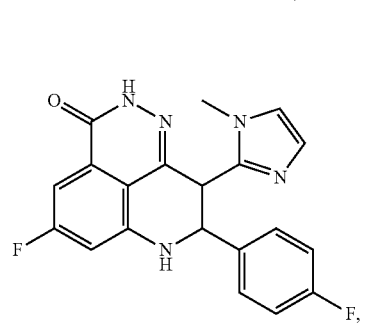
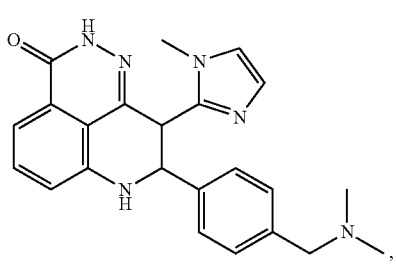
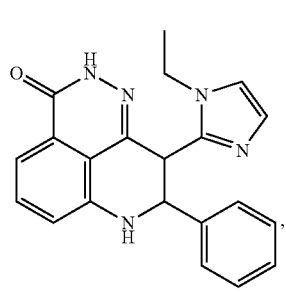
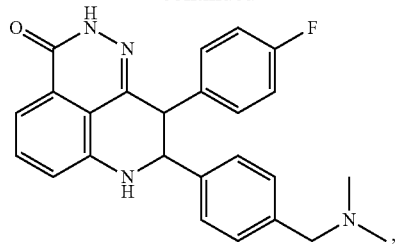
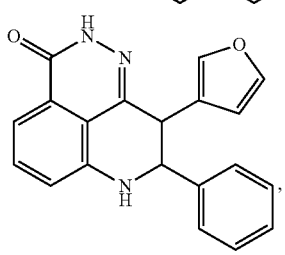
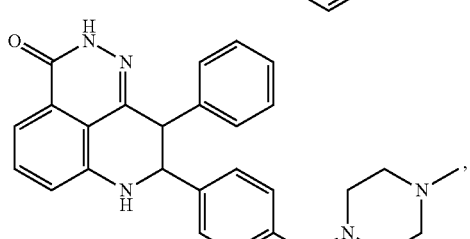
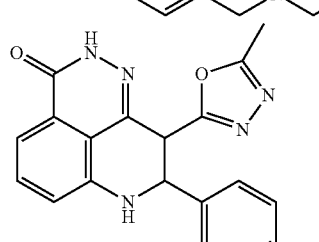
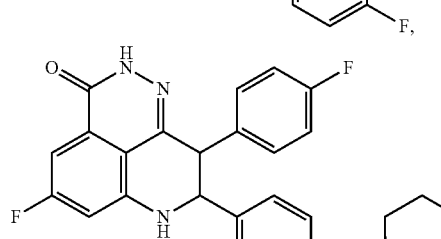
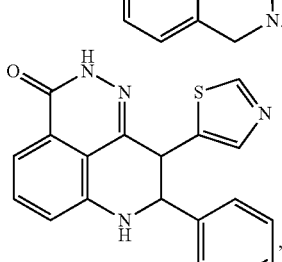
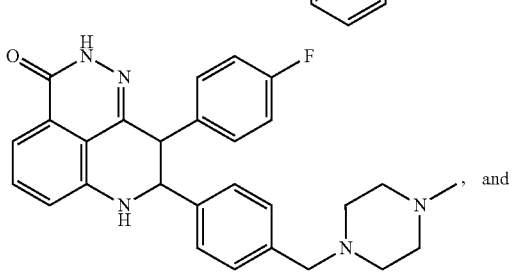

or a pharmaceutically acceptable salt, solvate or prodrug thereof.

In yet another aspect is a compound selected from:

-continued
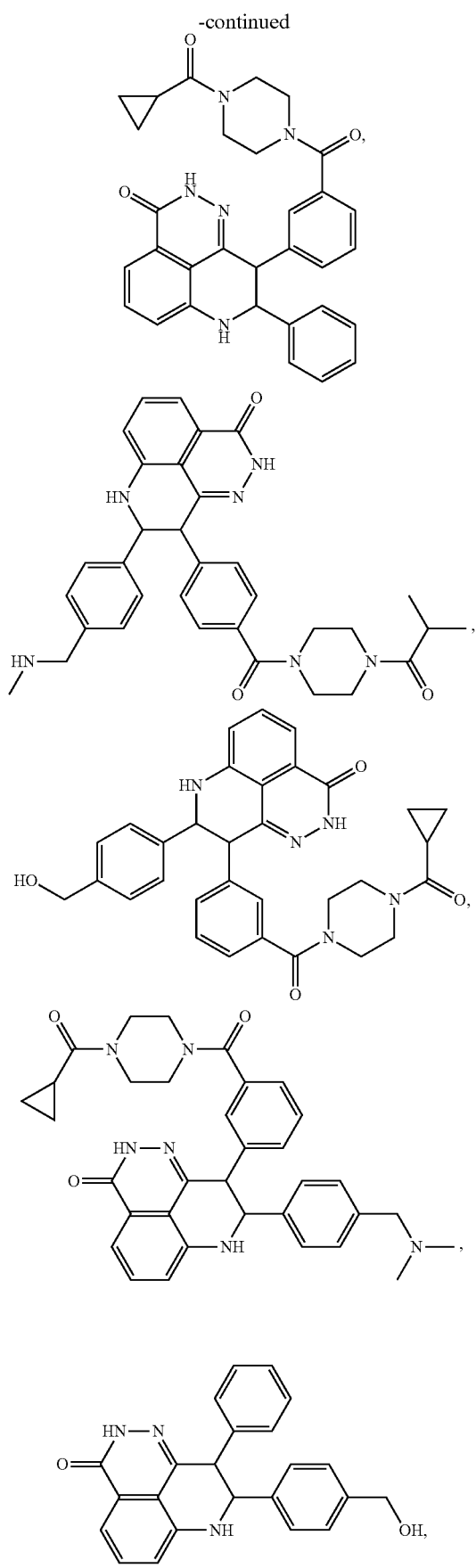
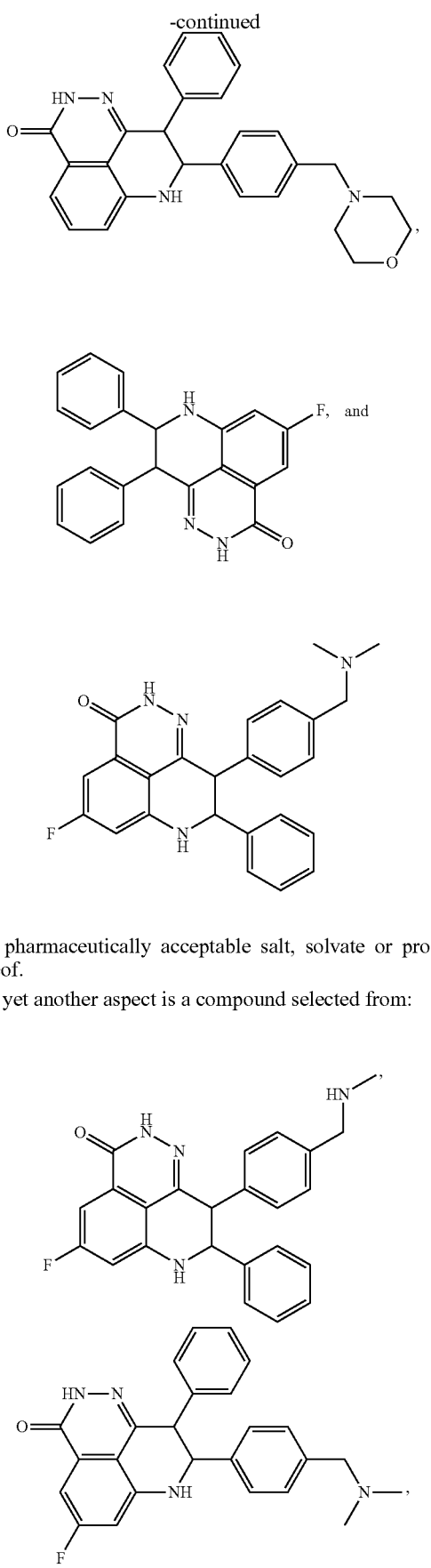
or a pharmaceutically acceptable salt, solvate or prodrug thereof.
In yet another aspect is a compound selected from:

-continued
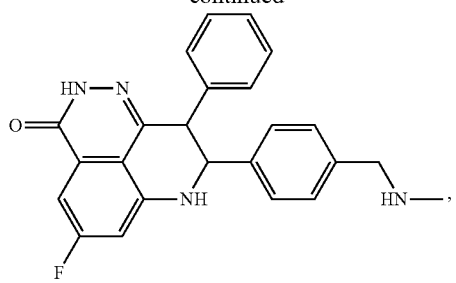
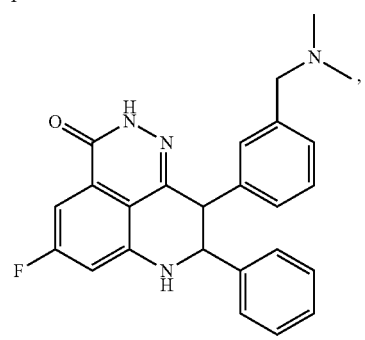
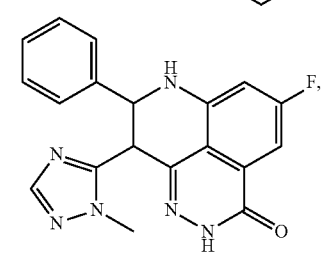
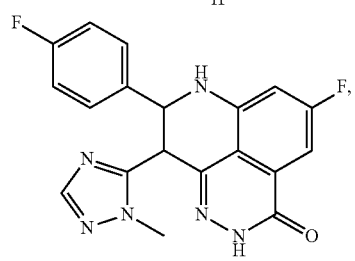
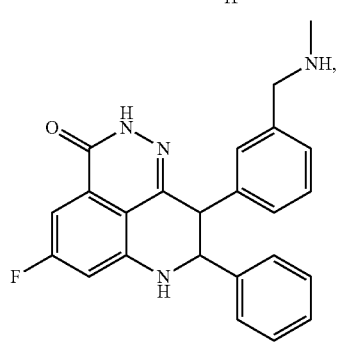
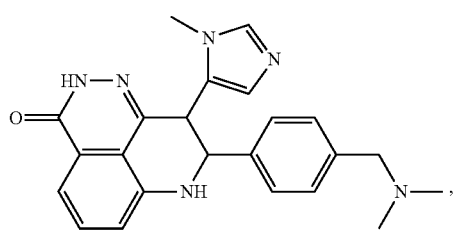
-continued
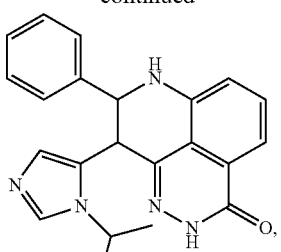
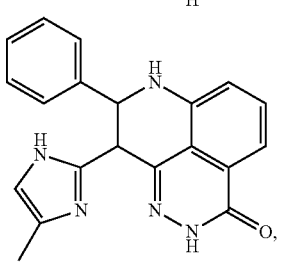
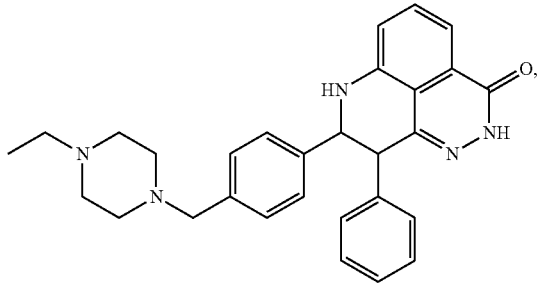
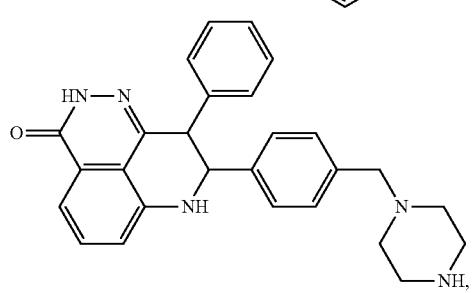

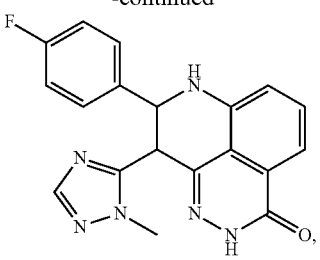
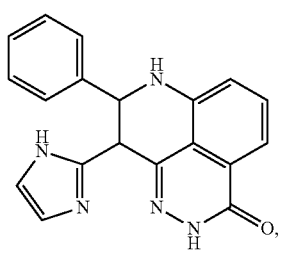
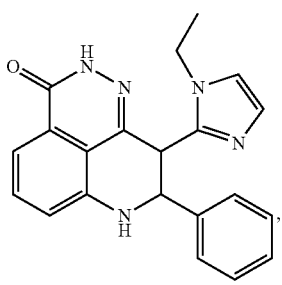
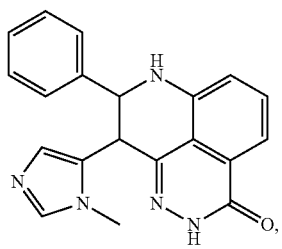
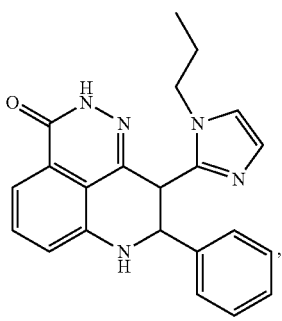
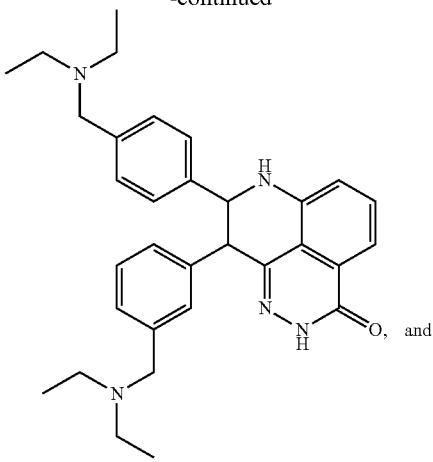
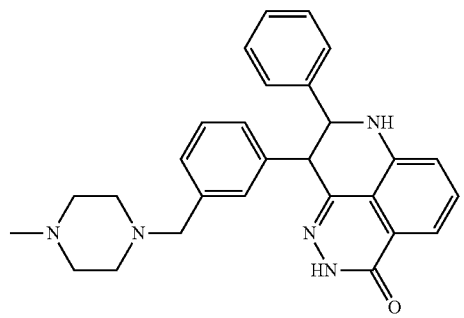
or a pharmaceutically acceptable salt, solvate or prodrug thereof.
In yet a further embodiment is a compound selected from:
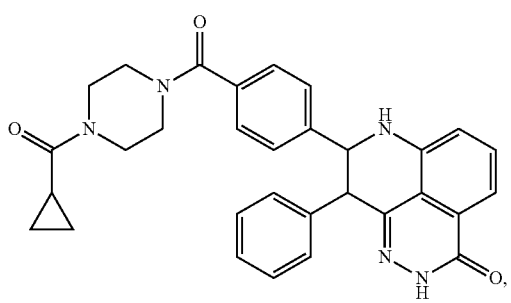
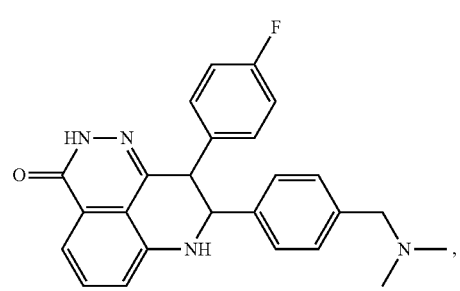

-continued

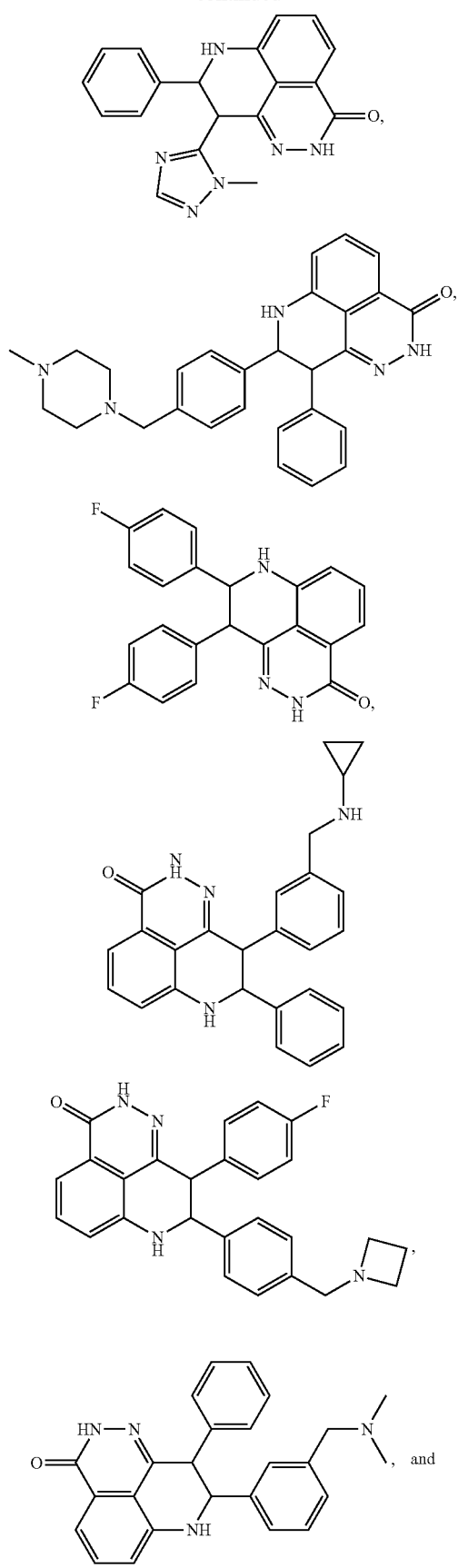

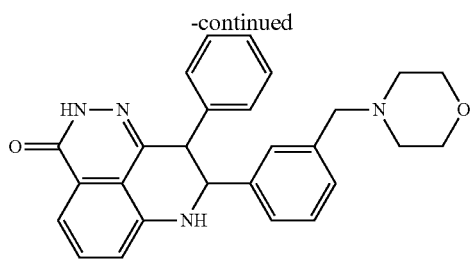

or a pharmaceutically acceptable salt, solvate or prodrug thereof.

In yet a further embodiment is a compound selected from:

(8S,9R)-5-fluoro-9-(1-methyl-1H-imidazol-2-yl)-8-phenyl-8,9-dihydro-2H-pyrido[4,3,2-de]phthalazin-3(7H)-one, (8R,9S)-5-fluoro-9-(1-methyl-1H-imidazol-2-yl)-8-phenyl-8,9-dihydro-2H-pyrido[4,3,2-de]phthalazin-3(7H)-one, (8S,9R)-5-fluoro-8-(4-fluorophenyl)-9-(1-methyl-1H-imidazol-2-yl)-8,9-dihydro-2H-pyrido[4,3,2-de]phthalazin-3(7H)-one, (8R,9S)-5-fluoro-8-(4-fluorophenyl)-9-(1-methyl-1H-imidazol-2-yl)-8,9-dihydro-2H-pyrido[4,3,2-de]phthalazin-3(7H)-one, (8S,9R)-8-(4-fluorophenyl)-9-(1-methyl-1H-imidazol-2-yl)-8,9-dihydro-2H-pyrido[4,3,2-de]phthalazin-3(7H)-one, (8R,9S)-8-(4-fluorophenyl)-9-(1-methyl-1H-imidazol-2-yl)-8,9-dihydro-2H-pyrido[4,3,2-de]phthalazin-3(7H)-one, (8S,9R)-5-fluoro-9-(1-methyl-1H-1,2,4-triazol-5-yl)-8-phenyl-8,9-dihydro-2H-pyrido[4,3,2-de]phthalazin-3(7H)-one, (8R,9S)-5-fluoro-9-(1-methyl-1H-1,2,4-triazol-5-yl)-8-phenyl-8,9-dihydro-2H-pyrido[4,3,2-de]phthalazin-3(7H)-one, (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one, (8R,9S)-5-fluoro-8-(4-fluorophenyl)-9-(1-methyl-1H-1,2,4-triazol-5-yl)-8,9-dihydro-2H-pyrido[4,3,2-de]phthalazin-3(7H)-one, (8S,9R)-8-(4-fluorophenyl)-9-(1-methyl-1H-1,2,4-triazol-5-yl)-8,9-dihydro-2H-pyrido[4,3,2-de]phthalazin-3(7H)-one, (8R,9S)-8-(4-fluorophenyl)-9-(1-methyl-1H-1,2,4-triazol-5-yl)-8,9-dihydro-2H-pyrido[4,3,2-de]phthalazin-3(7H)-one, (8S,9R)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one, and (8R,9S)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one, or a pharmaceutically acceptable salt, solvate or prodrug thereof.

In another aspect is a pharmaceutical composition comprising a compound of Formula (I) or Formula (II) or a pharmaceutically acceptable salt, pharmaceutically acceptable solvate, or pharmaceutically acceptable prodrug and a pharmaceutically acceptable carrier, excipient, binder or diluent thereof.

In certain embodiments are provided PARP inhibitor compounds of Formula (I)

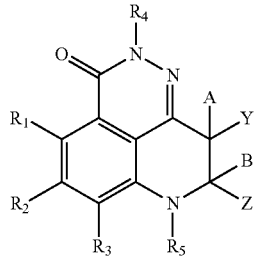

Formula (I)

or a therapeutically acceptable salt thereof wherein $R_1$, $R_2$, and $R_3$ are each independently selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl;

$R_A$, and $R_B$ are independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$-alkyl)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$—, wherein q is 1 or 2 and the 3-10 membered heterocycle ring is optionally substituted with one or more substituents; $R_4$ and $R_5$ are each independently selected from the group consisting of hydrogen, alkyl, cycloalkyl, alkoxyalkyl, haloalkyl, hydroxyalkylene, and $(NR_AR_B)$alkylene;

A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl, wherein B is not OH;

Y and Z are each independently selected from the group consisting of:
a) an aryl group optionally substituted with 1, 2, or 3 substituents $R_6$; $R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;
b) a heteroaryl group optionally substituted with 1, 2, or 3 substituents $R_6$; $R_6$ is previously as defined;
c) a substituent independently selected from the group consisting of hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl alkylsulfonyl, arylsulfonyl, heteroarylsulfonyl, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene; or a pharmaceutically acceptable salt, solvate or prodrug thereof.

In certain embodiments are provided PARP inhibitor compounds of Formula (I) or a therapeutically acceptable salt thereof wherein $R_1$, $R_2$, $R_3$ are independently selected from a group consisting of hydrogen, alkyl, and halogen; $R_1$ is hydrogen and $R_5$ is selected from the group consisting hydrogen, alkyl, cycloalkyl, alkoxyalkyl, haloalkyl, hydroxyalkylene, and $(NR_AR_B)$alkylene; $R_A$, and $R_B$ are independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$-alkyl)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$—, wherein q is 1 or 2 and the 3-10 membered heterocycle ring is optionally substituted with one or more substituents; A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl, wherein B is not OH; Y and Z are each independently selected from the group consisting of:
a) an aryl group optionally substituted with 1, 2, or 3 $R_6$; wherein each $R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;
b) a heteroaryl group optionally substituted with 1, 2, or 3 $R_6$;
c) a substituent independently selected from the group consisting of hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl alkylsulfonyl, arylsulfonyl, heteroarylsulfonyl, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene; or a pharmaceutically acceptable salt, solvate or prodrug thereof.

In certain embodiments are provided PARP inhibitor compounds of Formula (I) or a therapeutically acceptable salt thereof wherein $R_1$, $R_2$, and $R_3$ are independently selected from a group consisting of hydrogen, alkyl, and halogen; $R_4$ and $R_5$ are hydrogen; $R_A$ and $R_B$ are independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$-alkyl)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$—, wherein q is 1 or 2 and the 3-10 membered heterocycle ring is optionally substituted with one or more substituents; A and B are each independently selected from hydrogen, Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl; Y and Z are each independently selected from the group consisting of:

a) an aryl group optionally substituted with 1, 2, or 3 $R_6$; wherein each $R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;

b) a heteroaryl group optionally substituted with 1, 2, or 3 $R_6$;

c) a substituent independently selected from the group consisting of hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl alkylsulfonyl, arylsulfonyl, heteroarylsulfonyl, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene; or a pharmaceutically acceptable salt, solvate or prodrug thereof.

In certain embodiments are provided PARP inhibitor compounds of Formula (I) or a therapeutically acceptable salt thereof wherein $R_1$, $R_2$, $R_3$, $R_4$ and $R_5$ are hydrogen; $R_A$ and $R_B$ are independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$-alkyl)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$—, wherein q is 1 or 2 and the 3-10 membered heterocycle ring is optionally substituted with one or more substituents; A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl, wherein B is not OH; Y and Z are each independently selected from the group consisting of:

a) an aryl group optionally substituted with 1, 2, or 3 $R_6$; wherein each $R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;

b) a heteroaryl group optionally substituted with 1, 2, or 3 $R_6$;

c) a substituent independently selected from the group consisting of hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl alkylsulfonyl, arylsulfonyl, heteroarylsulfonyl, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene; or a pharmaceutically acceptable salt, solvate or prodrug thereof.

In one embodiment is a PARP inhibitor compound of Formula (I) wherein $R_1$, $R_2$, $R_3$ are each independently selected from a group consisting of hydrogen, alkyl, and halogen; $R_4$ is hydrogen and $R_5$ is selected from the group consisting hydrogen, alkyl, cycloalkyl, alkoxyalkyl, haloalkyl, hydroxyalkylene, and $(NR_AR_B)$alkylene; and isomers, salts, solvates, chemically protected forms, and prodrugs thereof.

In another embodiment is a PARP inhibitor compound of Formula (I) wherein $R_1$, $R_2$, $R_3$ are each independently selected from a group consisting of hydrogen, alkyl, and halogen; $R_4$ and $R_5$ are hydrogen; and isomers, salts, solvates, chemically protected forms, and prodrugs thereof.

In a further embodiment is a compound of PARP inhibitor Formula (I) wherein $R_1$, $R_2$, $R_3$, $R_4$ are each hydrogen and $R_5$ is alkyl.

In yet another embodiment is a PARP inhibitor compound of Formula (I) wherein $R_1$, $R_2$, $R_3$, $R_4$ are each hydrogen; and $R_5$ is methyl.

In one embodiment is a PARP inhibitor compound of Formula (I) wherein $R_1$, $R_2$, and $R_3$ are each hydrogen.

In another embodiment is a PARP inhibitor compound of Formula (I) wherein Y and Z are each independently selected from the group consisting of a) a phenyl group optionally substituted with 1, 2, or 3 $R_6$;

b) a pyridyl group optionally substituted with 1, 2, or 3 $R_6$; and c) a substituent independently selected from the group consisting of hydrogen, alkoxyalkyl, alkoxycarbonylalkyl, alkyl, arylalkyl, cycloalkyl, cycloalkylalkyl, haloalkyl, oxo, heterocycloalkyl, heterocycloalkylalkyl, alkylcarbonyl, arylcarbonyl, heteroarylcarbonyl, $(NR_AR_B)$alkylene, $(NR_AR_B)$carbonyl, and $(NR_AR_B)$carbonylalkylene.

In a further embodiment is a PARP inhibitor compound of Formula (I) wherein Y and Z are each independently selected from the group consisting of a) a phenyl group optionally substituted with 1, 2, or 3 $R_6$;

b) a imidazole group optionally substituted with 1, 2, or 3 $R_6$; and c) a substituent independently selected from the group consisting of hydrogen, alkoxyalkyl, alkoxycarbonylalkyl, alkyl, arylalkyl, cycloalkyl, cycloalkylalkyl, haloalkyl, oxo, heterocycloalkyl, heterocycloalkylalkyl, alkylcarbonyl, arylcarbonyl, heteroarylcarbonyl, $(NR_AR_B)$alkylene $(NR_AR_B)$carbonyl, and $(NR_AR_B)$carbonylalkylene.

In a further embodiment is a PARP inhibitor compound of Formula (I) wherein Y and Z are each independently selected from the group consisting of d) a phenyl group optionally substituted with 1, 2, or 3 $R_6$;
e) a triazole group optionally substituted with 1, 2, or 3 $R_6$; and
f) a substituent independently selected from the group consisting of hydrogen, alkoxyalkyl, alkoxycarbonylalkyl, alkyl, arylalkyl, cycloalkyl, cycloalkylalkyl, haloalkyl, oxo, heterocycloalkyl, heterocycloalkylalkyl, alkylcarbonyl, arylcarbonyl, heteroarylcarbonyl, $(NR_AR_B)$alkylene $(NR_AR_B)$carbonyl, and $(NR_AR_B)$carbonylalkylene.

In one embodiment is a PARP inhibitor compound of Formula (I) wherein $R_5$ is hydrogen or an alkyl group. In another embodiment, $R_5$ is hydrogen. In a further embodiment, $R_5$ is $C_1$-$C_6$ alkyl. In yet a further embodiment, $R_5$ is $CH_3$. In another embodiment, $R_5$ is $CH_2CH_3$.

In another embodiment is a PARP inhibitor compound of Formula (I) wherein $R_4$ is hydrogen or an alkyl group. In yet another embodiment, $R_4$ is hydrogen.

In one embodiment, $R_2$ is selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl. In a further embodiment $R_2$ is a halogen selected from F, Cl, Br, and I. In yet a further embodiment, $R_2$ is fluorine. In one embodiment, $R_2$ is hydrogen.

In another embodiment, $R_3$ is selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl. In a further embodiment, $R_3$ is hydrogen. In some embodiments, $R_1$ is selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl. In a further embodiment, $R_1$ is hydrogen.

Also disclosed herein are PARP inhibitor compounds of Formula (I) wherein Z is an aryl group optionally substituted with 1, 2, or 3 $R_6$; wherein each $R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_r$ $C_6$alkylene, $(NR_AR_B)$carbonyl, $(NR_AR_B)$carbonylalkylene, $(NR_AR_B)$sulfonyl, and $(NR_AR_B)$sulfonylalkylene. In one embodiment is a compound of Formula (I) wherein Z is an optionally substituted phenyl group. In one embodiment, Z is a phenyl group. In another embodiment, the phenyl group is optionally substituted with at least one $R_6$ selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In another embodiment, $R_6$ is $(NR_AR_B)$alkylene. In a further embodiment, $R_6$ is $CH_2(NR_AR_B)$. In a further embodiment, $R_6$ is $CH_2(NR_AR_B)$ wherein $NR_AR_B$ is azetidine, pyrrolidine, piperidine or morpholine. In yet a further embodiment, $R_A$ is H or alkyl. In another embodiment, $R_A$ is $C_1$-$C_6$alkyl. In yet another embodiment, $R_A$ is $CH_3$. In another embodiment, $R_B$ is H or alkyl. In one embodiment, $R_B$ is $C_1$-$C_6$alkyl. In yet another embodiment, $R_B$ is $CH_3$. In a further embodiment, $R_6$ is $CH_2NHCH_3$. In yet a further embodiment, $R_6$ is $CH_2NCH_3CH_3$. In one embodiment, $R_6$ is (C=O)heterocycloalkyl(C=O)alkyl. In one embodiment $R_6$ is (C=O)heterocycloalkyl(C=O)alkyl wherein the heterocycloalkyl group has at least one heteroatom selected from O, N, and S. In another embodiment, the heterocycloalkyl group has two N atoms. In a further embodiment, $R_6$ is (C=O)heterocycloalkyl(C=O)alkyl wherein alkyl is selected from methyl, ethyl, n-propyl, iso-propyl, cyclopropyl, n-butyl, iso-butyl, and t-butyl.

In one embodiment, the alkyl group is cyclopropyl. In another embodiment, the alkyl group is iso-propyl. In one embodiment, $R_6$ is

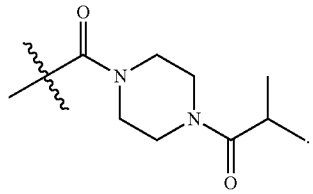 [SMILES: *C(=O)N1CCN(C(=O)C(C)C)CC1]

In another embodiment, $R_6$ is

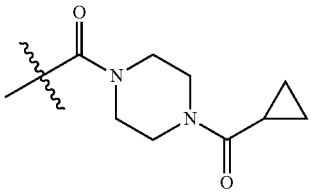

Presented herein are PARP inhibitor compounds of Formula (I) wherein Z is an optionally substituted heteroaryl group. In one embodiment, the heteroaryl group is selected from pyridine, pyrimidine, pyrazine, pyrazole, oxazole, thiazole, isoxazole, isothiazole, 1,3,4-oxadiazole, pyridazine, 1,3,5-trazine, 1,2,4-triazine, quinoxaline, benzimidazole, benzotriazole, purine, 1H-[1,2,3]triazolo[4,5-d]pyrimidine, triazole, imidazole, thiophene, furan, isobenzofuran, pyrrole, indolizine, isoindole, indole, indazole, isoquinoline, quinoline, phthalazine, naphthyridine, quinazoline, cinnoline, and pteridine. In one embodiment, Z is pyridine. In another embodiment, Z is optionally substituted pyridine.

Also disclosed herein are PARP inhibitor compounds of Formula (I) wherein Y is an aryl group optionally substituted with 1, 2, or 3 $R_6$; wherein each $R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$ carbonyl, $(NR_AR_B)$carbonylalkylene, $(NR_AR_B)$sulfonyl, and $(NR_AR_B)$sulfonylalkylene. In one embodiment is a compound of Formula (I) wherein Y is an optionally substituted phenyl group. In one embodiment, Y is a phenyl group. In another embodiment, the phenyl group is optionally substituted with at least one $R_6$ selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In a further embodiment, $R_6$ is $CH_2(NR_AR_B)$. In yet a further embodiment, $R_A$ is H or alkyl. In another embodiment, $R_A$ is $C_1$-$C_6$alkyl. In yet another embodiment, $R_A$ is $CH_3$. In another embodiment, $R_B$ is H or alkyl. In one embodiment, $R_B$ is $C_1$-$C_6$alkyl. In yet another embodiment, $R_B$ is $CH_3$. In a further embodiment, $R_6$ is $CH_2NHCH_3$. In yet a further embodiment, $R_6$ is $CH_2NCH_3CH_3$. In one embodiment, $R_6$ is (C=O)heterocycloalkyl(C=O)alkyl. In one embodiment $R_6$ is (C=O)heterocycloalkyl(C=O)alkyl wherein the heterocycloalkyl group has at least one heteroatom selected from O, N, and S. In another embodiment, the heterocycloalkyl group has two N atoms. In a further embodiment, $R_6$ is (C=O)heterocycloalkyl(C=O)alkyl wherein alkyl is selected from methyl, ethyl, n-propyl, iso-propyl, cyclopropyl, n-butyl, iso-butyl, and t-butyl. In one embodiment, the alkyl group is cyclopropyl. In another embodiment, the alkyl group is iso-propyl. In one embodiment, $R_6$ is

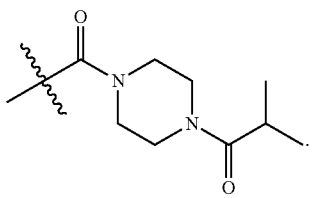 [SMILES: *C(=O)N1CCN(C(=O)C(C)C)CC1]

In another embodiment, $R_6$ is

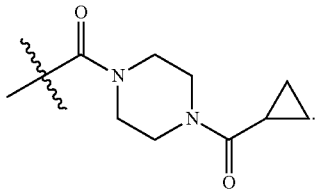 [SMILES: *C(=O)N1CCN(C(=O)C2CC2)CC1]

Presented herein are PARP inhibitor compounds of Formula (I) wherein Y is an optionally substituted heteroaryl group. In one embodiment, the heteroaryl group is selected from pyridine, pyrimidine, pyrazine, pyrazole, oxazole, thiazole, isoxazole, isothiazole, 1,3,4-oxadiazole, pyridazine, 1,3,5-trazine, 1,2,4-triazine, quinoxaline, benzimidazole, benzotriazole, purine, 1H-[1,2,3]triazolo[4,5-d]pyrimidine, triazole, imidazole, thiophene, furan, isobenzofuran, pyrrole, indolizine, isoindole, indole, indazole, isoquinoline, quinoline, phthalazine, naphthyridine, quinazoline, cinnoline, and pteridine. In one embodiment, Y is pyridine. In another embodiment, Y is optionally substituted pyridine. In one embodiment, Y is imidazole. In another embodiment, Y is optionally substituted imidazole. In one embodiment, Y is triazole. In another embodiment, Y is optionally substituted triazole.

In one embodiment, Y is a substituent independently selected from the group consisting of hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl alkylsulfonyl, arylsulfonyl, heteroarylsulfonyl, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene. In one embodiment, Y is alkyl. In another embodiment, Y is $C_1$-$C_6$ alkyl. In a further embodiment, Y is selected from methyl, ethyl, n-propyl, iso-propyl, n-butyl, iso-butyl or tert-butyl. In another embodiment, Y is iso-propyl.

Also disclosed herein are compounds of Formula (I) wherein Y is an optionally substituted heterocycloalkyl group. In one embodiment, the heterocycloalkyl group is selected from pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. In another embodiment the heterocycloalkyl group is selected from pyrrolidinyl, imidazolidinyl, piperidinyl, piperazinyl, pyrazolidinyl, tetrahydrofuranyl, tetrahydrothiophenyl, 1,3-oxathiolanyl, indolinyl, isoindolinyl, morpholinyl, and pyrazolinyl. In another embodiment, the heterocycloalkyl group is piperidinyl.

In another aspect is a PARP inhibitor compound of Formula (IA):

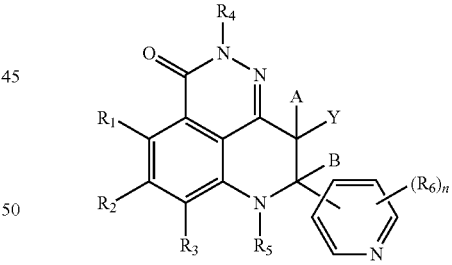

Formula (IA)

or a therapeutically acceptable salt, solvate or prodrug thereof wherein $R_1$, $R_2$, and $R_3$ are each independently selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl;

$R_A$ and $R_B$ are independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$-alkyl)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or S(O)$_q$—, wherein q is 1 or 2 and the 3-10 membered heterocycle ring is optionally substituted with one or more substituents; $R_4$ and $R_5$ are each independently selected from the group consisting of hydrogen, alkyl, cycloalkyl, alkoxyalkyl, haloalkyl, hydroxyalkylene, and (NR$_A$R$_B$)alkylene;

A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl, wherein B is not OH;

Y is selected from the group consisting of:
  a) an aryl group optionally substituted with 1, 2, or 3 substituents $R_6$; $R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, NR$_A$R$_B$, (NR$_A$R$_B$)$C_1$-$C_6$alkylene, (NR$_A$R$_B$)carbonyl, (NR$_A$R$_B$)carbonylalkylene, (NR$_A$R$_B$)sulfonyl, and (NR$_A$R$_B$)sulfonylalkylene;
  b) a heteroaryl group optionally substituted with 1, 2, or 3 substituents $R_6$; $R_6$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkylene, nitro, oxo, heteroaryl, heteroarylalkoxy, heteroaryloxy, heteroarylthio, heteroarylalkylthio, heterocycloalkyl, heterocycloalkoxy, heterocycloalkylthio, heterocyclooxy, heterocyclothio, NR$_A$R$_B$, (NR$_A$R$_B$)alkylene, (NR$_A$R$_B$)carbonyl, (NR$_A$R$_B$)carbonylalkylene, (NR$_A$R$_B$)sulfonyl, and (NR$_A$R$_B$)sulfonylalkylene;
  c) a substituent independently selected from the group consisting of hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl alkylsulfonyl, arylsulfonyl, heteroarylsulfonyl, (NR$_A$R$_B$)alkylene, (NR$_A$R$_B$)carbonyl, (NR$_A$R$_B$) carbonylalkylene, (NR$_A$R$_B$)sulfonyl, and (NR$_A$R$_B$) sulfonylalkylene; and
  n is an integer from 0-4; or a pharmaceutically acceptable salt, solvate or prodrug thereof.

In another embodiment is a PARP inhibitor compound of Formula (IA) having the structure:

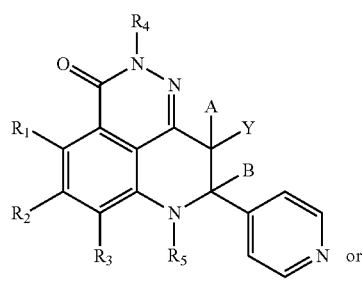

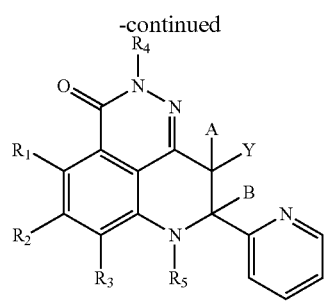

or a pharmaceutically acceptable salt, solvate, or prodrug thereof.

In one embodiment is a PARP inhibitor compound of Formula (IA) wherein Y is an aryl group. In another embodiment, Y is a heteroaryl group. In a further embodiment, the aryl group is a phenyl group. In yet a further embodiment is a compound of Formula (IA) wherein the phenyl group is substituted with at least one $R_6$. In yet another embodiment the phenyl group is substituted with at least one $R_6$ selected from Br, Cl, F, or I. In one embodiment $R_6$ is F. In one embodiment is a compound of Formula (IA) wherein the phenyl group is substituted with at least one $R_6$ selected from (NR$_A$R$_B$)$C_1$-$C_6$alkylene, (NR$_A$R$_B$)carbonyl, (NR$_A$R$_B$)carbonylalkylene, (NR$_A$R$_B$)sulfonyl, and (NR$_A$R$_B$)sulfonylalkylene. In one embodiment $R_6$ is (NR$_A$R$_B$)$C_1$-$C_6$alkylene. In another embodiment $C_1$-$C_6$alkylene is selected from methylene, ethylene, n-propylene, iso-propylene, n-butylene, iso-butylene, and tert-butylene. In yet another embodiment $C_1$-$C_6$alkylene is methylene. In yet a further embodiment $R_A$ and $R_B$ are each independently hydrogen, $C_1$-$C_6$alkyl, or $C_3$-$C_8$cycloalkyl. In one embodiment $C_1$-$C_6$alkyl is selected from methyl, ethyl, n-propyl, iso-propyl, n-butyl, iso-butyl, and tert-butyl. In one embodiment $C_1$-$C_6$alkyl is methyl. In another embodiment $C_1$-$C_6$alkyl is ethyl. In one embodiment is a compound of Formula (IA) wherein $C_3$-$C_8$cycloalkyl is cyclopropyl, cyclobutyl, cyclopentyl, and cyclohexyl. In a further embodiment $C_3$-$C_8$cycloalkyl is cyclopropyl. In one embodiment is a compound of Formula (IA) wherein $R_6$ is hydroxyalkylene. In one embodiment hydroxyalkylene is selected from $CH_2OH$, $CH_2CH_2OH$, $CH_2CH_2CH_2OH$, $CH(OH)CH_3$, $CH(OH)CH_2CH_3$, $CH_2CH(OH)CH_3$, and $CH_2CH_2CH_2OH$. In another embodiment $R_A$ and $R_B$ taken together with the nitrogen to which they are attached form a 6 membered heterocycle ring having 1 heteroatom or hetero functionality selected from the group consisting of —O—, —NH, or —N($C_1$-$C_6$alkyl). In yet another embodiment the hetero functionality is —N($C_1$-$C_6$alkyl). In a further embodiment $C_1$-$C_6$alkyl is selected from methyl, ethyl, n-propyl, iso-propyl, n-butyl, iso-butyl, and tert-butyl. In yet a further embodiment $C_1$-$C_6$alkyl is methyl.

In one embodiment is a PARP inhibitor compound of Formula (IA) wherein Y is a heteroaryl group optionally substituted with at least one $R_6$. In another embodiment the heteroaryl group is selected from furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In yet another embodiment the heteroaryl group is imidazole. In a further embodiment imidazole is substituted with $C_1$-$C_6$alkyl selected from methyl, ethyl, n-propyl, iso-propyl, n-butyl, iso-butyl, and tert-butyl. In yet further embodiment $C_1$-$C_6$alkyl is methyl. In one embodiment the heteroaryl group is furan. In another embodiment the heteroaryl group is thiazole. In yet another embodiment the heteroaryl group is 1,3,4-oxadiazole. In a further embodiment heteroaryl group is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl.

In one embodiment is a PARP inhibitor compound of Formula (IA) wherein A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl and B is not OH.

In yet another embodiment is a PARP inhibitor compound selected from:

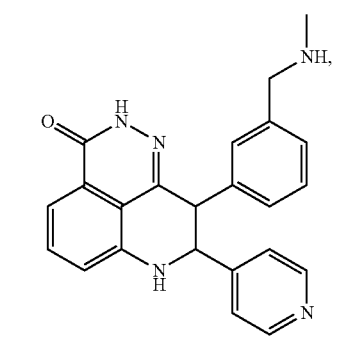

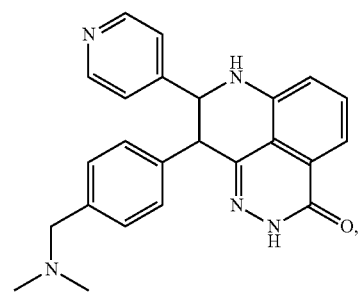

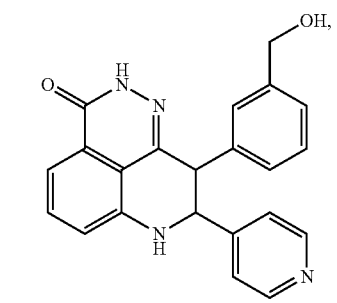

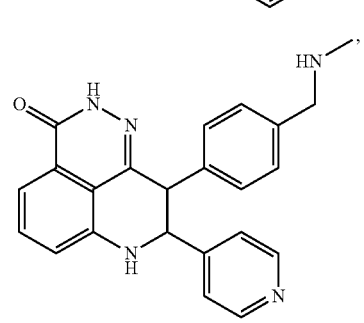

-continued

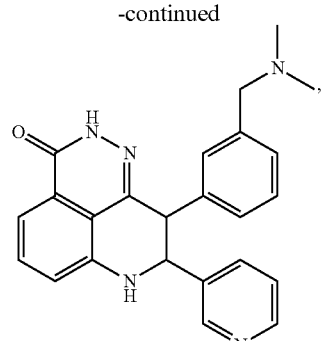

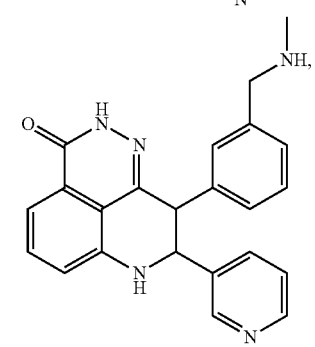

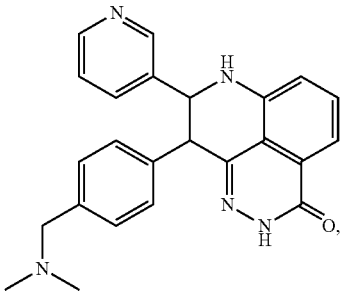

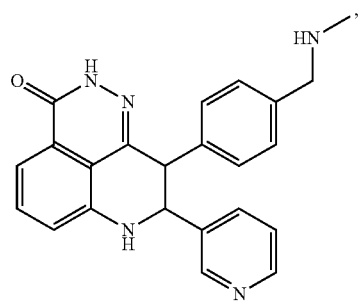

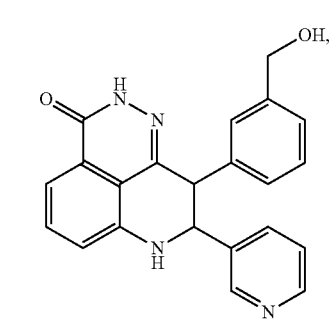

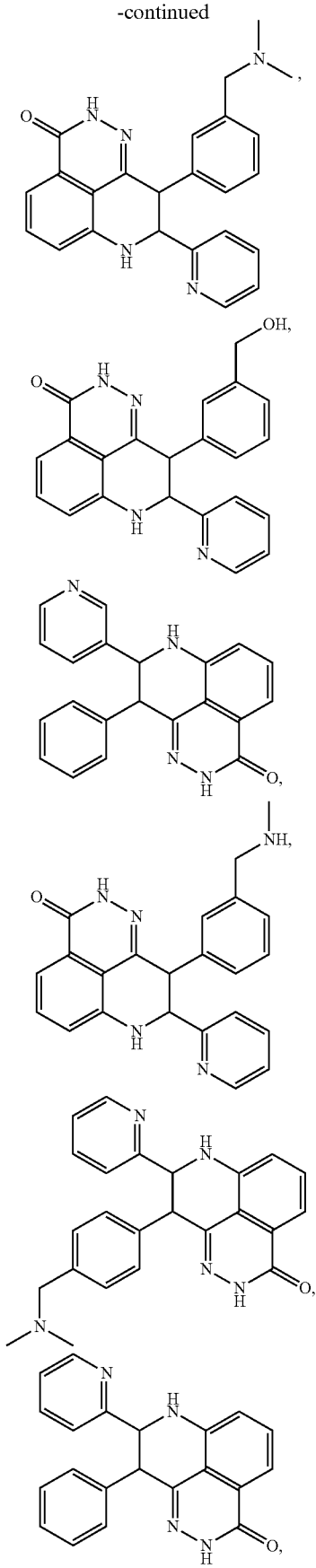
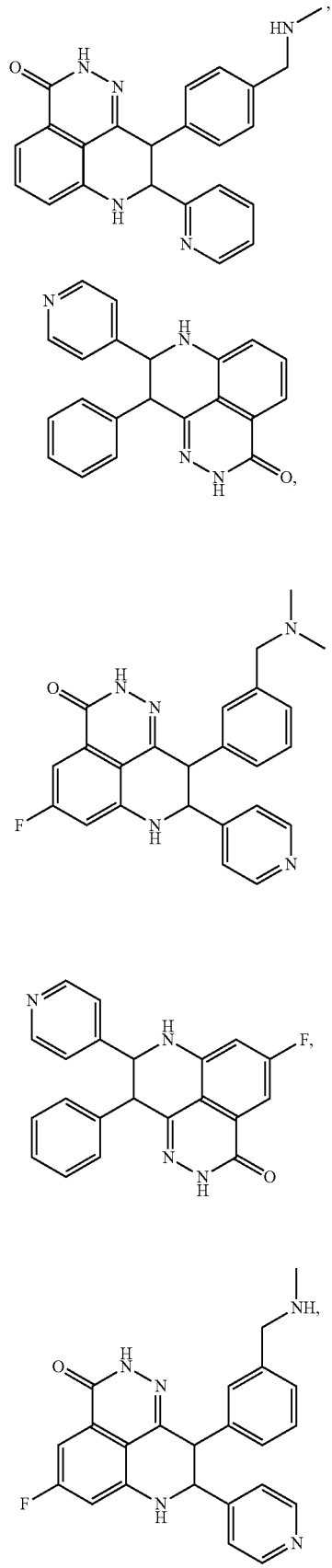

-continued

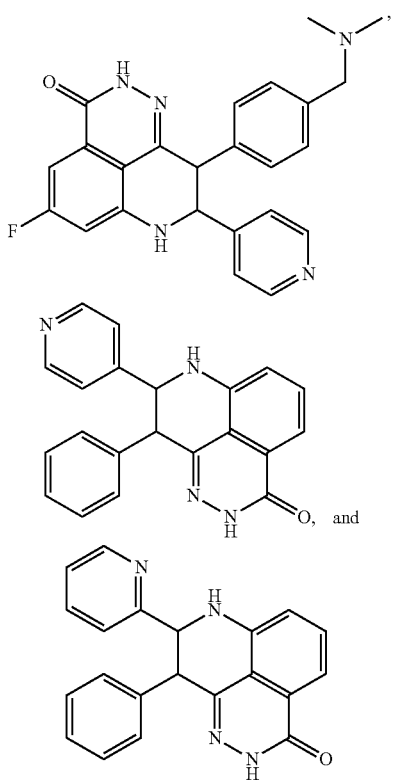

or a pharmaceutically acceptable salt, solvate or prodrug thereof.

In one embodiment is a PARP inhibitor compound of Formula (I) wherein Y is a heteroaryl group selected from furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In another embodiment, Y is an imidazole group. In yet another embodiment, the imidazole group is substituted with a $C_1$-$C_6$alkyl group. In another embodiment, the $C_1$-$C_6$alkyl group is methyl, ethyl, n-propyl, iso-propyl, n-butyl, iso-butyl, and tert-butyl. In a further embodiment $C_1$-$C_6$alkyl is methyl. In another embodiment is a compound of Formula (I) wherein Y is a substituted imidazole group and Z is selected from an aryl group or a heteroaryl group. In a further embodiment, Z is an aryl group. In yet a further embodiment, the aryl group is a phenyl group. In yet a further embodiment, the aryl group is a phenyl group substituted by a halogen. In yet a further embodiment Z is a heteroaryl group. In another embodiment, the heteroaryl group is furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In a further embodiment, the heteroaryl group is imidazole. In another embodiment, the imidazole group is substituted with a $C_1$-$C_6$alkyl group. In another embodiment, the $C_1$-$C_6$alkyl group is methyl, ethyl, n-propyl, iso-propyl, n-butyl, iso-butyl, and tert-butyl. In a further embodiment $C_1$-$C_6$alkyl is methyl.

In another embodiment is a PARP inhibitor compound of Formula (I) wherein Y is a triazole group. In yet another embodiment, the triazole group is substituted with a $C_1$-$C_6$alkyl group. In another embodiment, the $C_1$-$C_6$alkyl group is methyl, ethyl, n-propyl, iso-propyl, n-butyl, iso-butyl, and tert-butyl. In a further embodiment $C_1$-$C_6$alkyl is methyl. In another embodiment is a compound of Formula (I) wherein Y is a substituted triazole group and Z is selected from an aryl group or a heteroaryl group. In a further embodiment, Z is an aryl group. In yet a further embodiment, the aryl group is a phenyl group. In yet a further embodiment, the aryl group is a phenyl group substituted by a halogen. In yet a further embodiment Z is a heteroaryl group. In another embodiment, the heteroaryl group is furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In a further embodiment, the heteroaryl group is triazole. In another embodiment, the triazole group is substituted with a $C_1$-$C_6$alkyl group. In another embodiment, the $C_1$-$C_6$alkyl group is methyl, ethyl, n-propyl, iso-propyl, n-butyl, iso-butyl, and tert-butyl. In a further embodiment $C_1$-$C_6$alkyl is methyl.

In another embodiment is a PARP inhibitor compound selected from

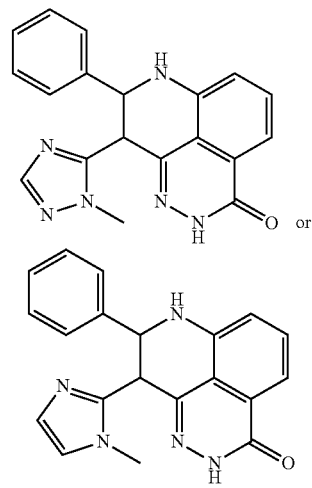

or a pharmaceutically acceptable salt, solvate or prodrug thereof.

In one aspect is a PARP inhibitor compound of Formula (II):

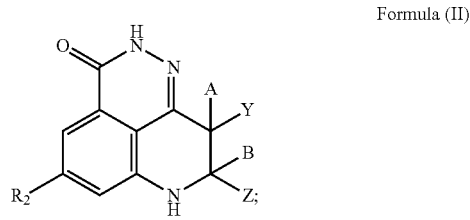

Formula (II)

wherein:
Y is an aryl or heteroaryl group optionally substituted with at least one $R_6$;
Z is an aryl group optionally substituted with at least one $R_6$;

$R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;

$R_2$ is selected from hydrogen, Br, Cl, I, or F;

A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl, wherein B is not OH;

$R_A$, and $R_B$ are independently selected from the group consisting of hydrogen, $C_1$-$C_6$alkyl, $C_3$-$C_8$cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$alkyl)-, —NCO($C_1$-$C_6$alkyl)-, —NCO($C_3$-$C_8$cycloalkyl)-, —N(aryl)-, —N(aryl-$C_1$-$C_6$alkyl-)-, —N(substituted-aryl-$C_1$-$C_6$alkyl-)-, —N(heteroaryl)-, —N(heteroaryl-$C_1$-$C_6$alkyl-)-, —N(substituted-heteroaryl-$C_1$-$C_6$alkyl-)-, and —S— or $S(O)_q$—, wherein q is 1 or 2 and the 3-10 membered heterocycle ring is optionally substituted with one or more substituents; or a pharmaceutically acceptable salt, solvate or prodrug thereof.

In one embodiment is a PARP inhibitor compound of Formula (II) wherein Y is an aryl group. In another embodiment the aryl group is a phenyl group. In yet another embodiment the phenyl group is substituted with at least one $R_6$ selected from Br, Cl, F, or I. In one embodiment $R_6$ is F. In one embodiment the phenyl group is substituted with at least one $R_6$ selected from $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In one embodiment $R_6$ is $(NR_AR_B)C_1$-$C_6$alkylene. In another embodiment $C_1$-$C_6$alkylene is selected from methylene, ethylene, n-propylene, iso-propylene, n-butylene, iso-butylene, and tert-butylene. In yet another embodiment $C_1$-$C_6$alkylene is methylene. In a further embodiment $R_A$ and $R_B$ are each independently hydrogen, $C_1$-$C_6$alkyl, or $C_3$-$C_8$cycloalkyl. In one embodiment $C_1$-$C_6$alkyl is selected from methyl, ethyl, n-propyl, iso-propyl, n-butyl, iso-butyl, and tert-butyl. In one embodiment $C_1$-$C_6$alkyl is methyl. In another embodiment $C_1$-$C_6$alkyl is ethyl. In yet another embodiment $C_3$-$C_8$cycloalkyl is cyclopropyl, cyclobutyl, cyclopentyl, and cyclohexyl. In a further embodiment $C_3$-$C_8$cycloalkyl is cyclopropyl. In yet a further embodiment $R_6$ is hydroxyalkylene. In one embodiment hydroxyalkylene is selected from $CH_2OH$, $CH_2CH_2OH$, $CH_2CH_2CH_2OH$, $CH(OH)CH_3$, $CH(OH)CH_2CH_3$, $CH_2CH(OH)CH_3$, and $CH_2CH_2CH_2CH_2OH$. In another embodiment $R_A$ and $R_B$ taken together with the nitrogen to which they are attached form a 6 membered heterocycle ring having 1 heteroatom or hetero functionality selected from the group consisting of —O—, —NH, or —N($C_1$-$C_6$alkyl). In yet another embodiment the hetero functionality is —N($C_1$-$C_6$alkyl). In a further embodiment $C_1$-$C_6$alkyl is selected from methyl, ethyl, n-propyl, iso-propyl, n-butyl, iso-butyl, and tert-butyl. In yet a further embodiment $C_1$-$C_6$alkyl is methyl.

In one embodiment is a PARP inhibitor compound of Formula (II) wherein Y is a heteroaryl group optionally substituted with at least one $R_6$. In another embodiment the heteroaryl group is selected from furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline. In yet another embodiment the heteroaryl group is imidazole. In a further embodiment imidazole is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl. In one embodiment the heteroaryl group is furan. In another embodiment the heteroaryl group is thiazole. In yet another embodiment the heteroaryl group is 1,3,4-oxadiazole. In a further embodiment heteroaryl group is substituted with $C_1$-$C_6$alkyl selected from methyl, ethyl, n-propyl, iso-propyl, n-butyl, iso-butyl, and tert-butyl. In yet a further embodiment $C_1$-$C_6$alkyl is methyl.

In one embodiment is a PARP inhibitor compound of Formula (II) wherein Z is an aryl group. In another embodiment the aryl group is a phenyl group. In yet another embodiment the phenyl group is substituted with at least one $R_6$ selected from Br, Cl, F, or I. In a further embodiment $R_6$ is F. In yet a further embodiment $R_6$ is Cl. In one embodiment the phenyl group is substituted with at least one $R_6$ selected from $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene. In another embodiment $R_6$ is $(NR_AR_B)C_1$-$C_6$alkylene. In yet another embodiment $C_1$-$C_6$alkylene is selected from methylene, ethylene, n-propylene, iso-propylene, n-butylene, iso-butylene, and tert-butylene. In yet a further embodiment $C_1$-$C_6$alkylene is methylene. In a further embodiment $R_A$ and $R_B$ are each independently hydrogen, $C_1$-$C_6$alkyl, or $C_1$-$C_8$cycloalkyl. In one embodiment $C_1$-$C_6$alkyl is selected from methyl, ethyl, n-propyl, iso-propyl, n-butyl, iso-butyl, and tert-butyl. In another embodiment $C_1$-$C_6$alkyl is methyl. In yet another embodiment $R_A$ and $R_B$ taken together with the nitrogen to which they are attached form a 6 membered heterocycle ring having 1 heteroatom or hetero functionality selected from the group consisting of —O—, —NH, or —N($C_1$-$C_6$alkyl). In a further embodiment the hetero functionality is —N($C_1$-$C_6$alkyl). In one embodiment $C_1$-$C_6$alkyl is selected from methyl, ethyl, n-propyl, iso-propyl, n-butyl, iso-butyl, and tert-butyl. In yet a further embodiment $C_1$-$C_6$alkyl is methyl. In a further embodiment, $R_6$ is $CH_2(NR_AR_B)$ wherein $NR_AR_B$ is azetidine, pyrrolidine, piperidine or morpholine. In another embodiment $R_2$ is hydrogen. In yet another embodiment $R_2$ is selected from F, Cl, Br, and I. In a further embodiment $R_2$ is F.

In one embodiment is a PARP inhibitor compound of Formula (II) wherein A and B are hydrogen. In another embodiment A and B are independently selected from hydrogen and $C_1$-$C_6$alkyl.

In a further embodiment is a PARP inhibitor compound of Formula (II) wherein Z is aryl and Y is independently selected from the group consisting of a) phenyl group optionally substituted with 1, 2, or 3 $R_6$;

b) a imidazole group optionally substituted with 1, 2, or 3 $R_6$;

c) a triazole group optionally substituted with 1, 2, or 3 $R_6$; and d) a substituent independently selected from the group consisting of hydrogen, alkoxyalkyl, alkoxycarbonylalkyl, alkyl, arylalkyl, cycloalkyl, cycloalkylalkyl, haloalkyl, oxo, heterocycloalkyl, heterocycloalkylalkyl, alkylcarbonyl, arylcarbonyl, heteroarylcarbonyl, $(NR_AR_B)$alkylene $(NR_AR_B)$carbonyl.

In a further embodiment is a PARP inhibitor compound of Formula (II) wherein Z is phenyl and Y is independently selected from the group consisting of
e) phenyl group optionally substituted with 1, 2, or 3 $R_6$;
f) a imidazole group optionally substituted with 1, 2, or 3 $R_6$;
g) a triazole group optionally substituted with 1, 2, or 3 $R_6$; and
h) a substituent independently selected from the group consisting of hydrogen, alkoxyalkyl, alkoxycarbonylalkyl, alkyl, arylalkyl, cycloalkyl, cycloalkylalkyl, haloalkyl, oxo, heterocycloalkyl, heterocycloalkylalkyl, alkylcarbonyl, arylcarbonyl, heteroarylcarbonyl, $(NR_AR_B)$alkylene $(NR_AR_B)$carbonyl.

In a further embodiment is a PARP inhibitor compound of Formula (II) wherein Z is phenyl substituted with 1, 2, or 3 $R_6$ and Y is independently selected from the group consisting of
i) phenyl group optionally substituted with 1, 2, or 3 $R_6$;
j) a imidazole group optionally substituted with 1, 2, or 3 $R_6$;
k) a triazole group optionally substituted with 1, 2, or 3 $R_6$; and
l) a substituent independently selected from the group consisting of hydrogen, alkoxyalkyl, alkoxycarbonylalkyl, alkyl, arylalkyl, cycloalkyl, cycloalkylalkyl, haloalkyl, oxo, heterocycloalkyl, heterocycloalkylalkyl, alkylcarbonyl, arylcarbonyl, heteroarylcarbonyl, $(NR_AR_B)$alkylene $(NR_AR_B)$carbonyl.

In a further embodiment, A is selected from methyl, ethyl, n-propyl, iso-propyl, n-butyl, iso-butyl, tert-butyl, n-pentyl, and n-hexyl. In yet another embodiment, methyl, ethyl, n-propyl, iso-propyl, n-butyl, iso-butyl, tert-butyl, n-pentyl, and n-hexyl are optionally substituted with OH, $NO_2$, CN, Br, Cl, F, and I. In a further embodiment A is methyl. In yet another embodiment, A is selected from F, Cl, Br, and I. In another embodiment, A is $C_3$-$C_8$cycloalkyl. In a further embodiment, A is OH. In another embodiment, A is cyclopropyl, cyclobutyl, cyclopentyl, or cyclohexyl. In one embodiment, A is substituted with OH, $NO_2$, or CN. In a further embodiment, A is hydrogen. In a further embodiment, B is hydrogen. In a further embodiment, B is $C_1$-$C_6$alkyl. In a further embodiment, B is selected from methyl, ethyl, n-propyl, iso-propyl, n-butyl, iso-butyl, tert-butyl, n-pentyl, and n-hexyl. In yet another embodiment, methyl, ethyl, n-propyl, iso-propyl, n-butyl, iso-butyl, tert-butyl, n-pentyl, and n-hexyl are optionally substituted with OH, $NO_2$, CN, Br, Cl, F, and I. In a further embodiment B is methyl. In yet another embodiment, B is selected from F, Cl, Br, and I. In another embodiment, B is $C_3$-$C_8$cycloalkyl. In another embodiment, B is cyclopropyl, cyclobutyl, cyclopentyl, or cyclohexyl. In one embodiment, A is substituted with OH, $NO_2$, or CN. In a further embodiment, is a compound of Formula (II) wherein A is hydrogen and B is selected from Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl. In another embodiment, is a compound of Formula (II) wherein B is hydrogen and A is selected from Br, Cl, F, I, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl. In yet another embodiment, both A and B are hydrogen. In a further embodiment, both A and B are selected from Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl wherein B is not OH.

Also described herein are stereoisomers of PARP inhibitor compounds of Formula (I), (IA), or (II), such as enantiomers, diastereomers, and mixtures of enantiomers or diastereomers. In one embodiment is a stereoisomer of a compound of Formula (II) having the structures:

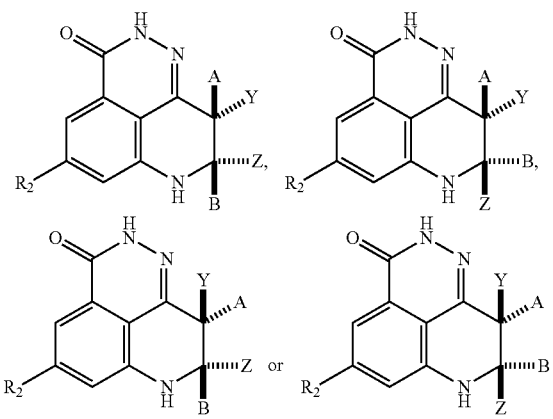

wherein:
Y is an aryl or heteroaryl group optionally substituted with at least one $R_6$;
Z is an aryl group optionally substituted with at least one $R_6$;
A and B are each independently selected from hydrogen, Br, Cl, F, I, OH, $C_1$-$C_6$alkyl, $C_3$-$C_8$cycloalkyl, alkoxy, alkoxyalkyl wherein $C_1$-$C_6$alkyl, $C_3$-$C_8$cycloalkyl, alkoxy, alkoxyalkyl are optionally substituted with at least one substituent selected from OH, $NO_2$, CN, Br, Cl, F, I, $C_1$-$C_6$alkyl, and $C_3$-$C_8$cycloalkyl, wherein B is not OH;
$R_6$ is selected from OH, $NO_2$, CN, Br, Cl, F, I, $C_1$-$C_6$alkyl, $C_3$-$C_8$cycloalkyl, $C_2$-$C_8$heterocycloalkyl; $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_2$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;
$R_2$ is selected from hydrogen, Br, Cl, I, or F;
$R_A$ and $R_B$ are independently selected from the group consisting of hydrogen, $C_1$-$C_6$alkyl, $C_3$-$C_8$cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$alkyl)-, —NCO($C_1$-$C_6$alkyl)-, —NCO($C_3$-$C_8$cycloalkyl)-, —N(aryl)-, —N(aryl-$C_1$-$C_6$alkyl-)-, —N(substituted-aryl-$C_1$-$C_6$alkyl-)-, —N(heteroaryl)-, —N(heteroaryl-$C_1$-$C_6$alkyl-)-, —N(substituted-heteroaryl-$C_1$-$C_6$alkyl-)-, and —S— or $S(O)_q$—, wherein q is 1 or 2 and the 3-10 membered heterocycle ring is optionally substituted with one or more substituents; or a pharmaceutically acceptable salt, solvate or prodrug thereof.

In one embodiment is the stereoisomer of the PARP inhibitor compound of Formula (II) shown above, having the substituents shown above, wherein $R_2$ is fluorine. In another embodiment is the compound of Formula (II) shown above, having the substituents shown above, wherein Y is an imidazole group. In another embodiment is the compound of Formula (II) shown above, having the substituents shown above, wherein the imidazole group of Y is substituted with a $C_1$-$C_6$alkyl group. In a further embodiment, the $C_1$-$C_6$alkyl is methyl. In yet another embodiment is a compound of Formula (II), shown above, having the substituents shown above, wherein Y is a triazole group. In another embodiment is the compound of Formula (II) shown above, having the substituents shown above, wherein the triazole group of Y is substituted with a $C_1$-$C_6$alkyl group. In a further embodiment, the $C_1$-$C_6$alkyl is methyl. In yet a further embodiment is the compound of Formula (II) shown above, having the substituents above, wherein the Y group is an aryl group. In a further embodiment is the compound of Formula (II) shown above, having the substituents shown above, wherein the aryl group of Y is a phenyl group. In a further embodiment, the phenyl group is substituted with a halogen. In yet a further embodiment, the halogen is F. In yet another embodiment the halogen is selected from Br, Cl, and I. In yet another embodiment, is the compound of Formula (II) shown above, having the substituents shown above, wherein Z is an aryl group. In yet another embodiment is the compound of Formula (II) shown above, having the substituents shown above, wherein the aryl group of Z is a phenyl group. In a further embodiment, the phenyl group of Z is substituted with a halogen, selected from F, Br, Cl, and I. In yet another embodiment, the phenyl group of Z is substituted with F. In yet a further embodiment the phenyl group of Z is substituted with $C_1$-$C_6$alkylene (NR$_A$R$_B$). In yet a further embodiment, the $C_1$-$C_6$alkylene group is methylene. In yet another embodiment NRARB is azetidine.

In one embodiment is a PARP inhibitor compound selected from:
(8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one,
(8R,9S)-5-fluoro-8-(4-fluorophenyl)-9-(1-methyl-1H-1,2,4-triazol-5-yl)-8,9-dihydro-2H-pyrido[4,3,2-de]phthalazin-3(7H)-one,
(8S,9R)-8-(4-fluorophenyl)-9-(1-methyl-1H-imidazol-2-yl)-8,9-dihydro-2H-pyrido[4,3,2-de]phthalazin-3(7H)-one,
(8R,9S)-8-(4-fluorophenyl)-9-(1-methyl-1H-imidazol-2-yl)-8,9-dihydro-2H-pyrido[4,3,2-de]phthalazin-3(7H)-one,
(8S,9R)-8-(4-fluorophenyl)-9-(1-methyl-1H-1,2,4-triazol-5-yl)-8,9-dihydro-2H-pyrido[4,3,2-de]phthalazin-3(7H)-one,
(8R,9S)-8-(4-fluorophenyl)-9-(1-methyl-1H-1,2,4-triazol-5-yl)-8,9-dihydro-2H-pyrido[4,3,2-de]phthalazin-3(7H)-one,
(8S,9R)-5-fluoro-8-(4-fluorophenyl)-9-(1-methyl-1H-imidazol-2-yl)-8,9-dihydro-2H-pyrido[4,3,2-de]phthalazin-3(7H)-one,
(8R,9S)-5-fluoro-8-(4-fluorophenyl)-9-(1-methyl-1H-imidazol-2-yl)-8,9-dihydro-2H-pyrido[4,3,2-de]phthalazin-3(7H)-one,
(8S,9R)-5-fluoro-9-(1-methyl-1H-imidazol-2-yl)-8-phenyl-8,9-dihydro-2H-pyrido[4,3,2-de]phthalazin-3(7H)-one,
(8R,9S)-5-fluoro-9-(1-methyl-1H-imidazol-2-yl)-8-phenyl-8,9-dihydro-2H-pyrido[4,3,2-de]phthalazin-3(7H)-one,
(8S,9R)-8-(4-(azetidin-1-ylmethyl)phenyl)-9-(4-fluorophenyl)-8,9-dihydro-2H-pyrido[4,3,2-de]phthalazin-3(7H)-one, and
(8R,9S)-8-(4-(azetidin-1-ylmethyl)phenyl)-9-(4-fluorophenyl)-8,9-dihydro-2H-pyrido[4,3,2-de]phthalazin-3(7H)-one, or a pharmaceutically acceptable salt, solvate or prodrug thereof.

In one aspect is a compound selected from:
9-diphenyl-8,9-dihydro-2H-pyrido[4,3,2-de]phthalazin-3(7H)-one;
8,9-bis(4-((methylamino)methyl)phenyl-8,9-dihydro-2H-pyrido[4,3,2-de]phthalazin-3(7H)-one;
8,9-di(pyridin-4-yl)-8,9-dihydro-2H-pyrido[4,3,2-de]phthalazin-3(7H)-one;
8,9-di(pyridin-3-yl)-8,9-dihydro-2H-pyrido[4,3,2-de]phthalazin-3(7H)-one;
8,9-di(pyridin-2-yl)-8,9-dihydro-2H-pyrido[4,3,2-de]phthalazin-3(7H)-one;
9-isopropyl-8-phenyl-8,9-dihydro-2H-pyrido[4,3,2-de]phthalazin-3(7H)-one;
9-(4-((methylamino)methyl)phenyl)-8-phenyl-8,9-dihydro-2H-pyrido[4,3,2-de]phthalazin-3(7H)-one;
9-(4-((dimethylamino)methyl)phenyl)-8-phenyl-8,9-dihydro-2H-pyrido[4,3,2-de]phthalazin-3(7H)-one;
9-(3-((methylamino)methyl)phenyl)-8-phenyl-8,9-dihydro-2H-pyrido[4,3,2-de]phthalazin-3(7H)-one;
8-(4-((methylamino)methyl)phenyl)-9-phenyl-8,9-dihydro-2H-pyrido[4,3,2-de]phthalazin-3(7H)-one;
8,9-bis(3-((methylamino)methyl)phenyl)-8,9-dihydro-2H-pyrido[4,3,2-de]phthalazin-3(7H)-one;
9-(4-(hydroxymethyl)phenyl)-8-phenyl-8,9-dihydro-2H-pyrido[4,3,2-de]phthalazin-3(7H)-one;
9-(3-(4-isobutyrylpiperazine-1-carbonyl)phenyl)-8-phenyl-8,9-dihydro-2H-pyrido[4,3,2-de]phthalazin-3(7H)-one;
8,9-bis(3-(4-isobutyrylpiperazine-1-carbonyl)phenyl)-8,9-dihydro-2H-pyrido[4,3,2-de]phthalazin-3(7H)-one;
9-(piperidin-3-yl)-8-(pyridin-3-yl)-8,9-dihydro-2H-pyrido[4,3,2-de]phthalazin-3(7H)-one;
9-(piperidin-4-yl)-8-(pyridin-4-yl)-8,9-dihydro-2H-pyrido[4,3,2-de]phthalazin-3(7H)-one;
8,9-bis(4-((dimethylamino)methyl)phenyl)-8,9-dihydro-2H-pyrido[4,3,2-de]phthalazin-3(7H)-one;
9-(4-(4-(cyclopropanecarbonyl)piperazine-1-carbonyl)phenyl)-8-(4((methylamino)methyl)phenyl)-8,9-dihydro-2H-pyrido[4,3,2-de]phthalazin-3(7H)-one;
9-(4-(4-(cyclopropanecarbonyl)piperazine-1-carbonyl)phenyl)-8-(4((dimethylamino)methyl)phenyl)-8,9-dihydro-2H-pyrido[4,3,2-de]phthalazin-3(7H)-one;
8-(4-(hydroxymethyl)phenyl)-9-(4-(4-isobutyrylpiperazine-1-carbonyl)phenyl)-8,9-dihydro-2H-pyrido[4,3,2-de]phthalazin-3(7H)-one;
8-(4-((dimethylamino)methyl)phenyl)-9-(4-(4-isobutyrylpiperazine-1-carbonyl)phenyl)-8,9-dihydro-2H-pyrido[4,3,2-de]phthalazin-3(7H)-one;
9-(4-(4-(cyclopropanecarbonyl)piperazine-1-carbonyl)phenyl)-8-phenyl-8,9-dihydro-2H-pyrido[4,3,2-de]phthalazin-3(7H)-one;
9-(3-(4-(cyclopropanecarbonyl)piperazine-1-carbonyl)phenyl)-8-phenyl-8,9-dihydro-2H-pyrido[4,3,2-de]phthalazin-3(7H)-one;
9-(3-((dimethylamino)methyl)phenyl)-8-phenyl-8,9-dihydro-2H-pyrido[4,3,2-de]phthalazin-3(7H)-one;
8-(3-((methylamino)methyl)phenyl)-9-phenyl-8,9-dihydro-2H-pyrido[4,3,2-de]phthalazin-3(7H)-one;
8-(4-((dimethylamino)methyl)phenyl)-9-phenyl-8,9-dihydro-2H-pyrido[4,3,2-de]phthalazin-3(7H)-one;
8-(4-(morpholinomethyl)phenyl)-9-phenyl-8,9-dihydro-2H-pyrido[4,3,2-de]phthalazin-3(7H)-one;
8-(4-(hydroxymethyl)phenyl)-9-phenyl-8,9-dihydro-2H-pyrido[4,3,2-de]phthalazin-3(7H)-one;

9-(3-(4-(cyclopropanecarbonyl)piperazine-1-carbonyl)phenyl)-8-(4-((dimethylamino)methyl)phenyl)-8,9-dihydro-2H-pyrido[4,3,2-de]phthalazin-3(7H)-one;

9-(3-(4-(cyclopropanecarbonyl)piperazine-1-carbonyl)phenyl)-8-(4-(hydroxymethyl)phenyl)-8,9-dihydro-2H-pyrido[4,3,2-de]phthalazin-3(7H)-one;

9-(4-(4-isobutyrylpiperazine-1-carbonyl)phenyl)-8-(4-((methylamino)methyl)phenyl)-8,9-dihydro-2H-pyrido[4,3,2-de]phthalazin-3(7H)-one;

9-(3-(4-isobutyrylpiperazine-1-carbonyl)phenyl)-8-(pyridin-4-yl)-8,9-dihydro-2H-pyrido[4,3,2-de]phthalazin-3(7H)-one;

9-(3-((dimethylamino)methyl)phenyl)-8-(pyridin-4-yl)-8,9-dihydro-2H-pyrido[4,3,2-de]phthalazin-3(7H)-one;

9-(3-((methylamino)methyl)phenyl)-8-(pyridin-4-yl)-8,9-dihydro-2H-pyrido[4,3,2-de]phthalazin-3(7H)-one;

9-(4-((dimethylamino)methyl)phenyl)-8-(pyridin-4-yl)-8,9-dihydro-2H-pyrido[4,3,2-de]phthalazin-3(7H)-one;

9-(3-(hydroxymethyl)phenyl)-8-(pyridin-4-yl)-8,9-dihydro-2H-pyrido[4,3,2-de]phthalazin-3(7H)-one;

9-(4-((methylamino)methyl)phenyl)-8-(pyridin-4-yl)-8,9-dihydro-2H-pyrido[4,3,2-de]phthalazin-3(7H)-one;

9-(3-((dimethylamino)methyl)phenyl)-8-(pyridin-3-yl)-8,9-dihydro-2H-pyrido[4,3,2-de]phthalazin-3(7H)-one;

9-(3-((methylamino)methyl)phenyl)-8-(pyridin-3-yl)-8,9-dihydro-2H-pyrido[4,3,2-de]phthalazin-3(7H)-one;

9-(4-((dimethylamino)methyl)phenyl)-8-(pyridin-3-yl)-8,9-dihydro-2H-pyrido[4,3,2-de]phthalazin-3(7H)-one;

9-(4-((methylamino)methyl)phenyl)-8-(pyridin-3-yl)-8,9-dihydro-2H-pyrido[4,3,2-de]phthalazin-3(7H)-one;

9-(3-(hydroxymethyl)phenyl)-8-(pyridin-3-yl)-8,9-dihydro-2H-pyrido[4,3,2-de]phthalazin-3(7H)-one;

9-(3-((dimethylamino)methyl)phenyl)-8-(pyridin-2-yl)-8,9-dihydro-2H-pyrido[4,3,2-de]phthalazin-3(7H)-one;

9-(3-((methylamino)methyl)phenyl)-8-(pyridin-2-yl)-8,9-dihydro-2H-pyrido[4,3,2-de]phthalazin-3(7H)-one;

9-(3-(hydroxymethyl)phenyl)-8-(pyridin-2-yl)-8,9-dihydro-2H-pyrido[4,3,2-de]phthalazin-3(7H)-one;

9-(4-((dimethylamino)methyl)phenyl)-8-(pyridin-2-yl)-8,9-dihydro-2H-pyrido[4,3,2-de]phthalazin-3(7H)-one;

9-(4-((methylamino)methyl)phenyl)-8-(pyridin-2-yl)-8,9-dihydro-2H-pyrido[4,3,2-de]phthalazin-3(7H)-one;

9-phenyl-8-(pyridin-2-yl)-8,9-dihydro-2H-pyrido[4,3,2-de]phthalazin-3(7H)-one;

9-phenyl-8-(pyridin-3-yl)-8,9-dihydro-2H-pyrido[4,3,2-de]phthalazin-3(7H)-one;

9-phenyl-8-(pyridin-4-yl)-8,9-dihydro-2H-pyrido[4,3,2-de]phthalazin-3(7H)-one;

5-fluoro-9-phenyl-8-(pyridin-4-yl)-8,9-dihydro-2H-pyrido[4,3,2-de]phthalazin-3(7H)-one;

9-(3-((dimethylamino)methyl)phenyl)-5-fluoro-8-(pyridin-4-yl)-8,9-dihydro-2H-pyrido[4,3,2-de]phthalazin-3(7H)-one;

5-fluoro-9-(3-((methylamino)methyl)phenyl)-8-(pyridin-4-yl)-8,9-dihydro-2H-pyrido[4,3,2-de]phthalazin-3(7H)-one;

9-(4-((dimethylamino)methyl)phenyl)-5-fluoro-8-(pyridin-4-yl)-8,9-dihydro-2H-pyrido[4,3,2-de]phthalazin-3(7H)-one;

5-fluoro-8,9-diphenyl-8,9-dihydro-2H-pyrido[4,3,2-de]phthalazin-3(7H)-one;

9-(4-((dimethylamino)methyl)phenyl)-5-fluoro-8-phenyl-8,9-dihydro-2H-pyrido[4,3,2-de]phthalazin-one;

5-fluoro-9-(4-((methylamino)methyl)phenyl)-8-phenyl-8,9-dihydro-2H-pyrido[4,3,2-de]phthalazin-one;

9-(3-((dimethylamino)methyl)phenyl)-5-fluoro-8-phenyl-8,9-dihydro-2H-pyrido[4,3,2-de]phthalazin-one;

8-(4-((dimethylamino)methyl)phenyl)-5-fluoro-9-phenyl-8,9-dihydro-2H-pyrido[4,3,2-de]phthalazin-one;

5-fluoro-9-(3-((methylamino)methyl)phenyl)-8-phenyl-8,9-dihydro-2H-pyrido[4,3,2-de]phthalazin-one;

5-fluoro-8-(4-((methylamino)methyl)phenyl)-9-phenyl-8,9-dihydro-2H-pyrido[4,3,2-de]phthalazin-one;

7-methyl-8,9-diphenyl-8,9-dihydro-2H-pyrido[4,3,2-de]phthalazin-3(7H)-one;

7-ethyl-8,9-diphenyl-8,9-dihydro-2H-pyrido[4,3,2-de]phthalazin-3(7H)-one;

5-fluoro-9-(1-methyl-1H-imidazol-2-yl)-8-phenyl-8,9-dihydro-2H-pyrido[4,3,2-de]phthalazin-3(7H)-one;

5-fluoro-8-(4-fluorophenyl)-9-(1-methyl-1H-imidazol-2-yl)-8,9-dihydro-2H-pyrido[4,3,2-de]phthalazin-3(7H)-one;

8-(4-((dimethylamino)methyl)phenyl)-9-(1-methyl-1H-imidazol-2-yl)-8,9-dihydro-2H-pyrido[4,3,2-de]phthalazin-3(7H)-one;

9-(1-isopropyl-1H-imidazol-5-yl)-8-phenyl-8,9-dihydro-2H-pyrido[4,3,2-de]phthalazin-3(7H)-one;

9-(4-methyl-1H-imidazol-2-yl)-8-phenyl-8,9-dihydro-2H-pyrido[4,3,2-de]phthalazin-3(7H)-one;

8-phenyl-9-(thiazol-5-yl)-8,9-dihydro-2H-pyrido[4,3,2-de]phthalazin-3(7H)-one;

9-(furan-3-yl)-8-phenyl-8,9-dihydro-2H-pyrido[4,3,2-de]phthalazin-3(7H)-one;

8-(4-((4-ethylpiperazin-1-yOmethyl)phenyl)-9-phenyl-8,9-dihydro-2H-pyrido[4,3,2-de]phthalazin-3(7H)-one;

9-phenyl-8-(4-(piperazin-1-ylmethyl)phenyl)-8,9-dihydro-2H-pyrido[4,3,2-de]phthalazin-3(7H)-one;

8-(1-methyl-1H-imidazol-2-yl)-9-phenyl-8,9-dihydro-2H-pyrido[4,3,2-de]phthalazin-3(7H)-one;

9-(1-methyl-1H-imidazol-2-yl)-8-phenyl-8,9-dihydro-2H-pyrido[4,3,2-de]phthalazin-3(7H)-one;

8,9-bis(1-methyl-1H-imidazol-2-yl)-8,9-dihydro-2H-pyrido[4,3,2-de]phthalazin-3(7H)-one;

9-(1H-imidazol-2-yl)-8-phenyl-8,9-dihydro-2H-pyrido[4,3,2-de]phthalazin-3(7H)-one;

9-(1-ethyl-1H-imidazol-2-yl)-8-phenyl-8,9-dihydro-2H-pyrido[4,3,2-de]phthalazin-3(7H)-one;

8-phenyl-9-(1-propyl-1H-imidazol-2-yl)-8,9-dihydro-2H-pyrido[4,3,2-de]phthalazin-3(7H)-one;

9-(1-methyl-1H-imidazol-5-yl)-8-phenyl-8,9-dihydro-2H-pyrido[4,3,2-de]phthalazin-3(7H)-one;

9-(3-((diethylamino)methyl)phenyl)-8-(4-((diethylamino)methyl)phenyl)-8,9-dihydro-2H-pyrido[4,3,2-de]phthalazin-3(7H)-one;

9-(3-((4-methylpiperazin-1-yl)methyl)phenyl)-8-phenyl-8,9-dihydro-2H-pyrido[4,3,2-de]phthalazin-3(7H)-one;

8-(4-(4-(cyclopropanecarbonyl)piperazine-1-carbonyl)phenyl)-9-phenyl-8,9-dihydro-2H-pyrido[4,3,2-de]phthalazin-3(7H)-one;

9-phenyl-8-(pyridin-4-yl)-8,9-dihydro-2H-pyrido[4,3,2-de]phthalazin-3(7H)-one;

9-phenyl-8-(piperidin-4-yl)-8,9-dihydro-2H-pyrido[4,3,2-de]phthalazin-3(7H)-one;

9-phenyl-8-(pyridin-2-yl)-8,9-dihydro-2H-pyrido[4,3,2-de]phthalazin-3(7H)-one;

8-(4-((4-methylpiperazin-1-yl)methyl)phenyl)-9-phenyl-8,9-dihydro-2H-pyrido[4,3,2-de]phthalazin-3(7H)-one;

8,9-bis(4-fluorophenyl)-8,9-dihydro-2H-pyrido[4,3,2-de]phthalazin-3(7H)-one;

8-(4-((dimethylamino)methyl)phenyl)-9-(4-fluorophenyl)-8,9-dihydro-2H-pyrido[4,3,2-de]phthalazin-3(7H)-one;

8-(4-fluorophenyl)-9-(1-methyl-1H-imidazol-2-yl)-8,9-dihydro-2H-pyrido[4,3,2-de]phthalazin-3(7H)-one;

8,9-bis(3-((dimethylamino)methyl)phenyl)-8,9-dihydro-2H-pyrido[4,3,2-de]phthalazin-3(7H)-one;
9-(3-((cyclopropylamino)methyl)phenyl)-8-phenyl-8,9-dihydro-2H-pyrido[4,3,2-de]phthalazin-3(7H)-one;
8-(3-((dimethylamino)methyl)phenyl)-9-phenyl-8,9-dihydro-2H-pyrido[4,3,2-de]phthalazin-3(7H)-one;
8-(3-(morpholinomethyl)phenyl)-9-phenyl-8,9-dihydro-2H-pyrido[4,3,2-de]phthalazin-3(7H)-one;
8-(4-(azetidin-1-ylmethyl)phenyl)-9-(4-fluorophenyl)-8,9-dihydro-2H-pyrido[4,3,2-de]phthalazin-3(7H)-one;
5-fluoro-8-(4-fluorophenyl)-9-(1-methyl-1H-1,2,4-triazol-5-yl)-8,9-dihydro-2H-pyrido[4,3,2-de]phthalazin-3(7H)-one;
9-(1-methyl-1H-1,2,4-triazol-5-yl)-8-phenyl-8,9-dihydro-2H-pyrido[4,3,2-de]phthalazin-3(7H)-one;
8-(4-((dimethylamino)methyl)phenyl)-9-(1-methyl-1H-1,2,4-triazol-5-yl)-8,9-dihydro-2H-pyrido[4,3,2-de]phthalazin-3(7H)-one;
8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one;
8-(4-fluorophenyl)-9-methyl-9-(1-methyl-1H-1,2,4-triazol-5-yl)-8,9-dihydro-2H-pyrido[4,3,2-de]phthalazin-3(7H)-one;
8-(4-fluorophenyl)-9-(1,4,5-trimethyl-1H-imidazol-2-yl)-8,9-dihydro-2H-pyrido[4,3,2-de]phthalazin-3(7H)-one;
8-(4-fluorophenyl)-9-(1-methyl-1H-1,2,3-triazol-4-yl)-8,9-dihydro-2H-pyrido[4,3,2-de]phthalazin-3(7H)-one;
9-(4,5-dimethyl-4H-1,2,4-triazol-3-yl)-8-phenyl-8,9-dihydro-2H-pyrido[4,3,2-de]phthalazin-3(7H)-one;
9-(4,5-dimethyl-4H-1,2,4-triazol-3-yl)-8-(4-fluorophenyl)-8,9-dihydro-2H-pyrido[4,3,2-de]phthalazin-3(7H)-one;
8-(4-chlorophenyl)-9-(1-methyl-1H-imidazol-2-yl)-8,9-dihydro-2H-pyrido[4,3,2-de]phthalazin-3(7H)-one;
9-(1-methyl-1H-imidazol-2-yl)-8-(4-(trifluoromethyl)phenyl)-8,9-dihydro-2H-pyrido[4,3,2-de]phthalazin-3(7H)-one;
8-(4-fluorophenyl)-9-(thiazol-2-yl)-8,9-dihydro-2H-pyrido[4,3,2-de]phthalazin-3(7H)-one;
9-(1-ethyl-1H-imidazol-2-yl)-8-(4-fluorophenyl)-8,9-dihydro-2H-pyrido[4,3,2-de]phthalazin-3(7H)-one;
8-(4-((4-ethyl-3-methylpiperazin-1-yl)methyl)phenyl)-9-phenyl-8,9-dihydro-2H-pyrido[4,3,2-de]phthalazin-3(7H)-one;
8-(4-((4-ethylpiperazin-1-yl)methyl)phenyl)-9-(4-fluorophenyl)-8,9-dihydro-2H-pyrido[4,3,2-de]phthalazin-3(7H)-one;
9-(4-fluorophenyl)-8-(4-((4-methylpiperazin-1-yl)methyl)phenyl)-8,9-dihydro-2H-pyrido[4,3,2-de]phthalazin-3(7H)-one;
9-(4-fluorophenyl)-8-(4-(piperazin-1-ylmethyl)phenyl)-8,9-dihydro-2H-pyrido[4,3,2-de]phthalazin-3(7H)-one;
9-(4-fluorophenyl)-8-(4-((3-methylpiperazin-1-yl)methyl)phenyl)-8,9-dihydro-2H-pyrido[4,3,2-de]phthalazin-3(7H)-one;
9-(4-fluorophenyl)-8-(4-(pyrrolidin-1-ylmethyl)phenyl)-8,9-dihydro-2H-pyrido[4,3,2-de]phthalazin-3(7H)-one;
9-phenyl-8,9-dihydro-2H-pyrido[4,3,2-de]phthalazin-3(7H)-one;
8-(4-Fluorophenyl)-9-(4-methyl-4H-1,2,4-triazol-3-yl)-8,9-dihydro-2H-pyrido[4,3,2-de]phthalazin-3(7H)-one;
8-(4-fluorophenyl)-9-(1-methyl-1H-1,2,4-triazol-5-yl)-8,9-dihydro-2H-pyrido[4,3,2-de]phthalazin-3(7H)-one;
8-(4-fluorophenyl)-9-(1-methyl-1H-imidazo[4,5-c]pyridin-2-yl)-8,9-dihydro-2H-pyrido[4,3,2-de]phthalazin-3(7H)-one;
5-chloro-9-(1-methyl-1H-imidazol-2-yl)-8-phenyl-8,9-dihydro-2H-pyrido[4,3,2-de]phthalazin-3(7H)-one;
8-(4-((dimethylamino)methyl)phenyl)-5-fluoro-9-(4-fluorophenyl)-8,9-dihydro-2H-pyrido[4,3,2-de]phthalazin-3(7H)-one;
8,9-bis(4-((dimethylamino)methyl)phenyl)-5-fluoro-8,9-dihydro-2H-pyrido[4,3,2-de]phthalazin-3(7H)-one;
8-(4-((dimethylamino)methyl)phenyl)-5-fluoro-9-phenyl-8,9-dihydro-2H-pyrido[4,3,2-de]phthalazin-3(7H)-one;
8-(4-((3,4-dimethylpiperazin-1-yl)methyl)phenyl)-9-(4-fluorophenyl)-8,9-dihydro-2H-pyrido[4,3,2-de]phthalazin-3(7H)-one;
8-(4-((3,5-dimethylpiperazin-1-yl)methyl)phenyl)-9-(4-fluorophenyl)-8,9-dihydro-2H-pyrido[4,3,2-de]phthalazin-3(7H)-one;
9-phenyl-8-(4-(pyrrolidin-1-ylmethyl)phenyl)-8,9-dihydro-2H-pyrido[4,3,2-de]phthalazin-3(7H)-one;
9-phenyl-8-(4-(pyrrolidin-1-ylmethyl)phenyl)-8,9-dihydro-2H-pyrido[4,3,2-de]phthalazin-3(7H)-one;
9-(1-methyl-1H-imidazol-2-yl)-8-(4-(pyrrolidin-1-ylmethyl)phenyl)-8,9-dihydro-2H-pyrido[4,3,2-de]phthalazin-3(7H)-one;
9-(4-fluorophenyl)-8-(1-methyl-1H-imidazol-2-yl)-8,9-dihydro-2H-pyrido[4,3,2-de]phthalazin-3(7H)-one;
9-(4-fluorophenyl)-8-(quinolin-6-yl)-8,9-dihydro-2H-pyrido[4,3,2-de]phthalazin-3(7H)-one;
8-(4-((dimethylamino)methyl)phenyl)-9-p-tolyl-8,9-dihydro-2H-pyrido[4,3,2-de]phthalazin-3(7H)-one;
9-(4-chlorophenyl)-8-(4-((dimethylamino)methyl)phenyl)-8,9-dihydro-2H-pyrido[4,3,2-de]phthalazin-3(7H)-one;
8-(4-((dimethylamino)methyl)phenyl)-9-(4-methoxyphenyl)-8,9-dihydro-2H-pyrido[4,3,2-de]phthalazin-3(7H)-one;
8-(4-((diethylamino)methyl)phenyl)-9-phenyl-8,9-dihydro-2H-pyrido[4,3,2-de]phthalazin-3(7H)-one;
8-(4-((diethylamino)methyl)phenyl)-9-(4-fluorophenyl)-8,9-dihydro-2H-pyrido[4,3,2-de]phthalazin-3(7H)-one;
9-(4-chlorophenyl)-8-(4-((diethylamino)methyl)phenyl)-8,9-dihydro-2H-pyrido[4,3,2-de]phthalazin-3(7H)-one;
(E)-6-fluoro-4-((1-methyl-1H-imidazol-2-yl)methyleneamino)isobenzofuran-1(3H)-one;
5-fluoro-9-(4-fluorophenyl)-8-(1-methyl-1H-imidazol-2-yl)-8,9-dihydro-2H-pyrido[4,3,2-de]phthalazin-3(7H)-one;
8-(4-((dimethylamino)methyl)phenyl)-9-(4-ethylphenyl)-8,9-dihydro-2H-pyrido[4,3,2-de]phthalazin-3(7H)-one;
8-(4-((dimethylamino)methyl)phenyl)-9-(4-isopropylphenyl)-8,9-dihydro-2H-pyrido[4,3,2-de]phthalazin-3(7H)-one;
8-(4-((dimethylamino)methyl)phenyl)-9-(4-(trifluoromethyl)phenyl)-8,9-dihydro-2,1-pyrido[4,3,2-de]phthalazin-3(7H)-one;
8-(4-((diethylamino)methyl)phenyl)-9-p-tolyl-8,9-dihydro-2H-pyrido[4,3,2-de]phthalazin-3(7H)-one;
9-(4-fluorophenyl)-8-(4-(1-methylpyrrolidin-2-yl)phenyl)-8,9-dihydro-2H-pyrido[4,3,2-de]phthalazin-3(7H)-one;
9-(4-fluorophenyl)-8-(4-(pyrrolidin-2-yl)phenyl)-8,9-dihydro-2H-pyrido[4,3,2-de]phthalazin-3(7H)-one;
8-(4-fluorophenyl)-9-methyl-9-(1-methyl-1H-imidazol-2-yl)-8,9-dihydro-2H-pyrido[4,3,2-de]phthalazin-3(7H)-one;
9-(4-fluorophenyl)-8-(1H-imidazol-2-yl)-8,9-dihydro-2H-pyrido[4,3,2-de]phthalazin-3(7H)-one;
5-fluoro-9-(1-methyl-1H-1,2,4-triazol-5-yl)-8-phenyl-8,9-dihydro-2H-pyrido[4,3,2-de]phthalazin-3(7H)-one;

9-(4-fluorophenyl)-9-hydroxy-8-(1-methyl-1H-imidazol-2-yl)-8,9-dihydro-2H-pyrido[4,3,2-de]phthalazin-3(7H)-one;

(8S,9R)-5-fluoro-9-(1-methyl-1H-imidazol-2-yl)-8-phenyl-8,9-dihydro-2H-pyrido[4,3,2-de]phthalazin-3(7H)-one;

(8R,9S)-5-fluoro-9-(1-methyl-1H-imidazol-2-yl)-8-phenyl-8,9-dihydro-2H-pyrido[4,3,2-de]phthalazin-3(7H)-one;

(8S,9R)-5-fluoro-8-(4-fluorophenyl)-9-(1-methyl-1H-imidazol-2-yl)-8,9-dihydro-2H-pyrido[4,3,2-de]phthalazin-3(7H)-one;

(8R,9S)-5-fluoro-8-(4-fluorophenyl)-9-(1-methyl-1H-imidazol-2-yl)-8,9-dihydro-2H-pyrido[4,3,2-de]phthalazin-3(7H)-one;

(8S,9R)-8-(4-fluorophenyl)-9-(1-methyl-1H-imidazol-2-yl)-8,9-dihydro-2H-pyrido[4,3,2-de]phthalazin-3(7H)-one;

(8R,9S)-8-(4-fluorophenyl)-9-(1-methyl-1H-imidazol-2-yl)-8,9-dihydro-2H-pyrido[4,3,2-de]phthalazin-3(7H)-one;

(8S,9R)-5-fluoro-9-(1-methyl-1H-1,2,4-triazol-5-yl)-8-phenyl-8,9-dihydro-2H-pyrido[4,3,2-de]phthalazin-3(7H)-one;

(8R,9S)-5-fluoro-9-(1-methyl-1H-1,2,4-triazol-5-yl)-8-phenyl-8,9-dihydro-2H-pyrido[4,3,2-de]phthalazin-3(7H)-one;

(8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one;

(8R,9S)-5-fluoro-8-(4-fluorophenyl)-9-(1-methyl-1H-1,2,4-triazol-5-yl)-8,9-dihydro-2H-pyrido[4,3,2-de]phthalazin-3(7H)-one;

(8S,9R)-8-(4-fluorophenyl)-9-(1-methyl-1H-1,2,4-triazol-5-yl)-8,9-dihydro-2H-pyrido[4,3,2-de]phthalazin-3(7H)-one;

(8R,9S)-8-(4-fluorophenyl)-9-(1-methyl-1H-1,2,4-triazol-5-yl)-8,9-dihydro-2H-pyrido[4,3,2-de]phthalazin-3(7H)-one;

(8S,9R)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one; and (8R,9S)-8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one;

or a pharmaceutical acceptable salt, solvate or prodrug therefore.

In some embodiments, provided herein is a pharmaceutical composition comprising of a compound of Formula (I), (IA) or (II) or stereoisomers, or a pharmaceutically acceptable salt, a pharmaceutically acceptable solvate, pharmaceutically acceptable prodrug thereof and a pharmaceutically acceptable carrier, excipient, binder or diluent.

Certain embodiments provide a method of inhibiting PARP in a subject having a disease, disorder, or condition associated with a PTEN deficiency recognized to be in need of such treatment comprising administering to the subject a therapeutically acceptable amount of a compound of Formula (I), (IA) or (II) or a therapeutically acceptable salt thereof.

In one aspect is a method of inhibiting poly(ADP-ribose) polymerase (PARP) in a subject having a disease, disorder, or condition associated with a PTEN deficiency comprising administering to the subject a therapeutically effective amount of a compound of Formula (I), (IA) or Formula (II).

In still another aspect is a method of treating a disease, disorder or condition associated with a PTEN deficiency which is ameliorated by the inhibition of PARP comprising administering to a subject in need of treatment a therapeutically effective amount of a compound of Formula (I), (IA) or Formula (II). In certain embodiments, the disease, disorder or condition is related to Cowden Syndrome. In other embodiments, the disease, disorder or condition is related to Bannayan-Riley-Ruvalcaba syndrome. In still other embodiments, the disease, disorder or condition is Lhermitte-Duclos disease.

In certain aspects, provided herein are methods for the treatment of a cancer associated with a PTEN deficiency, comprising administering to a subject in need of treatment a therapeutically-effective amount of a compound of Formula (I), (IA) or (II). In certain embodiments, the cancer cells have a PTEN deficient phenotype. In certain embodiments, the cancer is endometrial carcinoma, glioblastoma (glioblastoma multiforme/anaplastic astrocytoma), prostate cancer, renal cancer, small cell lung carcinoma, meningioma, head and neck cancer, thyroid cancer, bladder cancer, colorectal cancer, breast cancer or melanoma.

In certain other aspects, provided herein are methods of treating a cancer associated with a PTEN deficiency wherein one or more cancer cells have an abrogated or reduced ability to control the phosphoinositide 3-kinase signaling pathway, comprising administering to a subject in need of treatment a therapeutically effective amount of a compound of Formula (I), (IA) or Formula (II). In certain embodiments, the cancer comprises one or more cancer cells having a reduced or abrogated ability to control the phosphoinositide 3-kinase signaling pathway for regulation of cell growth relative to normal cells.

In yet another aspect is a method of treating a cancer associated with a PTEN deficiency wherein one or more cancer cells is deficient in Homologous Recombination (HR) dependent DNA double strand break (DSB) repair pathway, comprising administering to a subject in need of treatment a therapeutically effective amount of a compound of Formula (I), (IA) or Formula (II). In certain embodiments the cancer comprises one or more cancer cells having a reduced or abrogated ability to repair DNA DSB by HR relative to normal cells. In a further embodiment the subject is heterozygous for a mutation in a gene encoding a component of the HR dependent DNA DSB repair pathway. In certain embodiments, one or more cancer cells have a RAD51 deficient phenotype. In yet another embodiment, the cancer cells are deficient in RAD51. In yet another embodiment, the subject is heterozygous for a mutation in RAD51. In another embodiment, the cancer cells have a BRCA1 or BRCA2 deficient phenotype. In yet another embodiment, the cancer cells are deficient in BRCA1 or BRCA2. In yet another embodiment, the subject is heterozygous for a mutation in BRCA1 and/or BRCA2. In yet a further embodiment the subject is heterozygous for a mutation in PTEN.

In some embodiments, the method of treatment of a cancer includes treatment of endometrial carcinoma, glioblastoma (glioblastoma multiforme/anaplastic astrocytoma), prostate cancer, renal cancer, small cell lung carcinoma, meningioma, head and neck cancer, thyroid cancer, bladder cancer, colorectal cancer, breast cancer or melanoma. In some embodiments, the method of treatment of a cancer further includes administration of ionizing radiation or a chemotherapeutic agent.

In some embodiments, provided herein is a method for the treatment of a cancer associated with a PTEN deficiency, comprising administering to a subject in need of treatment a therapeutically-effective amount of a compound of Formula (I), (IA) or (II) in combination with ionizing radiation or one or more chemotherapeutic agents. In some embodiments, the compound described herein is administered simultaneously with ionizing radiation or one or more chemotherapeutic agents. In other embodiments, the compound described herein is administered sequentially with ionizing radiation or one or more chemotherapeutic agents.

In one embodiment the compound of Formula (I), (IA) or Formula (II) is administered simultaneously with ionizing radiation, one or more chemotherapeutic agents, or a combination thereof. In another embodiment the compound of Formula (I), (IA) or Formula (II) is administered sequentially with ionizing radiation, one or more chemotherapeutic agents, or a combination thereof.

In one aspect is the use of a compound of Formula (I), (IA) or Formula (II) in the formulation of a medicament for the treatment of a poly(ADP-ribose)polymerase mediated disease or condition associated with a PTEN deficiency.

Certain embodiments provide a method of potentiation of cytotoxic cancer therapy in a subject in recognized need of such treatment comprising administering to the subject a therapeutically acceptable amount of a compound of Formula (I), (IA) or (II) or a therapeutically acceptable salt thereof. Certain embodiments provide a method of treating endometrial carcinoma, glioblastoma (glioblastoma multiforme/anaplastic astrocytoma), prostate cancer, renal cancer, small cell lung carcinoma, meningioma, head and neck cancer, thyroid cancer, bladder cancer, colorectal cancer, breast cancer or melanoma in a subject in recognized need of such treatment comprising administering to the subject a therapeutically acceptable amount of a compound of Formula (I), (IA) or (II) or therapeutically acceptable salt thereof.

Certain embodiments provide a use of a compound of Formula (I), (IA) or (II) or a therapeutically acceptable salt thereof, to prepare a medicament for inhibiting the PARP enzyme in a subject having a disease or disorder associated with a PTEN deficiency recognized to be in need of such treatment.

Certain embodiments provide a use of a compound of Formula (I), (IA) or (II) or a therapeutically acceptable salt thereof, to prepare a medicament for inhibiting tumor growth in a subject having a disease or disorder associated with a PTEN deficiency recognized to be in need of such treatment.

Certain embodiments provide a use of a compound of Formula (I), (IA) or (II) or a therapeutically acceptable salt thereof, to prepare a medicament for treating cancer in a subject having a disease or disorder associated with a PTEN deficiency recognized to be in need of such treatment.

Certain embodiments provide a use of a compound of Formula (I), (IA) or (II) or a therapeutically acceptable salt thereof, to prepare a medicament for treating certain cancers including, but not limited to, endometrial carcinoma, glioblastoma (glioblastoma multiforme/anaplastic astrocytoma), prostate cancer, renal cancer, small cell lung carcinoma, meningioma, head and neck cancer, thyroid cancer, bladder cancer, colorectal cancer, breast cancer or melanoma in a subject in recognized need of such treatment.

Certain embodiments provide a use of a compound of Formula (I), (IA) or (II) or a therapeutically acceptable salt thereof, to prepare a medicament for potentiation of cytotoxic cancer therapy in a subject in recognized need of such treatment comprising administering to the subject a therapeutically acceptable amount of a compound of Formula (I), (IA) or (II) or a therapeutically acceptable salt thereof.

Articles of manufacture, comprising packaging material, a compound provided herein that is effective for modulating the activity of the enzyme poly(ADP-ribose)polymerase, or for treatment, prevention or amelioration of one or more symptoms of a disease or condition associated with a PTEN deficiency, wherein the compound is packaged within the packaging material, and wherein the label indicates that the compound, or pharmaceutically acceptable salt, pharmaceutically acceptable N-oxide, pharmaceutically active metabolite, pharmaceutically acceptable prodrug, or pharmaceutically acceptable solvate thereof, or a pharmaceutical composition comprising such a compound is used for modulating the activity of poly(ADP-ribose)polymerase, or for treatment, prevention or amelioration of one or more symptoms of a disease or condition associated with a PTEN deficiency are provided.

Any combination of the groups described above for the various variables is contemplated herein.

In one embodiment, disclosed herein is a pharmaceutical composition comprising a compound, pharmaceutically acceptable salt, pharmaceutically acceptable N-oxide, pharmaceutically active metabolite, pharmaceutically acceptable prodrug, or pharmaceutically acceptable solvate of any of the compounds disclosed herein. In some embodiments, the pharmaceutical compositions further comprises a pharmaceutically acceptable diluent, excipient or binder. In certain embodiments, the pharmaceutical composition further comprises a second pharmaceutically active ingredient.

In one embodiment, the disease or condition associated with a PTEN deficiency in a patient, or the PTEN-deficient dependent disease or condition in a patient is cancer or a non-cancerous disorder. In some embodiments, the disease or condition is iatrogenic.

In some embodiments are methods for reducing/inhibiting the activity of PARP in a subject having a disease or disorder associated with a PTEN deficiency that include administering to the subject at least once an effective amount of a compound described herein.

Certain embodiments provided herein are methods for modulating, including reducing and/or inhibiting the activity of PARP, directly or indirectly, in a subject having a disease or disorder associated with a PTEN deficiency comprising administering to the subject at least once an effective amount of at least one compound described herein.

In further embodiments are methods for treating diseases or conditions associated with a PTEN deficiency, comprising administering to the subject at least once an effective amount of at least one compound described herein.

Some embodiments include the use of a compound described herein in the manufacture of a medicament for treating a disease or condition associated with a PTEN deficiency in a subject in which the PTEN deficiency contributes to the pathology and/or symptoms of the disease or condition.

In any of the aforementioned embodiments are further embodiments in which administration is enteral, parenteral, or both, and wherein:
(a) the effective amount of the compound is systemically administered to the subject;
(b) the effective amount of the compound is administered orally to the subject;
(c) the effective amount of the compound is intravenously administered to the subject;
(d) the effective amount of the compound administered by inhalation;
(e) the effective amount of the compound is administered by nasal administration;
(f) the effective amount of the compound is administered by injection to the subject;
(g) the effective amount of the compound is administered topically (dermal) to the subject;
(h) the effective amount of the compound is administered by ophthalmic administration; and/or
(i) the effective amount of the compound is administered rectally to the subject.

In any of the aforementioned embodiments are further embodiments that include single administrations of the effective amount of the compound, including further embodiments in which the compound is administered to the subject (i) once; (ii) multiple times over the span of one day; (iii) continually; or (iv) continuously.

In any of the aforementioned embodiments are further embodiments that include multiple administrations of the effective amount of the compound, including further embodiments wherein:
(i) the compound is administered in a single dose;
(ii) the time between multiple administrations is every 6 hours;
(iii) the compound is administered to the subject every 8 hours.

In further or alternative embodiments, the method includes a drug holiday, wherein the administration of the compound is temporarily suspended or the dose of the compound being administered is temporarily reduced; at the end of the drug holiday, dosing of the compound is resumed. In some embodiments, the length of the drug holiday varies from 2 days to 1 year.

In any of the aforementioned embodiments involving the treatment of proliferative disorders, including cancer, are further embodiments that include administering at least one additional agent selected from among alemtuzumab, arsenic trioxide, asparaginase (pegylated or non-), bevacizumab, cetuximab, trastuzumab, platinum-based compounds such as cisplatin, cladribine, daunorubicin/doxorubicin/idarubicin, irinotecan, fludarabine, 5-fluorouracil, gemcitabine, toptecan, cyclophosphamide, gemtuzumab, methotrexate, paclitaxel (Taxol®), temozolomide, thioguanine, and classes of drugs including hormones (an antiestrogen, an antiandrogen, or gonadotropin releasing hormone analogues, interferons such as, for example, alpha interferon, nitrogen mustards such as, for example, busulfan, melphalan or mechlorethamine, retinoids such as, for example, tretinoin, topoisomerase inhibitors such as, for example, irinotecan or topotecan, tyrosine kinase inhibitors such as, for example, gefitinib, erlotinib or imatinib, mTOR inhibitors such as, for example temsirolimus or everolimus and agents to treat signs or symptoms induced by such therapy including allopurinol, filgrastim, granisetron/ondansetron/palonosetron, and/or dronabinol.

Other objects, features and advantages of the compounds, methods and compositions described herein will become apparent from the following description. It should be understood, however, that the description and the specific examples, while indicating specific embodiments, are given by way of illustration only, since various changes and modifications within the spirit and scope of the present description will become apparent from this detailed description.

Described herein are compounds, methods of making such compounds, pharmaceutical compositions and medicaments that include such compounds, and methods of using such compounds to treat or prevent diseases or conditions associated with a PTEN deficiency.

In certain embodiments, PARP inhibitors, such as those of Formula (I), (IA) or (II), have utility in: (a) preventing or inhibiting poly(ADP-ribose) chain formation by, e.g., inhibiting the activity of cellular PARP (PARP-1 and/or PARP-2); (b) treating diseases or conditions associated with PTEN deficiency including, but not limited to, Cowden's Syndrome, Lhermitte-Duclos disease or Bannayan-Riley-Ruvalcaby syndrome; cancer or other proliferative disorders including, but not limited to, glioblastoma, endometrial carcinoma, melanoma, prostate cancer, colorectal cancer, breast cancer, and bladder cancers; (c) use as an adjunct in cancer therapy or for potentiating tumor cells for treatment with ionizing radiation and/or chemotherapeutic agents.

In specific embodiments, compounds provided herein, such as, for example, Formula (I), (IA) or (II), are used in anti-cancer combination therapies (or as adjuncts) along with alkylating agents, such as methyl methanesulfonate (MMS), temozolomide and dacarbazine (DTIC), also with topoisomerase-1 inhibitors like Topotecan, Irinotecan, Rubitecan, Exatecan, Lurtotecan, Gimetecan, Diflomotecan (homocamptothecins); as well as 7-substituted non-silatecans; the 7-silyl camptothecins, BNP 1350; and non-camptothecin topoisomerase-I inhibitors such as indolocarbazoles also dual topoisomerase-I and II inhibitors like the benzophenazines, XR 11576/MLN 576 and benzopyridoindoles. In certain embodiments, such combinations are given, for example, as intravenous preparations or by oral administration as dependent on the method of administration for the particular agent.

In some embodiments, PARP inhibitors, such as, for example, compounds of Formula (I), (IA) or (II), are used in the treatment of disease or disorder associated with a PTEN deficiency ameliorated by the inhibition of PARP, which includes administering to a subject in need of treatment a therapeutically-effective amount of a compound provided herein, and in one embodiment in the form of a pharmaceutical composition. In certain embodiments, PARP inhibitors, such as, for example, compounds of Formula (I), (IA) or (II), are used in the treatment of cancer, which includes administering to a subject in need of treatment a therapeutically-effective amount of a compound provided herein in combination, and in one embodiment in the form of a pharmaceutical composition, simultaneously or sequentially with radiotherapy (ionizing radiation) or chemotherapeutic agents.

In certain embodiments, PARP inhibitors, such as, for example, compounds of Formula (I), (IA) or (II), are used in the preparation of a medicament for the treatment of cancer associated with a PTEN deficiency which is deficient in Homologous Recombination (HR) dependent DNA double strand break (DSB) repair activity, or in the treatment of a patient with a cancer which is deficient in HR dependent DNA DSB repair activity, which includes administering to said patient a therapeutically-effective amount of the compound.

The HR dependent DNA DSB repair pathway repairs double-strand breaks (DSBs) in DNA via homologous mechanisms to reform a continuous DNA helix. The components of the HR dependent DNA DSB repair pathway include, but are not limited to, ATM (NM_000051), RAD51 (NM_002875), RADS ILI (NM_002877), RAD51C(NM_002876), RAD51L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11A (NM_005590) and NBS1 (NM_002485). Other proteins involved in the HR dependent DNA DSB repair pathway include regulatory factors such as EMSY. HR components are also described in Wood, et al., *Science*, 291, 1284-1289 (2001), which is hereby incorporated by reference for such disclosure. K. K. Khanna and S. P. Jackson, *Nat. Genet.* 27(3): 247-254 (2001); and Hughes-Davies, et al., *Cell*, 115, pp 523-535 are also incorporated herein by reference for such disclosure.

In some embodiments, a cancer associated with a PTEN deficiency which is deficient in HR dependent DNA DSB repair includes one or more cancer cells which have a reduced or abrogated ability to repair DNA DSBs through that pathway, relative to normal cells, i.e. the activity of the HR dependent DNA DSB repair pathway are reduced or abolished in the one or more cancer cells.

In certain embodiments, the activity of one or more components of the HR dependent DNA DSB repair pathway is abolished in the one or more cancer cells of an individual having a cancer which is deficient in HR dependent DNA DSB repair. Components of the HR dependent DNA DSB repair pathway include the components listed above.

In some embodiments, the cancer cells have a PTEN deficient phenotype, i.e., PTEN activity is reduced or abolished in the cancer cells. In certain embodiments, cancer cells with this phenotype are deficient in PTEN, i.e., expression and/or activity of PTEN is reduced or abolished in the cancer cells, for example by means of mutation or polymorphism in the encoding nucleic acid, or by means of amplification, mutation or polymorphism in a gene encoding a regulatory factor specific for PTEN.

In some embodiments, the cancer cells have a BRCA1 and/or a BRCA2 deficient phenotype, i.e., BRCA1 and/or BRCA2 activity is reduced or abolished in the cancer cells. In certain embodiments, cancer cells with this phenotype are deficient in BRCA1 and/or BRCA2, i.e., expression and/or activity of BRCA1 and/or BRCA2 is reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor or by an epigenetic mechanism such as gene promoter methylation.

In certain instances, mutations and polymorphisms associated with cancer are detected at the nucleic acid level by detecting the presence of a variant nucleic acid sequence or at the protein level by detecting the presence of a variant (i.e. a mutant or allelic variant) polypeptide.

DEFINITIONS

Unless defined otherwise, all technical and scientific terms used herein have the standard meaning pertaining to the claimed subject matter belongs. In the event that there is a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Unless otherwise indicated, conventional methods of mass spectroscopy, NMR, HPLC, protein chemistry, biochemistry, recombinant DNA techniques and pharmacology are employed. Unless specific definitions are provided, the standard nomenclature employed in connection with, and the standard laboratory procedures and techniques of, analytical chemistry, synthetic organic chemistry, and medicinal and pharmaceutical chemistry are employed. In certain instances, standard techniques are used for chemical syntheses, chemical analyses, pharmaceutical preparation, formulation, and delivery, and treatment of patients. In certain embodiments, standard techniques are used for recombinant DNA, oligonucleotide synthesis, and tissue culture and transformation (e.g., electroporation, lipofection). In some embodiments, reactions and purification techniques are performed e.g., using kits of manufacturer's specifications or as commonly accomplished or as described herein.

As used throughout this application and the appended claims, the following terms have the following meanings:

The term "alkenyl" as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. In some embodiments, depending on the structure, an alkenyl group is a monoradical or a diradical (i.e., an alkenylene group). In some embodiments, alkenyl groups are optionally substituted. Illustrative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-cecenyl.

The term "alkoxy" as used herein, means an alkyl group, as defined herein, appended to the parent molecular moiety through an oxygen atom. Illustrative examples of alkoxy include, but are not limited to, methoxy, ethoxy, propoxy, 2-propoxy, butoxy, tert-butoxy, pentyloxy, and hexyloxy.

The term "alkyl" as used herein, means a straight, branched chain, or cyclic (in this case, it would also be known as "cycloalkyl") hydrocarbon containing from 1-10 carbon atoms. Illustrative examples of alkyl include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl.

The term "$C_1$-$C_6$-alkyl" as used herein, means a straight, branched chain, or cyclic (in this case, it would also be known as "cycloalkyl") hydrocarbon containing from 1-6 carbon atoms. Representative examples of alkyl include, but are not limited to, methyl, ethyl, n-propyl, iso-propyl, cyclopyl, n-butyl, sec-butyl, tert-butyl, cyclobutyl, n-pentyl, isopentyl, neopentyl, cyclopentyl, and n-hexyl.

The term "cycloalkyl" as used herein, means a monocyclic or polycyclic radical that contains only carbon and hydrogen, and includes those that are saturated, partially unsaturated, or fully unsaturated. Cycloalkyl groups include groups having from 3 to 10 ring atoms. Representative examples of cyclic include but are not limited to, the following moieties:

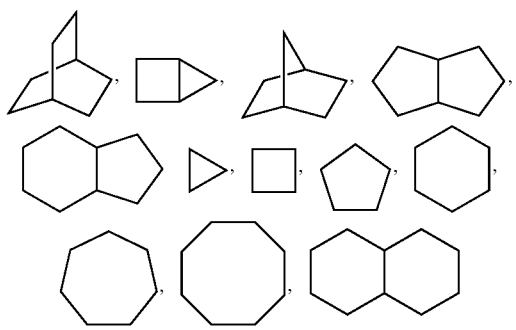

-continued

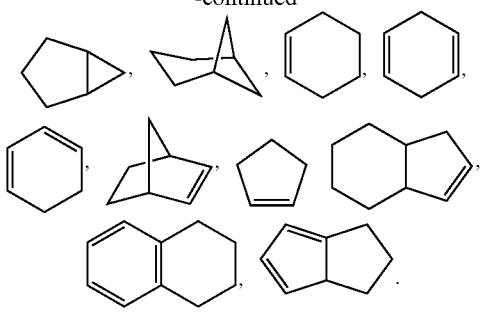

In some embodiments, depending on the structure, a cycloalkyl group is a monoradical or a diradical (e.g., a cycloalkylene group).

The term "cycloalkyl groups" as used herein refers to groups which are optionally substituted with 1, 2, 3, or 4 substituents selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxyl, hydroxyalkylene, mercapto, oxo, —$NR_A R_A$, and ($NR_A R_B$)carbonyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "carbocyclic" as used herein, refers to a compound which contains one or more covalently closed ring structures, and that the atoms forming the backbone of the ring are all carbon atoms.

The term "carbocycle" as used herein, refers to a ring, wherein each of the atoms forming the ring is a carbon atom. Carbocylic rings include those formed by three, four, five, six, seven, eight, nine, or more than nine carbon atoms. Carbocycles are optionally substituted.

The term "alkoxyalkyl" as used herein, means at least one alkoxy group, as defined herein, appended to the parent molecular moiety through an alkyl group, as defined herein. Illustrative examples of alkoxyalkyl include, but are not limited to, 2-methoxyethyl, 2-ethoxyethyl, tert-butoxyethyl and methoxymethyl.

The term "alkoxycarbonyl" as used herein, means an alkoxy group, as defined herein, appended to the parent molecular moiety through a carbonyl group, as defined herein. Illustrative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein.

The term "alkylcarbonyl" as used herein, means an alkyl group, as defined herein, appended to the parent molecular moiety through a carbonyl group, as defined herein. Illustrative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Illustrative examples of alkylcarbonyloxy include, but are not limited to, acetyloxy, ethylcarbonyloxy, and tert-butylcarbonyloxy.

The term "alkylthio" or "thioalkoxy" as used herein, means an alkyl group, as defined herein, appended to the parent molecular moiety through a sulfur atom. Illustrative examples of alkylthio include, but are not limited to, methylthio, ethylthio, butylthio, tert-butylthio, and hexylthio.

The term "alkylthioalkyl" as used herein, means an alkylthio group, as defined herein, appended to the parent molecular moiety through an alkyl group, as defined herein. Illustrative examples of alkylthioalkyl include, but are not limited to, methylthiomethyl, 2-(ethylthio)ethyl, butylthiomethyl, and hexylthioethyl.

The term "alkynyl" as used herein, means a straight, branched chain hydrocarbon containing from 2-10 carbons and containing at least one carbon-carbon triple bond. In some embodiments, alkynyl groups are optionally substituted. Illustrative examples of alkynyl include, but are not limited to, acetylenyl, 1-propynyl, 2-propynyl, 3-butynyl, 2-pentynyl, and 1-butynyl.

The term "aromatic" as used herein, refers to a planar ring having a delocalized π-electron system containing 4n+2π electrons, where n is an integer. In some embodiments, aromatic rings are formed by five, six, seven, eight, nine, or more than nine atoms. In other embodiments, aromatics are optionally substituted. The term includes monocyclic or fused-ring polycyclic (i.e., rings which share adjacent pairs of carbon atoms) groups.

The term "aryl" as used herein, refers to an aromatic ring wherein each of the atoms forming the ring is a carbon atom. In some embodiments, aryl rings are formed by five, six, seven, eight, nine, or more than nine carbon atoms. Examples of aryl groups include, but are not limited to phenyl, naphthalenyl, phenanthrenyl, anthracenyl, fluorenyl, and indenyl.

In some embodiments, the term "aryl" as used herein means an aryl group that is optionally substituted with one, two, three, four or five substituents independently selected from the group consisting of alkenyl, alkoxy, alkoxyalkyl, alkoxycarbonyl, alkyl, alkylcarbonyl, alkylcarbonyloxy, alkylthio, alkylthioalkyl, alkynyl, carbonyl, cyano, formyl, haloalkoxy, haloalkyl, halogen, hydroxyl, hydroxyalkylene, mercapto, nitro, —$NR_A R_A$, and ($NR_A R_B$)carbonyl.

The term "arylalkyl" as used herein, means an aryl group, as defined herein, appended to the parent molecular moiety through an alkyl group, as defined herein. Illustrative examples of arylalkyl include, but are not limited to benzyl, 2-phenylethyl, -phenylpropyl, 1-methyl-3-phenylpropyl, and 2-naphth-2-ylethyl.

The term "carbonyl" as used herein, means a —C(O)— group.

The term "carboxy" as used herein, means a —COOH group.

The term "cyano" as used herein, means a —CN group.

The term "formyl" as used herein, means a —C(O)H group.

The term "halo" or "halogen" as used herein, means a —Cl, —Br, —I or —F.

The term "mercapto" as used herein, means a —SH group.

The term "nitro" as used herein, means a —$NO_2$ group.

The term "hydroxy" as used herein, means a —OH group.

The term "oxo" as used herein, means a =O group.

The term "bond" or "single bond" as used herein, refers to a chemical bond between two atoms, or two moieties when the atoms joined by the bond are considered to be part of larger substructure.

The terms "haloalkyl," "haloalkenyl," "haloalkynyl" and "haloalkoxy" as used herein, include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another. The terms "fluoroalkyl" and "fluoroalkoxy" include haloalkyl and haloalkoxy groups, respectively, in which the halo is fluorine. In certain embodiments, haloalkyls are optionally substituted.

The term "alkylamine" refers to the —N(alkyl)$_x$H$_y$ group, where x and y are selected from among x=1, y=1 and x=2, y=0. In some embodiments, when x=2, the alkyl groups, taken together with the N atom to which they are attached, optionally form a cyclic ring system.

The term "amide" as used herein, is a chemical moiety with the formula —C(O)NHR or —NHC(O)R, where R is selected from among hydrogen, alkyl, cycloalkyl, aryl, heteroaryl (bonded through a ring carbon) and heterocycloalkyl (bonded through a ring carbon). In some embodiments, an amide moiety forms a linkage between an amino acid or a peptide molecule and a compound described herein, thereby forming a prodrug. In some embodiments, any amine, or carboxyl side chain on the compounds described herein is amidified.

The term "ester" refers to a chemical moiety with formula —COOR, where R is selected from among alkyl, cycloalkyl, aryl, heteroaryl (bonded through a ring carbon) and heterocycloalkyl (bonded through a ring carbon). In some embodiments, any hydroxy, or carboxyl side chain on the compounds described herein is esterified.

The terms "heteroalkyl" "heteroalkenyl" and "heteroalkynyl" as used herein, include optionally substituted alkyl, alkenyl and alkynyl radicals in which one or more skeletal chain atoms are selected from an atom other than carbon, e.g., oxygen, nitrogen, sulfur, silicon, phosphorus or combinations thereof.

The term "heteroatom" as used herein refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms are all the same as one another, or some or all of the two or more heteroatoms are each different from the others.

The term "ring" as used herein, refers to any covalently closed structure. Rings include, for example, carbocycles (e.g., aryls and cycloalkyls), heterocycles (e.g., heteroaryls and heterocycloalkyls), aromatics (e.g. aryls and heteroaryls), and non-aromatics (e.g., cycloalkyls and heterocycloalkyls). In some embodiments, rings are optionally substituted. In some embodiments, rings form part of a ring system.

As used herein, the term "ring system" refers to two or more rings, wherein two or more of the rings are fused. The term "fused" refers to structures in which two or more rings share one or more bonds.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. In some embodiments, the polycyclic heteroaryl group is fused or non-fused. Illustrative of heteroaryl groups include, but are not limited to, the following moieties:

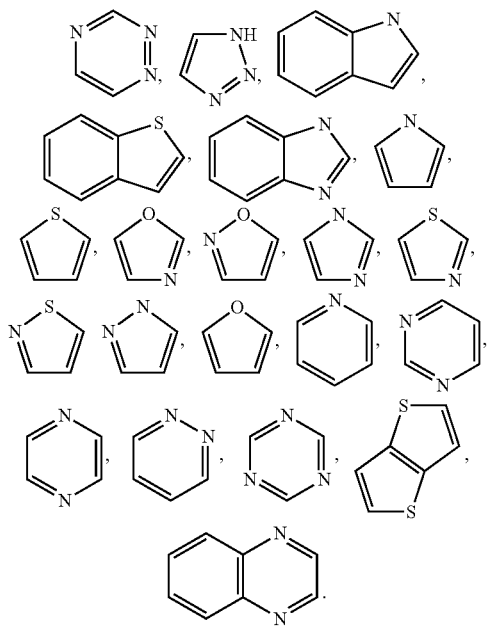

In some embodiments, depending on the structure, a heteroaryl group is a monoradical or a diradical (i.e., a heteroarylene group).

The term "heteroaryl" means heteroaryl groups that are substituted with 0, 1, 2, 3, or 4 substituents independently selected from alkenyl, alkoxy, alkoxyalkyl, alkoxycarbonyl, alkyl, alkylcarbonyl, alkylcarbonyloxy, alkylthio, alkylthioalkyl, alynyl, carboxy, cyano, formyl, haloalkoxy, haloalkyl, halogen, hydroxyl, hydroxyalkylene, mercapto, nitro, —NR$_A$R$_B$, and —(NR$_A$R$_B$)carbonyl.

The term "heteroarylalkyl" as used herein, means a heteroaryl, as defined herein, appended to the parent molecular moiety through an alkyl group, as defined herein. Illustrative examples of heteroarylalkyl include, but are not limited to, pyridinylmethyl.

The term "heterocycloalkyl" or "non-aromatic heterocycle" as used herein, refers to a non-aromatic ring wherein one or more atoms forming the ring is a heteroatom. A "heterocycloalkyl" or "non-aromatic heterocycle" group refers to a cycloalkyl group that includes at least one heteroatom selected from nitrogen, oxygen and sulfur. In some embodiments, the radicals are fused with an aryl or heteroaryl. In some embodiments, heterocycloalkyl rings are formed by three, four, five, six, seven, eight, nine, or more than nine atoms. In some embodiments, heterocycloalkyl rings are optionally substituted. In certain embodiments, heterocycloalkyls contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include, but are not limited to

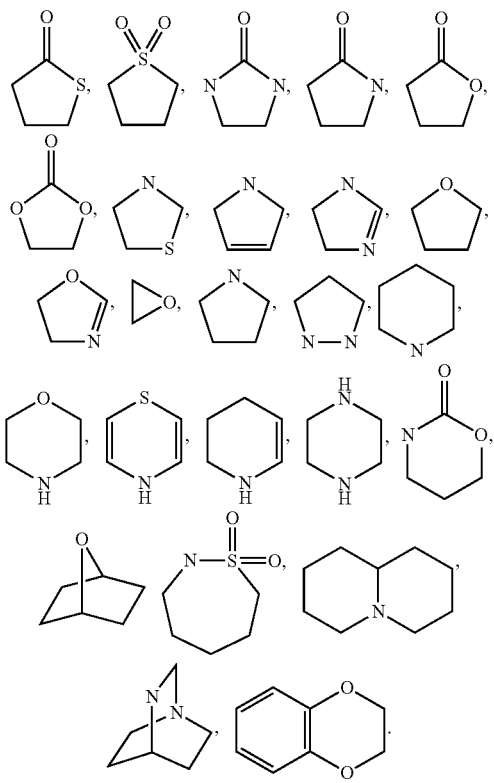

The term heterocycloalkyl also includes all ring forms of the carbohydrates, including but not limited to the monosaccharides, the disaccharides and the oligosaccharides.

The term "heterocycle" refers to heteroaryl and heterocycloalkyl used herein, refers to groups containing one to four heteroatoms each selected from O, S and N, wherein each heterocycle group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. In some embodiments, it is understood that the heterocycle ring has additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In some embodiments, in heterocycles that have two or more heteroatoms, those two or more heteroatoms are the same or different from one another. In some embodiments, heterocycles are optionally substituted. In some embodiments, binding to a heterocycle is at a heteroatom or via a carbon atom. Heterocycloalkyl groups include groups having only 4 atoms in their ring system, but heteroaryl groups must have at least 5 atoms in their ring system. The heterocycle groups include benzo-fused ring systems. An example of a 4-membered heterocycle group is azetidinyl (derived from azetidine). An example of a 5-membered heterocycle group is thiazolyl. An example of a 6-membered heterocycle group is pyridyl, and an example of a 10-membered heterocycle group is quinolinyl. Examples of heterocycloalkyl groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and fiiropyridinyl. In some embodiments, the foregoing groups, as derived from the groups listed above, are C-attached or N-attached where such is possible. For instance, in some embodiments, a group derived from pyrrole is pyrrol-1-yl (N-attached) or pyrrol-3-yl (C-attached). Further, in some embodiments, a group derived from imidazole is imidazol-1-yl or imidazol-3-yl (both N-attached) or imidazol-2-yl, imidazol-4-yl or imidazol-5-yl (all C-attached). The heterocycle groups include benzo-fused ring systems and ring systems substituted with one or two oxo (=O) moieties such as pyrrolidin-2-one. In some embodiments, depending on the structure, a heterocycle group is a monoradical or a diradical (i.e., a heterocyclene group).

The heterocycles described herein are substituted with 0, 1, 2, 3, or 4 substituents independently selected from alkenyl, alkoxy, alkoxyalkyl, alkoxycarbonyl, alkyl, alkylcarbonyl, alkylcarbonyloxy, alkylthio, alkylthioalkyl, alynyl, carboxy, cyano, formyl, haloalkoxy, haloalkyl, halogen, hydroxyl, hydroxyalkylene, mercapto, nitro, —$NR_AR_B$, and —($NR_AR_B$)carbonyl.

The term "heterocycloalkoxy" refers to a heterocycloalkyl group, as defined herein, appended to the parent molecular moiety through an alkoxy group.

The term "heterocycloalkylthio" refers to a heterocycloalkyl group, as defined herein, appended to the parent molecular moiety through an alkylthio group.

The term "heterocyclooxy" refers to a heterocycloalkyl group, as defined herein, appended to the parent molecular moiety through an oxygen atom.

The term "heterocyclothio" refers to a heterocycloalkyl group, as defined herein, appended to the parent molecular moiety through a sulfur atom.

The term "heteroarylalkoxy" refers to a heteroaryl group, as defined herein, appended to the parent molecular moiety through an alkoxy group.

The term "heteroarylalkylthio" refers to a heteroaryl group, as defined herein, appended to the parent molecular moiety through an alkylthio group.

The term "heteroaryloxy" refers to a heteroaryl group, as defined herein, appended to the parent molecular moiety through an oxygen atom.

The term "heteroarylthio" refers to a heteroaryl group, as defined herein, appended to the parent molecular moiety through a sulfur atom.

In some embodiments, the term "membered ring" embraces any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "non-aromatic 5, 6, 7, 8, 9, 10, 11 or 12-bicyclic heterocycle" as used herein, means a heterocycloalkyl, as defined herein, consisting of two carbocyclic rings, fused together at the same carbon atom (forming a Spiro structure) or different carbon atoms (in which two rings share one or more bonds), having 5 to 12 atoms in its overall ring system, wherein one or more atoms forming the ring is a heteroatom. Illustrative examples of non-aromatic 5, 6, 7, 8, 9, 10, 11, or 12-bicyclic heterocycle ring include, but are not limited to, 2-azabicyclo[2.2.1]heptanyl, 7-azabicyclo[2.2.1]heptanyl, 2-azabicyclo[3.2.0]heptanyl, 3-azabicyclo[3.2.0]heptanyl, 4-azaspiro[2.4]heptanyl, 5-azaspiro[2.4]heptanyl, 2-oxa-5-azabicyclo[2.2.1]heptanyl, 4-azaspiro[2.5]octanyl, 5-azaspiro[2.5]octanyl, 5-azaspiro[3.4]octanyl, 6-azaspiro[3.4]octanyl, 4-oxa-7-azaspiro[2.5]octanyl, 2-azabicyclo[2.2.2]octanyl, 1,3-diazabicyclo[2.2.2]octanyl, 5-azaspiro[3.5]nonanyl, 6-azaspiro[3.5]nonanyl, 5-oxo-8-azaspiro[3.5]nonanyl, octahydrocyclopenta[c]pyrrolyl, octahydro-1H-quinolizinyl, 2,3,4,6,7,9a-hexahydro-1H-quinolizinyl, decahydropyrido[1,2-a]azepinyl, decahydro-1H-pyrido[1,2-a]azocinyl, 1-azabicyclo[2.2.1]heptanyl, 1-azabicyclo[3.3.1]nonanyl, quinuclidinyl, and 1-azabicyclo[4.4.0]decanyl.

The term "hydroxyalkylene" as used herein, means at least one hydroxyl group, as defined herein, is appended to the parent molecular moiety through an alkylene group, as defined herein. Illustrative examples of hydroxyalkylene include, but not limited to hydroxymethylene, 2-hydroxyethylene, 3-hydroxypropylene and 4-hydroxyheptylene.

The term "$NR_A NR_B$" as used herein, means two group, $R_A$ and $R_B$, which are appended to the parent molecular moiety through a nitrogen atom. $R_A$ and $R_B$ are each independently hydrogen, alkyl, and alkylcarbonyl. Illustrative examples of $NR_A R_B$ include, but are not limited to, amino, methylamino, acetylamino, and acetylmethylamino.

The term "$(NR_A NR_B)$carbonyl" as used herein, means a $R_A R_B$, group, as defined herein, appended to the parent molecular moiety through a carbonyl group, as defined herein. Illustrative examples of $(NR_A R_B)$carbonyl include, but are not limited to, aminocarbonyl, (methylamino)carbonyl, (dimethylamino)carbonyl, and (ethylmethylamino)carbonyl.

The term "$NR_C NR_D$" as used herein, means two group, $R_C$ and $R_D$, which are appended to the parent molecular moiety through a nitrogen atom. $R_C$ and $R_D$ are each independently hydrogen, alkyl, and alkylcarbonyl. Illustrative examples of $NR_C R_D$ include, but are not limited to, amino, methylamino, acetylamino, and acetylmethylamino.

The term "$(NR_C NR_D)$carbonyl" as used herein, means a $R_C R_D$, group, as defined herein, appended to the parent molecular moiety through a carbonyl group, as defined herein. Illustrative examples of $(NR_C R_D)$carbonyl include, but are not limited to, aminocarbonyl, (methylamino)carbonyl, (dimethylamino)carbonyl, and (ethylmethylamino)carbonyl.

As used herein, the term "mercaptyl" refers to a (alkyl)S— group.

As used herein, the term "moiety" refers to a specific segment or functional group of a molecule. Chemical moieties are often recognized chemical entities embedded in or appended to a molecule.

As used herein, the term "sulfinyl" refers to a —S(=O)—R, where R is selected from the group consisting of alkyl, cycloalkyl, aryl, heteroaryl (bonded through a ring carbon) and heterocycloalkyl (bonded through a ring carbon).

As used herein, the term "sulfonyl" refers to a —S(=O)$_2$—R, where R is selected from the group consisting of alkyl, cycloalkyl, aryl, heteroaryl (bonded through a ring carbon) and heterocycloalkyl (bonded through a ring carbon).

As used herein, the term "O carboxy" refers to a group of formula RC(=O)O—.

As used herein, the term "C carboxy" refers to a group of formula —C(=O)OR.

As used herein, the term "acetyl" refers to a group of formula —C(=O)CH$_3$.

As used herein, the term "trihalomethanesulfonyl" refers to a group of formula X$_3$CS(=O)$_2$— where X is a halogen.

As used herein, the term "isocyanato" refers to a group of formula —NCO.

As used herein, the term "thiocyanato" refers to a group of formula —CNS.

As used herein, the term "isothiocyanato" refers to a group of formula —NCS.

As used herein, the term "S sulfonamido" refers to a group of formula —S(=O)$_2$NR$_2$.

As used herein, the term "N sulfonamido" refers to a group of formula RS(=O)$_2$NH—.

As used herein, the term "trihalomethanesulfonamido" refers to a group of formula X$_3$CS(=O)$_2$NR—.

As used herein, the term "O carbamyl" refers to a group of formula —OC(=O)NR$_2$.

As used herein, the term "N carbamyl" refers to a group of formula ROC(=O)NH—.

As used herein, the term "O thiocarbamyl" refers to a group of formula —OC(=S)NR$_2$.

As used herein, the term "N thiocarbamyl" refers to a group of formula ROC(=S)NH—.

As used herein, the term "C amido" refers to a group of formula —C(=O)NR$_2$.

As used herein, the term "N amido" refers to a group of formula RC(=O)NH—.

As used herein, the substituent "R" appearing by itself and without a number designation refers to a substituent selected from among from alkyl, cycloalkyl, aryl, heteroaryl (bonded through a ring carbon) and non-aromatic heterocycle (bonded through a ring carbon).

The term "substituted" means that the referenced group is optionally substituted (substituted or unsubstituted) with one or more additional group(s) individually and independently selected from alkyl, cycloalkyl, aryl, heteroaryl, heteroalicyclic, hydroxy, alkoxy, aryloxy, mercapto, alkylthio, arylthio, alkylsulfoxide, arylsulfoxide, alkylsulfone, arylsulfone, cyano, halo, carbonyl, thiocarbonyl, isocyanato, thiocyanato, isothiocyanato, nitro, perhaloalkyl, perfluoroalkyl, silyl, and amino, including mono- and di-substituted amino groups, and the protected derivatives thereof. By way of example an optional substituents is $L_s R_s$, wherein each $L_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted C$_1$-C$_6$ alkyl), or -(substituted or unsubstituted C$_2$-C$_6$ alkenyl); and each $R_s$ is independently selected from H, (substituted or unsubstituted lower alkyl), (substituted or unsubstituted lower cycloalkyl), heteroaryl, or heteroalkyl.

The term "protecting group" refers to a removable group which modifies the reactivity of a functional group, for example, a hydroxyl, ketone or amine, against undesirable reaction during synthetic procedures and to be later removed. Examples of hydroxy-protecting groups include, but not limited to, methylthiomethyl, tert-dimethylsilyl, tert-butyldiphenylsilyl, ethers such as methoxymethyl, and esters including acetyl, benzoyl, and the like. Examples of ketone protecting groups include, but not limited to, ketals, oximes, O-substituted oximes for example O-benzyl oxime, O-phenylthiomethyl oxime, 1-isopropoxycyclohexyl oxime, and the like. Examples of amine protecting groups include, but are not limited to, tert-butoxycarbonyl (Boc) and carbobenzyloxy (Cbz).

The term "optionally substituted" as defined herein, means the referenced group is substituted with zero, one or more substituents as defined herein.

The term "protected-hydroxy" refers to a hydroxy group protected with a hydroxy protecting group, as defined above.

In some embodiments, compounds of the described herein exist as stereoisomers, wherein asymmetric or chiral centers are present. Stereoisomers are designated (R) or (S) depending on the configuration of substituents around the chiral carbon atom. The term (R) and (S) used herein are configurations as defined in IUPAC 1974 Recommendations for Section E, Fundamental Stereochemistry, Pure Appl. Chem., (1976), 45:13-30, hereby incorporated by reference. The embodiments described herein specifically include the various stereoisomers and mixtures thereof. Stereoisomers include enantiomers, diastereomers, and mixtures of enantiomers or diastereomers. In some embodiments, individual stereoisomers of compounds are prepared synthetically from commercially available starting materials which contain asymmetric or chiral centers or by preparation of racemic mixtures followed by resolution. These methods of resolution are exemplified by (1) attachment of a mixture of enantiomers to a chiral axillary, separation of the resulting mixture of diastereomers by recrystallization or chromatography and liberation of the optically pure product from the auxiliary or (2) direct separation of the mixture of optical enantiomers on chiral chromatographic column.

The methods and formulations described herein include the use of N-oxides, crystalline forms (also known as polymorphs), or pharmaceutically acceptable salts of compounds described herein, as well as active metabolites of these compounds having the same type of activity. In some situations, compounds exist as tautomers. All tautomers are included within the scope of the compounds presented herein. In some embodiments, the compounds described herein exist in unsolvated as well as solvated forms with pharmaceutically acceptable solvents such as water, ethanol, and the like. The solvated forms of the compounds presented herein are also considered to be disclosed herein.

Throughout the specification, groups and substituents thereof are chosen, in certain embodiments, to provide stable moieties and compounds.

Preparation of Compounds Described Herein

In certain embodiments, the compounds described herein are synthesized using any synthetic techniques including standard synthetic techniques and the synthetic processes described herein. In specific embodiments, the following synthetic processes are utilized.

Formation of Covalent Linkages by Reaction of an Electrophile with a Nucleophile Selected examples of covalent linkages and precursor functional groups which yield them are given in the Table entitled "Examples of Covalent Linkages and Precursors Thereof." Precursor functional groups are shown as electrophilic groups and nucleophilic groups. In certain embodiments, a functional group on an organic substance is attached directly, or attached via any useful spacer or linker as defined below.

TABLE 1

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

In general, carbon electrophiles are susceptible to attack by complementary nucleophiles, including carbon nucleophiles, wherein an attacking nucleophile brings an electron pair to the carbon electrophile in order to form a new bond between the nucleophile and the carbon electrophile.

Suitable carbon nucleophiles include, but are not limited to alkyl, alkenyl, aryl and alkynyl Grignard, organolithium, organozinc, alkyl-, alkenyl, aryl- and alkynyl-tin reagents (organostannanes), alkyl-, alkenyl-, aryl- and alkynyl-borane reagents (organoboranes and organoboronates); these carbon nucleophiles have the advantage of being kinetically stable in water or polar organic solvents. Other carbon nucleophiles include phosphorus ylids, enol and enolate reagents; these carbon nucleophiles have the advantage of being relatively easy to generate from precursors. Carbon nucleophiles, when used in conjunction with carbon electrophiles, engender new carbon-carbon bonds between the carbon nucleophile and carbon electrophile.

Non-carbon nucleophiles suitable for coupling to carbon electrophiles include but are not limited to primary and secondary amines, thiols, thiolates, and thioethers, alcohols, alkoxides, azides, semicarbazides, and the like. These non-carbon nucleophiles, when used in conjunction with carbon electrophiles, typically generate heteroatom linkages (C—X—C), wherein X is a heteroatom, e.g, oxygen or nitrogen.

Use of Protecting Groups

The term "protecting group" refers to chemical moieties that block some or all reactive moieties and prevent such groups from participating in chemical reactions until the protective group is removed. In specific embodiments, more than one protecting group is utilized. In more specific embodiments, each protective group is removable by a different process. Protective groups that are cleaved under totally disparate reaction conditions fulfill the requirement of differential removal. In various embodiments, protective groups are removed by acid, base, or hydrogenolysis. Groups such as trityl, dimethoxytrityl, acetal and t-butyldimethylsilyl are acid labile and are, in some embodiments, used to protect carboxy and hydroxy reactive moieties in the presence of amino groups protected with Cbz groups, which are removable by hydrogenolysis, and Fmoc groups, which are base labile. In some embodiments, carboxylic acid and hydroxy reactive moieties are blocked with base labile groups such as, without limitation, methyl, ethyl, and acetyl in the presence of amines blocked with acid labile groups such as t-butyl carbamate or with carbamates that are both acid and base stable but hydrolytically removable.

In certain embodiments, carboxylic acid and hydroxy reactive moieties are blocked with hydrolytically removable protective groups such as the benzyl group, while, in some embodiments, amine groups capable of hydrogen bonding with acids are blocked with base labile groups such as Fmoc. In various embodiments, carboxylic acid reactive moieties are protected by conversion to simple ester derivatives as exemplified herein, or they are blocked with oxidatively-removable protective groups such as 2,4-dimethoxybenzyl, while, in some embodiments, co-existing amino groups are blocked with fluoride labile silyl carbamates.

In certain instances, allyl blocking groups are useful in the presence of acid- and base-protecting groups since the former are stable. In some embodiments, such groups are subsequently removed by metal or Pd⁰-acid catalysts. For example, in some embodiments, an alkyl-blocked carboxylic acid is deprotected with a Pd-catalyzed reaction in the presence of acid labile t-butyl carbamate or base-labile acetate amine protecting groups. In some embodiments, a protecting group is a resin to which a compound or intermediate is attached. As long as the residue is attached to the resin, that functional group is blocked and cannot react. Once released from the resin, the functional group is available to react.

In some embodiments, blocking/protecting groups are selected from, by way of non-limiting example:

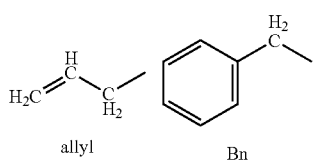

allyl    Bn

-continued

Cbz    alloc

Me    Et    t-butyl    TBDMS

Teoc    Boc pMBn    trityl    acetyl

Fmoc

Other protecting groups are described in Greene and Wuts, Protective Groups in Organic Synthesis, 3rd Ed., John Wiley & Sons, New York, N.Y., 1999.

Compounds of Formula (I)

Preparations of compounds used in the invention are described in WO2010/017055 which is herein incorporated by reference in its entirety.

In certain embodiments, compounds of Formula (I), composing of Ia to If, are prepared in various ways, as outlined in Synthetic Schemes 1 and 2. In each scheme, the variables (e.g., $R_1$, $R_2$, $R_3$, $R_4$, $R_5$, Y, and Z) correspond to the same definitions as those recited above while R is alkyl and Y' is the same or different group defined by Y and Z' is the same or different group defined by Z. In some embodiments, compounds are synthesized using methodologies analogous to those described below by the use of appropriate alternative starting materials.

In certain embodiments, compounds of Formula (Ia, and Ib) wherein Y is identical to Z are synthesized according to Synthetic Scheme 1. Thus, the preparation of the intermediate 3 wherein $R_5$ is hydrogen is achieved by condensation of 4-aminoisobenzofuran-1(3H)-one 1 with an aldehyde 2 in the presence of a base preferably alkaline alkoxides in appropriate solvents such as ethyl acetate or ethyl propionate at either ambient or elevated temperature. Compounds of Formula Ia wherein $R_5$ is hydrogen is prepared by treating the intermediate 3 with hydrazine hydrate at ambient or elevated temperature. Compounds of Formula Ia wherein $R_5$ is alkyl or substituted alkyl is prepared from compound of Formula Ia wherein $R_5$ is hydrogen by reductive amination reaction with $R_7$—CHO wherein $R_7$ is alkyl, substituted alkyl. In some embodiments, the preparation of the compounds in Formula Ib is accomplished by further modification of Ia. Through appropriate functional group transformations on the moiety of Y and Z, one affords the compounds of Formula Ib with different entities of Y' and Z' at 2- or 3-positions.

reductive amination reaction with $R_7$—CHO wherein $R_7$ is alkyl, or substituted alkyl. In some embodiments, the preparation of compounds of Formula Id are accomplished by further modification of Ic. Through appropriate functional group transformations on the moiety of Y and Z, one could afford the compounds of Formula Ic with different entities of Y' and Z' at 2- or 3-positions.

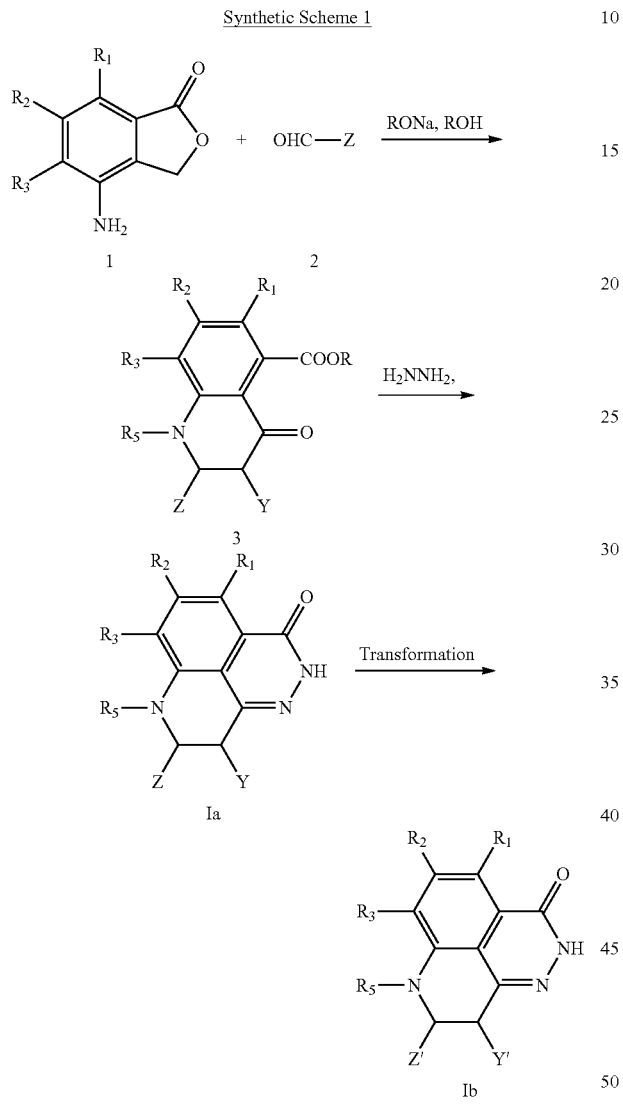

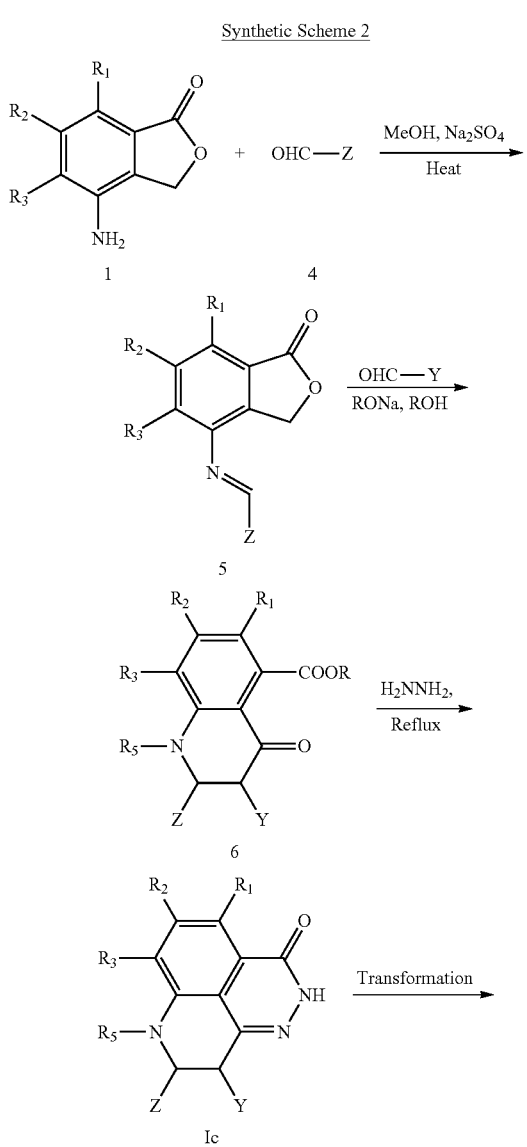

In certain embodiments, compounds of Formula (Ic, and Id) are synthesized according to Synthetic Scheme 2. For example, the intermediate 5 is prepared by condensation of the reagent 1 with an aldehyde 4 in the presence of water absorbent such sodium sulfate or magnesium sulfate at elevated temperature. A subsequent condensation reaction of this intermediate with another aldehyde in the presence of a base preferably alkaline alkoxides in appropriate solvents such as ethyl acetate or ethyl propionate at either ambient or elevated temperature gives the intermediate 6 wherein $R_5$ is hydrogen. Compounds of Formula Ic wherein $R_5$ is hydrogen is prepared by treating the intermediate 6 with hydrazine hydrate at ambient or elevated temperature. Compounds of Formula Ic wherein $R_5$ is alkyl, substituted alkyl are prepared from compounds of Formula Ic wherein $R_5$ is hydrogen by Certain Pharmaceutical Terminology The term "acceptable" with respect to a formulation, composition or ingredient, as used herein, means having no persistent detrimental effect on the general health of the subject being treated.

As used herein, the term "selective binding compound" refers to a compound that selectively binds to any portion of one or more target proteins.

As used herein, the term "selectively binds" refers to the ability of a selective binding compound to bind to a target protein, such as, for example, PARP, with greater affinity than it binds to a non-target protein. In certain embodiments, specific binding refers to binding to a target with an affinity that is at least about 10, about 50, about 100, about 250, about 500, about 1000 or more times greater than the affinity for a non-target.

As used herein, the term "target protein" refers to a molecule or a portion of a protein capable of being bound by a selective binding compound. In certain embodiments, a target protein is the enzyme poly(ADP-ribose)polymerase (PARP).

As used herein, the terms "treating" or "treatment" encompass either or both responsive and prophylaxis measures, e.g., designed to inhibit, slow or delay the onset of a symptom of a disease or disorder, achieve a full or partial reduction of a symptom or disease state, and/or to alleviate, ameliorate, lessen, or cure a disease or disorder and/or its symptoms.

As used herein, amelioration of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

As used herein, the term "modulator" refers to a compound that alters an activity of a molecule. For example, a modulator includes a compound that causes an increase or a decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

As used herein, the term "selective modulator" refers to a compound that selectively modulates a target activity.

As used herein, the term "PARP" refers to the family of the enzyme poly(ADP-ribose)polymerase which includes approximately 18 proteins, particularly poly(ADP-ribose)polymerase-1 (PARP-1) and poly(ADP-ribose)polymerase-2 (PARP-2).

As used herein, the term "selective PARP modulator" refers to a compound that selectively modulates at least one activity associated with the enzyme poly(ADP-ribose)polymerase (PARP). In various embodiments, the selective modulator selectively modulates the activity of PARP-1, PARP-2, both PARP-1 and PARP-2 or several members of the family of the enzyme poly(ADP-ribose)polymerase (PARP).

As used herein, the term "method of inhibiting PARP" refers to a method of inhibiting the activity of either one or more of the family of enzyme poly(ADP-ribose)polymerase (PARP). As used herein, the term "inhibition of PARP" refers to inhibition of the activity of either one or more of the family of enzyme poly(ADP-ribose)polymerase (PARP).

As used herein, the term "modulating the activity of the enzyme poly(ADP-ribose)polymerase" refers to a modulating the activity of either one or more of the family of enzyme poly(ADP-ribose)polymerase (PARP).

As used herein, the term "selectively modulates" refers to the ability of a selective modulator to modulate a target activity to a greater extent than it modulates a non-target activity. In certain embodiments the target activity is selectively modulated by, for example about 2 fold up to more that about 500 fold, in some embodiments, about 2, 5, 10, 50, 100, 150, 200, 250, 300, 350, 400, 450 or more than 500 fold.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "agonist" refers to a compound, the presence of which results in a biological activity of a protein that is the same as the biological activity resulting from the presence of a naturally occurring ligand for the protein, such as, for example, PARP.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" or "inhibitor" refers to a compound, the presence of which results in a decrease in the magnitude of a biological activity of a protein. In certain embodiments, the presence of an antagonist results in complete inhibition of a biological activity of a protein, such as, for example, the enzyme poly(ADP-ribose)polymerase (PARP).

As used herein, the $IC_{50}$ refers to an amount, concentration or dosage of a particular test compound that achieves a 50% inhibition of a maximal response, such as modulation of PARP, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

The term "cancer", as used herein refers to an abnormal growth of cells which tend to proliferate in an uncontrolled way and, in some cases, to metastasize (spread). The types of cancer include, but are not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The terms "disease, condition or disorder associated with a PTEN deficiency" or "disease or disorder associated with a PTEN deficiency", as used herein refer to diseases, conditions or disorders that are caused by, mediated by or related to pathways that are affected (either positively or negatively) by the partial and/or complete loss of PTEN activity (e.g., PTEN deficiency). In some embodiments, a disease or disorder associated with a PTEN deficiency refers to a disease or disorder involving an abnormal ability to control the phosphoinositide 3-kinase signaling pathway. In other embodiments, a disease or disorder associated with a PTEN deficiency refers to a disease or disorder involving a deficiency in Homologous Recombination (FIR) dependent DNA double strand break (DSB) repair pathway. In still other embodiments, a disease or disorder associated with a PTEN deficiency refers to a disease or disorder related to abnormal regulation of centromere stability.

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents include chemicals used to stabilize compounds because they provide a more stable environment. Salts dissolved in buffered solutions (which also can provide pH control or maintenance) are utilized as diluents in certain embodiments, including, but not limited to a phosphate buffered saline solution.

The terms "radiation therapy" (radiotherapy) or "ionizing radiation therapy", as used herein, refer to the use of ionizing radiation as part of a cancer treatment to control the proliferation of cancer cells. Ionizing radiation therapy may be used for curative or adjuvant cancer treatment. Additionally, it can be used as a palliative treatment (where cure is not possible and the aim is for local disease control or symptomatic relief) or as a therapeutic treatment (where the therapy has survival benefit and it can be curative). The precise treatment intent (curative, adjuvant, neoadjuvant, therapeutic, or palliative) will depend on the tumour type, location, and stage, as well as the general health of the patient.

The terms "effective amount" or "therapeutically effective amount," as used herein, refer to a sufficient amount of an agent or a compound being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "enzymatically cleavable linker," as used herein refers to unstable or degradable linkages which are degraded by one or more enzymes.

The term "inflammatory disorders" refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporal arteritis); joints (arthritis: crystalline, osteo-, psoriatic, reactive, rheumatoid, Reiter's); gastrointestinal tract (Chrohn's Disease, ulcerative colitis); skin (dermatitis); or multiple organs and tissues (systemic lupus erythematosus).

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, in certain instances, enzymes produce specific structural alterations to a compound. In some embodiments, metabolites of the compounds disclosed herein are identified either by administration of compounds to a host and analysis of tissue samples from the host, or by incubation of compounds with hepatic cells in vitro and analysis of the resulting compounds.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

By "pharmaceutically acceptable" or "therapeutically acceptable", as used herein, refers a material, such as a carrier or diluent, which does not abrogate the biological activity or properties of the compound, and is relatively nontoxic. In certain instances, nontoxic and non-abrogative materials includes materials that when administered to an individual do not cause substantial, undesirable biological effects and/or do not interact in a deleterious manner with any of the components of the composition in which it is contained.

The term "pharmaceutically acceptable salt" or "therapeutically acceptable salt", refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

A "prodrug" refers to an agent that is converted into the parent drug in vivo. Prodrugs are often useful because, in some situations, they are easier to administer than the parent drug. In certain instances, a prodrug is bioavailable by oral administration whereas the parent is not. In some instances, a prodrug has improved solubility in pharmaceutical compositions over the parent drug. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid or amino group where the peptide is metabolized to reveal the active moiety. In certain embodiments, upon in vivo administration, a prodrug is chemically converted to the biologically, pharmaceutically or therapeutically more active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. In some embodiments, the prodrug is designed to alter the metabolic stability or the transport characteristics of a drug, to mask side effects or toxicity, to improve the flavor of a drug or to alter other characteristics or properties of a drug.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Composition/Formulation

In certain embodiments, pharmaceutical compositions are formulated in any manner, including using one or more physiologically acceptable carriers comprising excipients and/or auxiliaries which facilitate processing of the active compounds into pharmaceutical preparations. In some embodiments, proper formulation is dependent upon the route of administration chosen. In various embodiments, any techniques, carriers, and excipients are used as suitable.

Provided herein are pharmaceutical compositions that include a compound described herein and a pharmaceutically acceptable diluent(s), excipient(s), and/or carrier(s). In addition, in some embodiments, the compounds described herein are administered as pharmaceutical compositions in which compounds described herein are mixed with other active ingredients, as in combination therapy.

A pharmaceutical composition, as used herein, refers to a mixture of a compound described herein with other chemical components, such as carriers, stabilizers, diluents, dispersing agents, suspending agents, thickening agents, and/or excipients. In certain embodiments, a pharmaceutical composition facilitates administration of the compound to an organism. In some embodiments, practicing the methods of treatment or use provided herein, includes administering or using a pharmaceutical composition comprising a therapeutically effective amount of a compound provided herein. In specific embodiments, the methods of treatment provided for herein include administering such a pharmaceutical composition to a mammal having a disease or condition to be treated. In one embodiment, the mammal is a human. In some embodiments, the therapeutically effective amount varies widely depending on the severity of the disease, the age and relative health of the subject, the potency of the compound used and other factors. In various embodiments, the compounds described herein are used singly or in combination with one or more therapeutic agents as components of mixtures.

In certain embodiments, the pharmaceutical compositions provided herein are formulated for intravenous injections. In certain aspects, the intravenous injection formulations provided herein are formulated as aqueous solutions, and, in some embodiments, in physiologically compatible buffers such as Hank's solution, Ringer's solution, or physiological saline buffer. In certain embodiments, the pharmaceutical compositions provided herein are formulated for transmucosal administration. In some aspects, transmucosal formulations include penetrants appropriate to the barrier to be permeated. In certain embodiments, the pharmaceutical compositions provided herein are formulated for other parenteral injections, appropriate formulations include aqueous or non-aqueous solutions, and in one embodiment, with physiologically compatible buffers or excipients.

In certain embodiments, the pharmaceutical compositions provided herein are formulated for oral administration. In certain aspects, the oral formulations provided herein comprise compounds described herein that are formulated with pharmaceutically acceptable carriers or excipients. Such carriers enable the compounds described herein to be formulated as tablets, powders, pills, dragees, capsules, liquids, gels, syrups, elixirs, slurries, suspensions and the like, for oral ingestion by a patient to be treated.

In some embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are optionally added, such as the cross-linked croscarmellose sodium, polyvinylpyrrolidone, agar, or alginic acid or a salt thereof such as sodium alginate.

In certain embodiments, provided herein is a pharmaceutical composition formulated as dragee cores with suitable coatings. In certain embodiments, concentrated sugar solutions are used in forming the suitable coating, and optionally contain gum arabic, talc, polyvinylpyrrolidone, carbopol gel, polyethylene glycol, and/or titanium dioxide, lacquer solutions, and suitable organic solvents or solvent mixtures. In some embodiments, dyestuffs and/or pigments are added to tablets, dragees and/or the coatings thereof for, e.g., identification or to characterize different combinations of active compound doses.

In certain embodiments, pharmaceutical preparations which are used include orally include push-fit capsules made of gelatin, as well as soft, sealed capsules made of gelatin and a plasticizer, such as glycerol or sorbitol. In some embodiments, the push-fit capsules contain the active ingredients in admixture with filler such as lactose, binders such as starches, and/or lubricants such as talc or magnesium stearate and, optionally, stabilizers. In certain embodiments, in soft capsules, the active compounds are dissolved or suspended in suitable liquids, such as fatty oils, liquid paraffin, or liquid polyethylene glycols. In addition, stabilizers are optionally added. In certain embodiments, the formulations for oral administration are in dosages suitable for such administration.

In certain embodiments, the pharmaceutical compositions provided herein are formulated for buccal or sublingual administration. In certain embodiments, buccal or sublingual compositions take the form of tablets, lozenges, or gels formulated in a conventional manner. In certain embodiments, parenteral injections involve bolus injection or continuous infusion. In some embodiments, formulations for injection are presented in unit dosage form, e.g., in ampoules or in multi-dose containers, with an added preservative. In some embodiments, the pharmaceutical composition described herein is in a form suitable for parenteral injection as a sterile suspensions, solutions or emulsions in oily or aqueous vehicles, and optionally contains formulatory agents such as suspending, stabilizing and/or dispersing agents. Pharmaceutical formulations for parenteral administration include aqueous solutions of the active compounds in water-soluble form. In some embodiments, suspensions of the active compounds are prepared as appropriate oily injection suspensions. Suitable lipophilic solvents or vehicles include fatty oils such as sesame oil, or synthetic fatty acid esters, such as ethyl oleate or triglycerides, or liposomes. In certain embodiments, aqueous injection suspensions contain substances which increase the viscosity of the suspension, such as sodium carboxymethyl cellulose, sorbitol, or dextran. Optionally, the suspensions also contain suitable stabilizers or agents which increase the solubility of the compounds to allow for the preparation of highly concentrated solutions. In alternative embodiments, the active ingredient is in powder form for constitution with a suitable vehicle, e.g., sterile pyrogen-free water, before use.

In some embodiments, the compounds described herein are administered topically. In specific embodiments, the compounds described herein are formulated into a variety of topically administrable compositions, such as solutions, suspensions, lotions, gels, pastes, medicated sticks, balms, creams or ointments. Such pharmaceutical compounds optionally contain solubilizers, stabilizers, tonicity enhancing agents, buffers and/or preservatives.

In certain embodiments, the pharmaceutical compositions provided herein are formulated for transdermal administration of compounds described herein. In some embodiments, administration of such compositions employs transdermal delivery devices and transdermal delivery patches. In certain embodiments, the compositions are lipophilic emulsions or buffered, aqueous solutions, dissolved and/or dispersed in a polymer or an adhesive. Such patches include those constructed for continuous, pulsatile, or on demand delivery of pharmaceutical agents. In some embodiments, transdermal delivery of the compounds described herein is accomplished by use of iontophoretic patches and the like. In certain embodiments, transdermal patches provide controlled delivery of the compounds provided herein, such as, for example, compounds of Formula (I), (IA) or (II). In certain embodiments, the rate of absorption is slowed by using rate-controlling membranes or by trapping the compound within a polymer matrix or gel. Conversely, absorption enhancers are optionally used to increase absorption. Absorption enhancer and carrier include absorbable pharmaceutically acceptable solvents that assist in passage of the compound through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In certain embodiments, the pharmaceutical compositions provided herein are formulated for administration by inhalation. In certain embodiments, in such pharmaceutical compositions formulated for inhalation, the compounds described herein are in a form as an aerosol, a mist or a powder. In some embodiments, pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In certain aspects of a pressurized aerosol, the dosage unit is determined by providing a valve to deliver a metered amount. In certain embodiments, capsules and cartridges of, such as, by way of example only, gelatin for use in an inhaler or insufflator is formulated containing a powder mix of the compound described herein and a suitable powder base such as lactose or starch.

In some embodiments, the compounds described herein are formulated in rectal compositions such as enemas, rectal gels, rectal foams, rectal aerosols, suppositories, jelly suppositories, or retention enemas. In certain embodiments, rectal compositions optionally contain conventional suppository bases such as cocoa butter or other glycerides, as well as synthetic polymers such as polyvinylpyrrolidone, PEG, and the like. In certain suppository forms of the compositions, a low-melting wax such as, but not limited to, a mixture of fatty acid glycerides, optionally in combination with cocoa butter is first melted.

In various embodiments provided herein, the pharmaceutical compositions are formulated in a conventional manner using one or more physiologically acceptable carriers comprising excipients and auxiliaries which facilitate processing of the active compounds into pharmaceutically acceptable preparations. In certain embodiments, proper formulation is dependent upon the route of administration chosen. In various embodiments, any of the techniques, carriers, and excipients is used as suitable. In some embodiments, pharmaceutical compositions comprising a compound described herein are manufactured in a conventional manner, such as, by way of example only, by means of conventional mixing, dissolving, granulating, dragee-making, levigating, emulsifying, encapsulating, entrapping or compression processes.

In certain embodiments, the pharmaceutical compositions include at least one pharmaceutically acceptable carrier, diluent or excipient and a compound described herein described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds described herein exist as tautomers. All tautomers are included within the scope of the compounds presented herein. Additionally, included herein are the solvated and unsolvated forms of the compounds described herein. Solvated compounds include those that are solvated with pharmaceutically acceptable solvents such as water, ethanol, and the like. The solvated forms of the compounds presented herein are also considered to be disclosed herein. In some embodiments, the pharmaceutical compositions described herein include other medicinal or pharmaceutical agents, carriers, adjuvants, such as preserving, stabilizing, wetting or emulsifying agents, solution promoters, salts for regulating the osmotic pressure, and/or buffers. In additional embodiments, the pharmaceutical compositions described herein also contain other therapeutically valuable substances.

Methods for the preparation of compositions containing the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. In various embodiments, the compositions are in liquid solutions or suspensions, solid forms suitable for solution or suspension in a liquid prior to use, or as emulsions. These compositions optionally contain minor amounts of nontoxic, auxiliary substances, such as wetting or emulsifying agents, pH buffering agents, and so forth.

In some embodiments, a composition comprising a compound described herein takes the form of a liquid where the agents are present in solution, in suspension or both. In some embodiments, when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

Useful aqueous suspensions optionally contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful compositions optionally comprise an mucoadhesive polymer, selected for example from carboxymethylcellulose, carbomer (acrylic acid polymer), poly (methylmethacrylate), polyacrylamide, polycarbophil, acrylic acid/butyl acrylate copolymer, sodium alginate and dextran.

Useful compositions optionally include solubilizing agents to aid in the solubility of a compound described herein. The term "solubilizing agent" generally includes agents that result in formation of a micellar solution or a true solution of the agent. Solubilizing agents include certain acceptable nonionic surfactants, for example polysorbate 80, and ophthalmically acceptable glycols, polyglycols, e.g., polyethylene glycol 400, and glycol ethers.

Useful compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Useful compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Certain useful compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Some useful compositions optionally include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Certain useful compositions optionally one or more antioxidants to enhance chemical stability where required. Suitable antioxidants include, by way of example only, ascorbic acid and sodium metabisulfite.

In some embodiments, aqueous suspension compositions are packaged in single-dose non-reclosable containers. In alternative embodiments, multiple-dose reclosable containers are used, in which case it is typical to include a preservative in the composition.

In various embodiments, any delivery system for hydrophobic pharmaceutical compounds is employed. Liposomes and emulsions are examples of delivery vehicles or carriers for hydrophobic drugs. In certain embodiments, certain organic solvents such as N-methylpyrrolidone are employed. In some embodiments, the compounds are delivered using a sustained-release system, such as semipermeable matrices of solid hydrophobic polymers containing the therapeutic agent. Various sustained-release materials are utilized in the embodiments herein. In certain embodiments, sustained-release capsules release the compounds for a few weeks up to over 100 days. In some embodiments, depending on the chemical nature and the biological stability of the therapeutic reagent, additional strategies for protein stabilization are employed.

In certain embodiments, the formulations or compositions described herein benefit from and/or optionally comprise antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Methods of Dosing and Treatment Regimens

In certain embodiments, the compounds described herein are used in the preparation or manufacture of medicaments for the treatment of diseases or conditions associated with a PTEN deficiency in which inhibition of the enzyme poly (ADP-ribose)polymerase (PARP) ameliorates the disease or condition. In some embodiments, a method for treating any of the diseases or conditions described herein in a subject in need of such treatment, involves administration of pharmaceutical compositions containing at least one compound described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest the symptoms of the disease or condition. In some embodiments, amounts effective for this use will depend on the severity and course of the disease or condition, previous therapy, the patient's health status, weight, and response to the drugs, and the judgment of the treating physician. In certain instances, it is considered appropriate for the caregiver to determine such therapeutically effective amounts by routine experimentation (including, but not limited to, a dose escalation clinical trial).

In certain prophylactic applications, compositions containing the compounds described herein are administered to a patient susceptible to or otherwise at risk of a particular disease, disorder or condition. In some embodiments, the amount administered is defined to be a "prophylactically effective amount or dose." In certain embodiments of this use, the precise amounts of compound administered depend on the patient's state of health, weight, and the like. In some embodiments, it is considered appropriate for the caregiver to determine such prophylactically effective amounts by routine experimentation (e.g., a dose escalation clinical trial). In certain embodiments, when used in a patient, effective amounts for this use will depend on the severity and course of the disease, disorder or condition, previous therapy, the patient's health status and response to the drugs, and the judgment of the treating physician.

In certain instances, a patient's condition does not improve or does not significantly improve following administration of a compound or composition described herein and, upon the doctor's discretion the administration of the compounds is optionally administered chronically, that is, for an extended period of time, including throughout the duration of the patient's life in order to ameliorate or otherwise control or limit the symptoms of the patient's disease or condition.

In certain cases wherein the patient's status does improve or does not substantially improve, upon the doctor's discretion the administration of the compounds are optionally given continuously; alternatively, the dose of drug being administered is optionally temporarily reduced or temporarily suspended for a certain length of time (i.e., a "drug holiday"). In certain embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes a reduction from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In certain embodiments, once improvement of the patient's conditions has occurred, a maintenance dose is administered if necessary. In some embodiments, the dosage, e.g., of the maintenance dose, or the frequency of administration, or both, are reduced, as a function of the symptoms, to a level at which the improved disease, disorder or condition is retained. In certain embodiments, however, patients are optionally given intermittent treatment on a long-term basis upon any recurrence of symptoms.

In certain embodiments, the amount of a given agent that corresponds to an effective amount varies depending upon factors such as the particular compound, disease or condition and its severity, the identity (e.g., weight) of the subject or host in need of treatment. In some embodiments, the effective amount is, nevertheless, determined according to the particular circumstances surrounding the case, including, e.g., the specific agent that is administered, the route of administration, the condition being treated, and the subject or host being treated. In certain embodiments, however, doses employed for adult human treatment is in the range of about 0.02 to about 5000 mg per day, in a specific embodiment about 1 to about 1500 mg per day. In various embodiments, the desired dose is conveniently presented in a single dose or as divided doses administered simultaneously (or over a short period of time) or at appropriate intervals, for example as two, three, four or more sub-doses per day.

In some embodiments, the pharmaceutical compositions described herein are in a unit dosage form suitable for single administration of precise dosages. In some instances, in unit dosage form, the formulation is divided into unit doses containing appropriate quantities of one or more compound. In certain embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. In alternative embodiments, multiple-dose reclosable containers are used, in which case it is typical to include a preservative in the composition. By way of example only, formulations for parenteral injection are, in some embodiments, presented in unit dosage form, which include, but are not limited to ampoules, or in multi-dose containers, with an added preservative.

In certain embodiments, the daily dosages appropriate for the compounds described herein described herein are from about 0.01 to about 2.5 mg/kg per body weight. In some embodiments, an indicated daily dosage in the larger subject, including, but not limited to, humans, is in the range from about 0.5 mg to about 100 mg, conveniently administered in divided doses, including, but not limited to, up to four times a day or in extended release form. In certain embodiments, suitable unit dosage forms for oral administration comprise from about 1 to about 50 mg active ingredient. The foregoing ranges are merely suggestive, as the number of variables in regard to an individual treatment regime is large, and considerable excursions from these recommended values are not uncommon. In certain embodiments, the dosages are altered depending on a number of variables, not limited to the activity of the compound used, the disease or condition to be treated, the mode of administration, the requirements of the individual subject, the severity of the disease or condition being treated, and the judgment of the practitioner.

In certain embodiments, toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. In certain embodiments, compounds exhibiting high therapeutic indices are preferred. In some embodiments, the data obtained from cell culture assays and animal studies is used in formulating a range of dosage for use in human. In specific embodiments, the dosage of such compounds lies within a range of circulating concentrations that include the $ED_{50}$ with minimal toxicity. In certain embodiments, the dosage varies within this range depending upon the dosage form employed and the route of administration utilized.

Combination Treatments

In certain instances, it is appropriate to administer at least one compound described herein in combination with another therapeutic agent. By way of example only, if one of the side effects experienced by a patient upon receiving one of the compounds herein is inflammation, then, in some embodiments, it is appropriate to administer an anti-inflammatory agent in combination with the initial therapeutic agent. In some embodiments, the therapeutic effectiveness of one of the compounds described herein is enhanced by administration of an adjuvant (i.e., in some embodiments, by itself the adjuvant has minimal therapeutic benefit, but in combination with another therapeutic agent, the overall therapeutic benefit to the patient is enhanced). In certain embodiments, the benefit experienced by a patient is increased by administering one of the compounds described herein with another therapeutic agent (which also includes a therapeutic regimen) that also has therapeutic benefit. In some embodiments, regardless of the disease, disorder or condition being treated, the overall benefit experienced by the patient as a result of a combination treatment is additive or synergistic.

In certain embodiments, therapeutically-effective dosages vary when the drugs are used in treatment combinations. In some embodiments, therapeutically-effective dosages of drugs and other agents for use in combination treatment regimens is determined in any suitable manner, e.g., through the use of metronomic dosing, i.e., providing more frequent, lower doses in order to minimize toxic side effects. In some embodiments, combination treatment regimen described herein encompass treatment regimens in which administration of a PARP inhibitor described herein is initiated prior to, during, or after treatment with a second agent described above, and continues until any time during treatment with the second agent or after termination of treatment with the second agent. It also includes treatments in which a PARP inhibitor described herein and the second agent being used in combination are administered simultaneously or at different times and/or at decreasing or increasing intervals during the treatment period. Combination treatment further includes periodic treatments that start and stop at various times to assist with the clinical management of the patient. For example, in some embodiments, a PARP inhibitor described herein in the combination treatment is administered weekly at the onset of treatment, decreasing to biweekly, and decreasing further as appropriate.

In certain embodiments, compositions and methods for combination therapy are provided herein. In accordance with one aspect, the pharmaceutical compositions disclosed herein are used to in a method of treating a disease or condition associated with a PTEN deficiency that is ameliorated by inhibition of PARP. Thus, in accordance with certain aspects, the pharmaceutical compositions disclosed herein are used to treat diseases or disorders associated with a PTEN deficiency. In a certain aspect, the pharmaceutical compositions disclosed herein are used in combination, either simultaneously or sequentially, with ionizing radiation or one or more chemotherapeutic agents.

In certain embodiments, combination therapies described herein are used as part of a specific treatment regimen intended to provide a beneficial effect from the co-action of a PARP inhibitor described herein and a concurrent treatment. It is understood that the dosage regimen to treat, prevent, or ameliorate the condition(s) for which relief is sought, is optionally modified in accordance with a variety of factors.

In certain combination therapies described herein, dosages of the co-administered compounds vary depending on the type of co-drug employed, on the specific drug employed, on the disease or condition being treated and so forth. In some embodiments, when co-administered with one or more biologically active agents, the compound provided herein is administered either simultaneously with the biologically active agent(s), or sequentially. In certain aspects wherein the agents are administered sequentially, the attending physician will decide on the appropriate sequence of administering protein in combination with the biologically active agent(s).

In various embodiments, the multiple therapeutic agents (one of which is one of the compounds described herein) are administered in any order or even simultaneously. In certain instances, administration is simultaneous and the multiple therapeutic agents are, optionally, provided in a single, unified form, or in multiple forms (by way of example only, either as a single pill or as two separate pills). In some embodiments, one of the therapeutic agents is given in multiple doses, or both are given as multiple doses. In some instances, administration is not simultaneous and the timing between the multiple doses varies, by way of non-limiting example, from more than zero weeks to less than four weeks. In addition, the combination methods, compositions and formulations are not to be limited to the use of only two agents; the use of multiple therapeutic combinations are also envisioned.

In additional embodiments, the compounds described herein are used in combination with procedures that provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

In certain embodiments, the compounds described herein and combination therapies are administered before, during or after the occurrence of a disease or condition. In certain embodiments, the timing of administering the composition containing a compound varies. Thus, for example, in some embodiments, the compounds are used as a prophylactic and are administered continuously to subjects with a propensity to develop conditions or diseases in order to prevent the occurrence of the disease or condition. In some embodiments, the compounds and compositions are administered to a subject during or as soon as possible after the onset of the symptoms. In certain embodiments, the administration of the compounds is initiated within the first 48 hours of the onset of the symptoms, within the first 6 hours of the onset of the symptoms, or within 3 hours of the onset of the symptoms. The initial administration is achieved via any route practical, such as, for example, an intravenous injection, a bolus injection, infusion over 5 minutes to about 5 hours, a pill, a capsule, transdermal patch, buccal delivery, and the like, or combination thereof. In some embodiments, a compound is administered as soon as is practicable after the onset of a disease or condition is detected or suspected, and for a length of time necessary for the treatment of the disease, such as, from about 1 month to about 3 months. In certain embodiments, the length of treatment varies for each subject, and the length is determined using any criteria. In exemplary embodiments, a compound or a formulation containing the compound is administered for at least 2 weeks, for about 1 month to about 5 years, or for about 1 month to about 3 years.

Chemotherapeutic Agents

In certain embodiments described herein, methods for treatment of PARP mediated conditions or diseases, such as proliferative disorders, including cancer, include administration to a patient compounds, pharmaceutical compositions, or medicaments described herein in combination with at least one additional chemotherapeutic agent selected from, but not limited to, alemtuzumab, arsenic trioxide, asparaginase (pegylated or non-), bevacizumab, trastuxumab, cetuximab, platinum-based compounds (such as cisplatin, carboplatin or oxaliplatin), gemcitabine, cyclphosphamide, cladribine, daunorubicin/doxorubicin/idarubicin, irinotecan, fludarabine, 5-fluorouracil, gemtuzumab, methotrexate, Pacli-taxel™, taxol, temozolomide, thioguanine, or classes of drugs including hormones (an antiestrogen, an antiandrogen, or gonadotropin releasing hormone analogues), interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefitinib, erlotinib, or imatinib, mTOR inhibitors such as temsirolimus or everolimus, or agents to treat signs or symptoms induced by such therapy including allopurinol, filgrastim, granisetron/ondansetron/palonosetron, and dronabinol.

Radiation Therapy

In other embodiments described herein, methods for treatment of PARP mediated conditions or diseases, such as proliferative disorders, including cancer, include administration to a patient compounds, pharmaceutical compositions, or medicaments described herein in combination with at least one type of radiotherapy (or ionizing radiation). Radiotherapy is the use of ionizing radiation as part of a cancer treatment to control the proliferation of cancer cells. Ionizing radiation therapy may be used for curative or adjuvant cancer treatment. Additionally, it can be used as a palliative treatment (where cure is not possible and the aim is for local disease control or symptomatic relief) or as a therapeutic treatment (where the therapy has survival benefit and it can be curative). The precise treatment intent (curative, adjuvant, neoadjuvant, therapeutic, or palliative) will depend on the tumour type, location, and stage, as well as the general health of the patient.

Radiation therapy works by damaging the DNA of cells. The damage is caused by a photon, electron, proton, neutron, or ion beam directly or indirectly ionizing the atoms which make up the DNA chain. Indirect ionization happens as a result of the ionization of water, forming free radicals, notably hydroxyl radicals, which then damage the DNA. In the most common forms of radiation therapy, most of the radiation effect is through free radicals. Because cells have mechanisms for repairing DNA damage, breaking the DNA on both strands proves to be the most significant technique in modifying cell characteristics. Because cancer cells generally are undifferentiated and stem cell-like, they reproduce more, and have a diminished ability to repair sub-lethal damage compared to most healthy differentiated cells. The DNA damage is inherited through cell division, accumulating damage to the cancer cells, causing them to die or reproduce more slowly. Proton radiotherapy works by sending protons with varying kinetic energy to precisely stop at the tumor.

Gamma rays are also used to treat some types of cancer including uterine, endometrial, and ovarian cancers. In the procedure called gamma-knife surgery, multiple concentrated beams of gamma rays are directed on the growth in order to kill the cancerous cells. The beams are aimed from different angles to focus the radiation on the growth while minimizing damage to the surrounding tissues.

Kits/Articles of Manufacture

For use in the therapeutic applications described herein, kits and articles of manufacture are also described herein. In various embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In some embodiments, the containers are formed from a variety of materials such as glass or plastic.

In some embodiments, the articles of manufacture provided herein contain packaging materials. Packaging materials for use in packaging pharmaceutical products include, but are not limited to, blister packs, bottles, tubes, inhalers, pumps, bags, vials, containers, syringes, bottles, and any packaging material suitable for a selected formulation and intended mode of administration and treatment.

In some embodiments, the container(s) described herein comprise one or more compounds described herein, optionally in a composition or in combination with another agent as disclosed herein. The container(s) optionally have a sterile access port (for example in some embodiments the container is an intravenous solution bag or a vial having a stopper pierceable by a hypodermic injection needle). Such kits optionally comprise a compound with an identifying description or label or instructions relating to its use in the methods described herein.

In some embodiments, a kit will comprises one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions is optionally included.

In certain embodiments, a label is on or associated with the container. In some embodiments, a label is on a container when letters, numbers or other characters forming the label are attached, molded or etched into the container itself; a label is associated with a container when it is present within a receptacle or carrier that also holds the container, e.g., as a package insert. In certain embodiments, a label indicates that the contents are to be used for a specific therapeutic application. In some embodiments, the label indicates directions for use of the contents, such as in the methods described herein.

In certain embodiments, the pharmaceutical compositions are presented in a pack or dispenser device which contains one or more unit dosage forms containing a compound provided herein. In some embodiments, the pack contains a metal or plastic foil, such as a blister pack. The pack or dispenser device is optionally accompanied by instructions for administration. In some embodiments, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. In certain embodiments, such notice is, for example, the labeling approved by the U.S. Food and Drug Administration for prescription drugs, or the approved product insert. In some embodiments, compositions containing a compound provided herein are formulated in a compatible pharmaceutical carrier and are placed in an appropriate container labeled for treatment of an indicated condition.

EXAMPLES

The following Examples are intended as an illustration of the various embodiments as defined in the appended claims. In some embodiments, the compounds are prepared by a variety of synthetic routes. All publications, patents, and patent applications cited herein are hereby incorporated by reference for all purposes.

Example 1

Example 1a

Parenteral Composition

To prepare a parenteral pharmaceutical composition suitable for administration by injection, 100 mg of a water-soluble salt of a compound described herein is dissolved in DMSO and then mixed with 10 mL of 0.9% sterile saline. The mixture is incorporated into a dosage unit form suitable for administration by injection.

Example 1b

Oral Composition

To prepare a pharmaceutical composition for oral delivery, 100 mg of a compound described herein is mixed with 750 mg of starch. The mixture is incorporated into an oral dosage unit for, such as a hard gelatin capsule, which is suitable for oral administration.

Example 1c

Sublingual (Hard Lozenge) Composition

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 1d

Inhalation Composition

To prepare a pharmaceutical composition for inhalation delivery, 20 mg of a compound described herein is mixed with 50 mg of anhydrous citric acid and 100 mL of 0.9% sodium chloride solution. The mixture is incorporated into an inhalation delivery unit, such as a nebulizer, which is suitable for inhalation administration.

Example 1e

Rectal Gel Composition

To prepare a pharmaceutical composition for rectal delivery, 100 mg of a compound described herein is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 1f

Topical Gel Composition

To prepare a pharmaceutical topical gel composition, 100 mg of a compound described herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 1g

Ophthalmic Solution Composition

To prepare a pharmaceutical ophthalmic solution composition, 100 mg of a compound described herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Biological Studies

Example 1

PARP 1 Inhibition Assays

Inhibitory effects of test compounds against human PARP 1 enzyme was assessed using Trevigen's Universal Chemiluminescent PARP Assay Kit (Trevigen CAT#4676-096-K) following the manufacturer's recommended protocol.

Immediately prior to performing the assay, the following reagents were prepared: A) 20×PARP Assay Buffer was diluted to 1× with dH$_2$O; B) 10×PARP Cocktail, which contains a mixture of NAD and biotinylated NAD, was diluted by the addition of 10× Activated DNA and 1×PARP Assay Buffer. Both the PARP Cocktail and Activated DNA are 1× after the dilution; C) all test compounds were initially dissolved in DMSO, and subsequently serial diluted with 1×PARP Assay Buffer; D) recombinant human PARP 1 enzyme was diluted with 1×PARP Assay Buffer to generate 0.5 unit/15 µl; E) 10× Strep-Diluent was diluted to 1× with 1×PBS/0.1% Triton X-100; F) Just before use, dilute Strep-HRP 500-fold with 1× Strep-Diluent.

The chemiluminescent assays for PARP activity were performed in white 96-well plates that are pre-coated with histones. Briefly, strip wells were removed from the wrapper, 50 µl/well of 1×PARP Buffer was added to rehydrate the histones and incubation was allowed for 30 minutes at room temperature. Removal of the 1×PARP Buffer from the wells was accomplished by tapping the strip wells on paper towel. Serial dilutions of the test compounds were added to duplicate wells in 10 µl/well volume. Final assay concentrations of test compounds were typically between 1 and 0.0001 µM. Subsequently, recombinant human PARP 1 enzyme was added to 0.5 unit of PARP 1 enzyme/well in 15 µl/well volume. Combined volume of enzyme and inhibitor was 25 µl. Incubate the enzyme/inhibitor mixtures for 10 minutes at room temperature. To start the reaction, 25 µl/well of the 1×PARP Cocktail was added to all the wells. Controls included background wells with 1× Assay Buffer alone (no PARP) and wells with no inhibitor for determining the maximum or 100% PARP activity value. In all cases the final reaction volume was 50 µl.

The reactions were allowed to proceed for 1 hour at room temperature. The plate was then washed 4 times with 200 µl/well 1×PBS/0.1% Triton X-100, using ELx50 Automated Strip Washer (BIO-TEK). After washing, all wells were incubated for 60 minutes with 50 µl/well Strep-HRP, diluted 1:500 with 1× Strep-Diluent. The plate was washed 4 times with 200 µl/well 1×PBS/0.1% Triton X-100 using ELx50 Automated Strip Washer (BIO-TEK). After washing, dry the wells by tapping plate onto paper towels. Mix equal volumes of PeroxyGlow™ A and B together and add 100 µl per well. The light output was immediately determined in a plate reader (EnVision, by Perkin Elmer) set up for measuring chemiluminescence.

The % enzyme activity for each compound is then calculated using the following equation:

$$\% \text{ Inhibition} = \frac{\text{Activity } Ctrl - X}{\text{Activity } Ctrl - \text{Negative } Ctrl} \times 100\%$$

IC$_{50}$ values (the concentration at which 50% of the enzyme activity is inhibited) of each test compound were calculated using GraphPad Prism5 software.

All of the compounds tested had or were expected to have enzymatic PARP inhibitory activity. Of the compounds tested, over 100 compounds had a PARP inhibitory activity in the enzymatic assay of less than 50 nM, with approximately 60 of these compounds having an inhibitory activity of less than 5 nM.

Chemosensitization assay determines the extent by which a PARP inhibitor enhances the tumor cell-killing effect of cytotoxic drugs expressed as PF$_{50}$ (potentiation factor at GI$_{50}$)]. 8000 LoVo cells were seeded into each well of a flat-bottomed 96-well microtiter plate in a volume of 50 µl and incubated in F12K containing 10% (v/v) FBS (medium) overnight at 37° C. Cells were added with 50 µl medium alone, medium containing 2 µM PARP inhibitor, medium containing increasing concentration of Temozolomide (0-2000 µM), and medium containing 2 µM PARP inhibitor and increasing concentration of Temozolomide (0-2000 µM). Final concentration range for Temozolomide was 0-1000 µM where applicable, final concentration of PARA inhibitor was 1 µM where applicable. Final concentration of DMSO was 1% in each well. Cells were allowed to grow for 5 days before cell survival was determined by CellTiter Glo staining (Promega, Madison, Wis., USA). Cell growth, determined after subtraction of time 0 values, was expressed as a percentage of the control well that contained medium with 1% DMSO. GI$_{50}$ (concentration of drug that inhibited growth by 50%) values were calculated from the computer generated curves (GraphPad Software, Inc. San Diego Calif.). The potentiation factor [PF$_{50}$ (potentiation factor at GI$_{50}$)] was calculated as GI$_{50}$ of Temozolomide alone/GI50 of Temozolomide+PARP inhibitor. Reference: Thomas H. D. et al. (2007). Preclinical selection of a novel poly(ADP-ribose) polymerase inhibitor for clinical trial. *Molecular Cancer Therapy* 6, 945-956.

Most of the compounds tested had a PF50 of more than 2×.

Example 2

In Vitro Cytotoxicity Assay in PTEN −/−Cell Lines

Single-Agent Cytotoxicity Assay in PTEN−/− Tumor Cell Lines

Human prostate PC-3, LNCap tumor cells and mammary MDA-MB-468 tumor cells (all PTEN deficient) were seeded in 96-well tissue culture plates for overnight at a density of 500, 1000, and 1000 cells/well, respectively. Culture media for PC-3 is DMEM+10% FBS; culture media for LNCap is RPMI-1640+10% FBS; culture media for MDA-MB-468 is Leibovitz's L-15+10% FBS.

Tumor cell lines wild type for PTEN (MDA-MB-231 and LoVo tumor cells) were seeded as described above at a density of 1500 (MDA-MB-231) and 1000 (LoVo) cells/well. Culture media for MDA-MB-231 is Leibovitz's L-15+10% FBS, culture media for LoVo is F-12K+10% FBS.

All cells were then treated with fresh media containing Compound X, a PARP inhibitor as described herein at increasing concentrations, and incubated for 7 consecutive days (PC-3) or 12 consecutive days (LNCap, MDA-MB-468) with media changed every 5 days to replenish inhibitors.

Cell survival was determined by CellTiter Glo assay (Promega). Cell survival fraction was expressed as a percentage of the non-treatment control, and IC$_{50}$ values were calculated using GraphPad Prism5.

Figure 2:
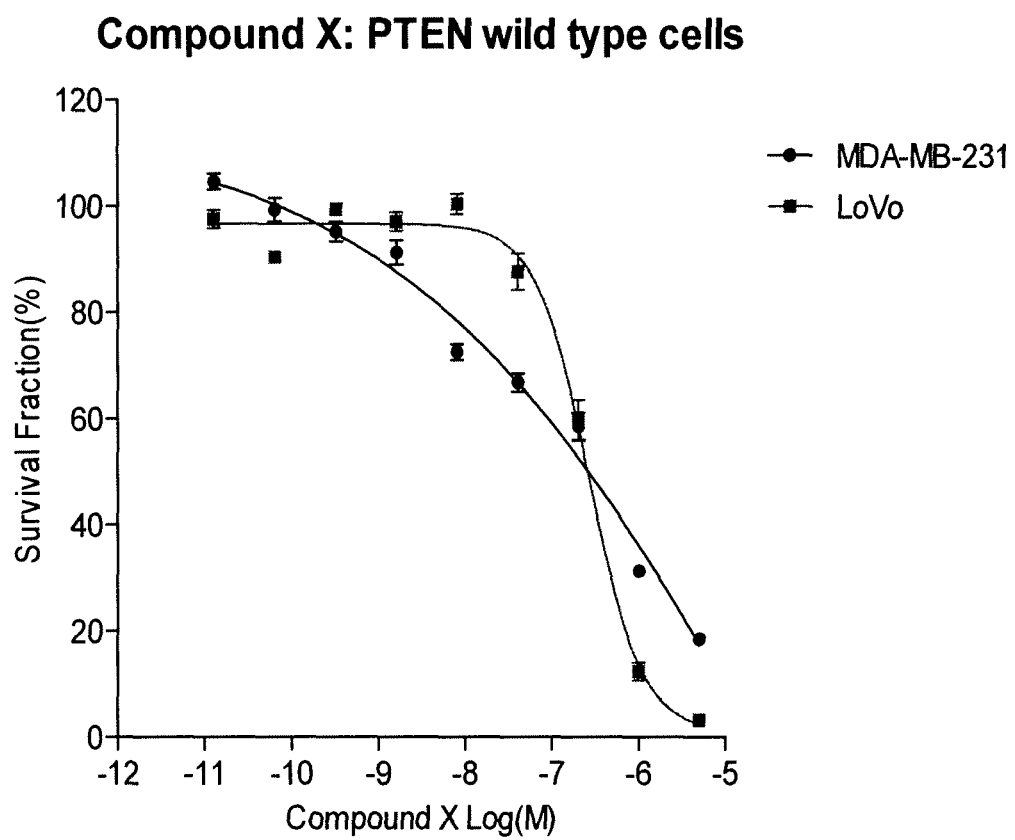
FIG. 2 provides the results of the in vitro cytotoxicity assays performed on tumor cell lines wild type for PTEN treated with a PARP inhibitor described herein (Compound X). (-●-) MDA-MB-231 tumor cell line; and (-■-) LoVo tumor cell line.

The results of the cytotoxicity assays are set forth in FIG. 1 and FIG. 2. The results show that the PTEN −/− tumor cell lines (i.e., PTEN deficient) (LNCap, PC-3, and MDA-MB-468) displayed high sensitivity to treatment with Compound X described herein (FIG. 1), whereas the cell lines wild type for PTEN (MDA-MB-231 and LoVo) did not exhibit the same level of sensitivity to Compound X (FIG. 2).

Example 3

Antitumor Efficacy Study in PTEN −/− Xenografts

Male athymic Balb/c nude mice (7-9 week old) were used for PTEN deficient LNCap and PC-3 in vivo xenografts. Female athymic Balb/c nude mice were used for PTEN deficient MDA-MB-468 in vivo xenograft studies. All mice were quarantined for at least 1 week before experimental manipulation.

Exponentially growing cells were implanted subcutaneously at the right flank of nude mice. Tumor-bearing mice were randomized according to tumor size into 8 mice/group in each study (average tumor size ~140-180 mm$^3$). Mice were observed daily for survival and tumors were measured twice weekly by caliper in two dimensions and converted to tumor mass using the formula for a prolate ellipsoid (V=0.5a×b$^2$), where a and b are the long and short diameters of the tumor, respectively, and assuming unit density (1 mm$^3$=1 mg).

PARP inhibitory compound (Compound X) was evaluated in LNCap, PC-3 and MDA-MB-468 xenografts for single agent activity. Compound X was dosed orally (p.o.), once daily at 0.33 mg/kg for 28 days in vehicle 10% DMAc/6% Solutal/84% PBS and the same vehicle was used as control. Mice were continuously monitored for 10 more days after last day of dosing.

Figure 3:
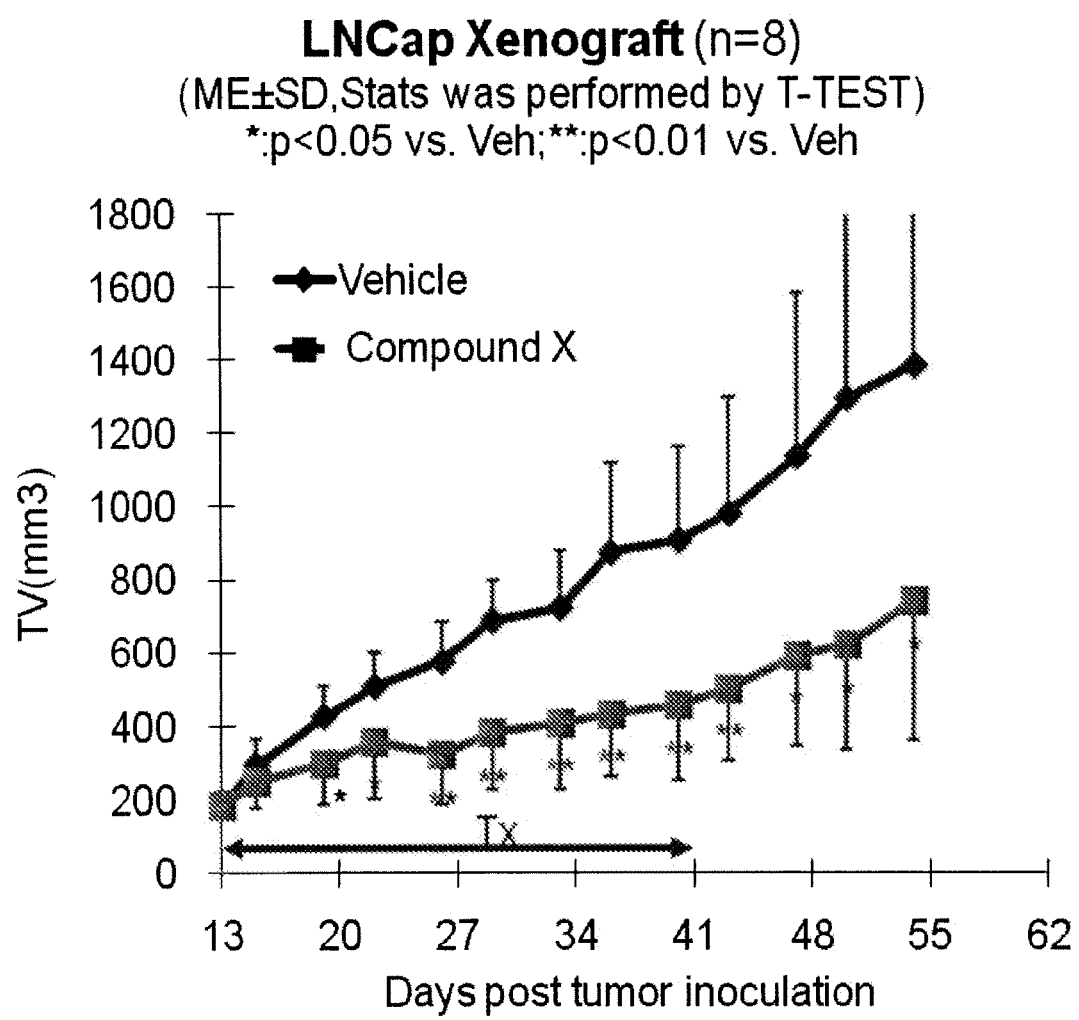
FIG. 3 provides the results of an in vivo efficacy study of a PARP inhibitor (Compound X) in a PTEN deficient LNCap Xenograft model.
Figure 4:
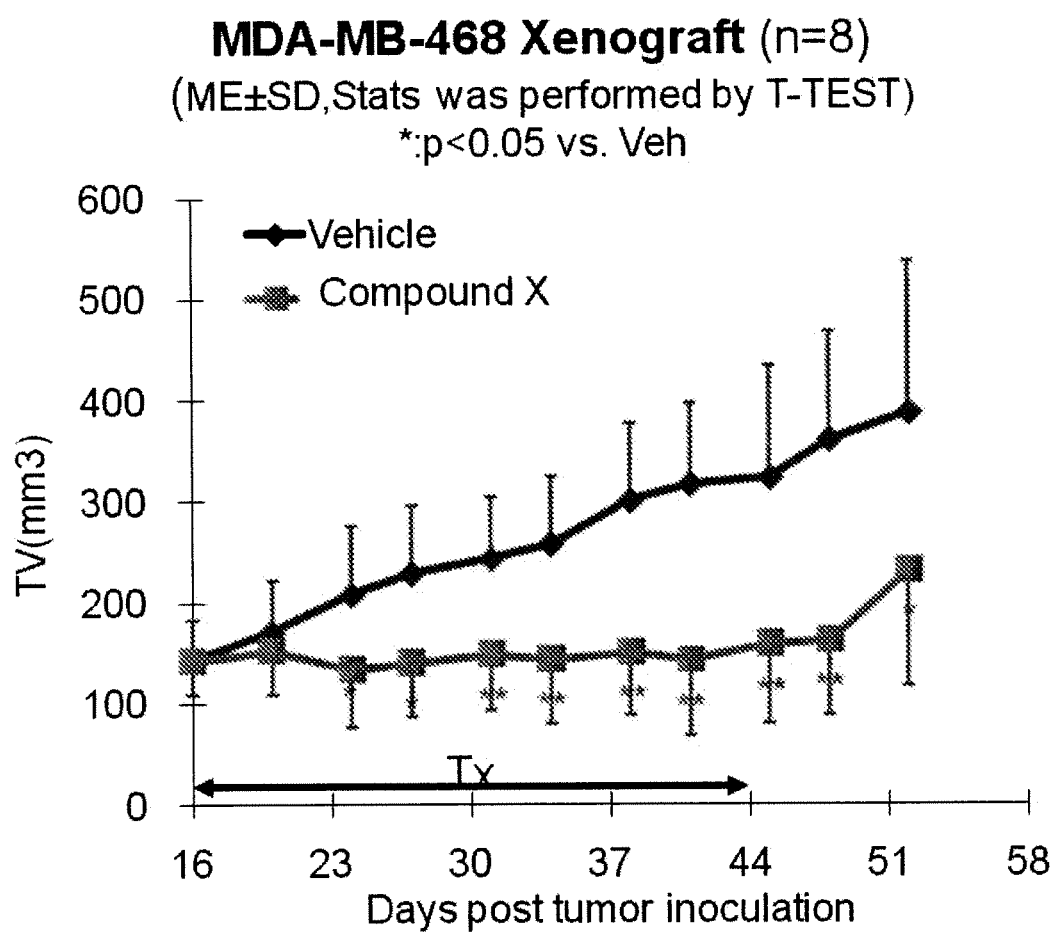
FIG. 4 provides the results of an in vivo efficacy study of a PARP inhibitor (Compound X) in a PTEN deficient MDA-MB-668 Xenograft model.
Figure 5:
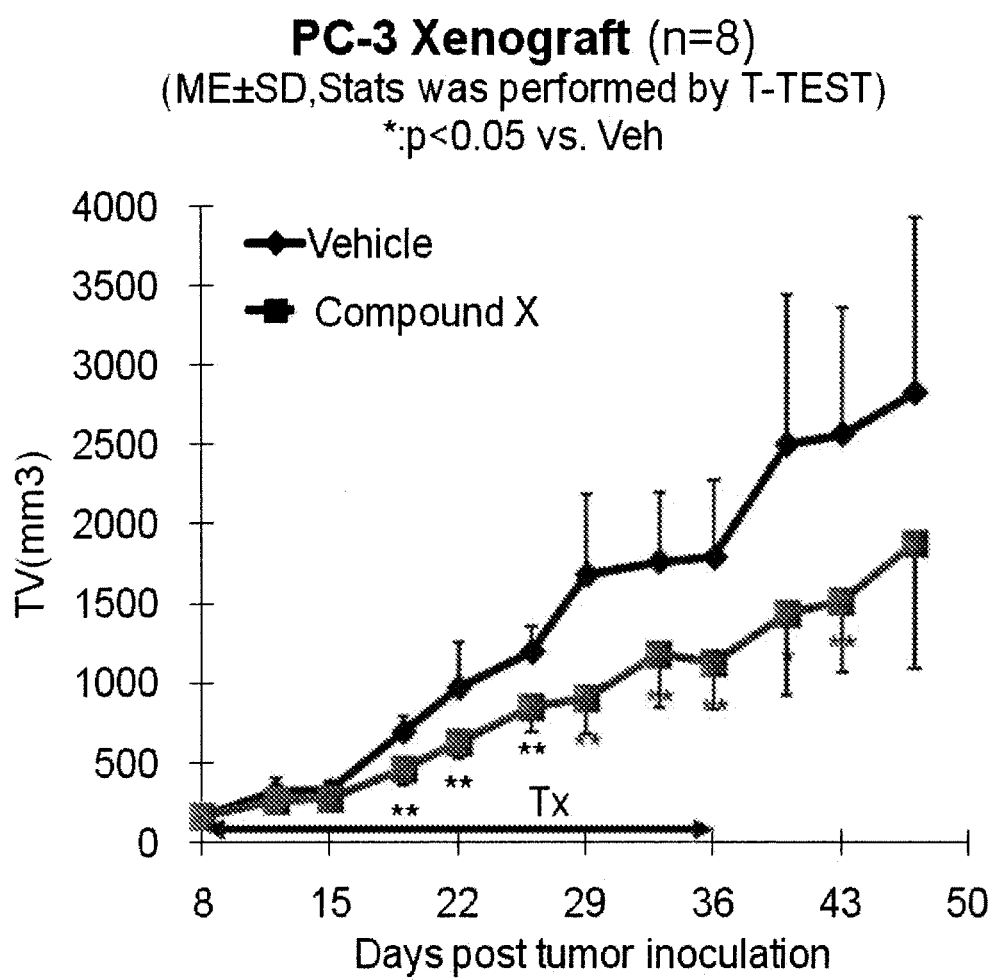
FIG. 5 provides the results of an in vivo efficacy study of a PARP inhibitor (Compound X) in a PTEN deficient PC-3 Xenograft model.

The results of the in vivo xenograft studies are set forth in FIG. 3 (LNCap xenograft), FIG. 4 (MDA-MB-468 xenograft) and FIG. 5 (PC-3 xenograft). The results show that treatment with a PARP inhibitory compound described herein resulted in significant slowing of tumor growth in all three PTEN deficient xenograft models as compared to treatment with only the vehicle (control).

Example 4

Phase II Clinical Trial of the Safety and Efficacy of Compounds of Formula (I), (IA) or (II)

The purpose of this phase II trial is to study the side effects and best dose of a compound of Formula (I), (IA) or (II) and to determine how well it works in treating patients with advanced or recurrent endometrial cancer (EC).

Constitutively active phosphatidylinositol-3 kinase (PI3K)/phosphatase and tensin homolog on chromosome 10 (PTEN) pathway signaling is common in EC and involved in the development and/or progression of the disease. PTEN deficiency has been frequently detected in EC patients. The compounds of Formula (I), (IA) or (II) described herein are potent inhibitors of the family of poly(ADP-ribose)polymerases (PARP). In addition, in vivo data (as set forth in Example 3 above) demonstrates that administration of compounds of Formula (I), (IA) or (II) result in significant slowing of tumor growth in three PTEN deficient xenograft models. Therefore, compounds of Formula (I), (IA) or (II) may have utility in the treatment of subjects with advanced or recurrent EC.

Objectives:
Primary Outcome Measures:
A. Efficacy as defined by overall response rate and progression-free survival (PFS) at 6 months [Time Frame: every 8-10 weeks]
B. Safety a compound of Formula (I), (IA) or (II) in the EC population [Time Frame: scheduled evaluations every 2-4 weeks]
Secondary Outcome Measures:
A. Duration of response and PFS [Time Frame: every 8-10 weeks]
B. Characterize pharmacokinetic and pharmacodynamic profiles of a compound of Formula (I), (IA) or (II) [Time Frame: at periodic visits not less than every 4 weeks]
Tertiary:
A. To evaluate PARP expression using quantitative western blotting immuno-assays
B. To analyze tumor biopsy samples (when possible) for PTEN deficiency mutation status, PARP activity, and PARP expression
C. To analyze paraffin sections from original diagnostic biopsies/operative procedures (when available) for DNA repair enzyme status using immunohistochemical techniques Patients: Eligible subjects will be women 18 years and older Criteria
Inclusion Criteria:
The subject has a histologically confirmed diagnosis of EC (endometrioid, serous, clear cell adenocarcinoma, adenosquamous carcinoma, or mixed histology, any grade) that is advanced or recurrent and is incurable by standard therapies, and has received no more than two prior systemic treatment regimens for EC.
The subject is at least 18 years old.
The subject has an Eastern Cooperative Oncology Group (ECOG) performance status of 0, 1, or 2.
The subject has at least one measurable lesion
Tissue samples from archival or fresh tissue, or a tissue block of the subject's tumor
The subject has adequate organ and marrow function
The subject is capable of understanding the informed consent and complying with the protocol and has signed the informed consent document before any study-specific screening procedures or evaluations are performed.
Sexually active subjects of childbearing potential and their partners must agree to use medically accepted methods of contraception during the course of the study and for 3 months after discontinuation of study drug.
Subjects of childbearing potential must have a negative pregnancy test at screening.
Exclusion Criteria:
The subject has uterine sarcomas (leiomyosarcoma), mixed Mullerian tumors, squamous carcinoma of the uterus, and/or adenosarcomas of the uterus.
Certain restrictions on prior treatments apply
The subject has not recovered from toxicity due to prior therapy to Grade ≦1 or to pre-therapy baseline (excluding alopecia and peripheral neuropathy).
The subject has a known primary brain tumor or brain metastasis.
The subject has any other diagnosis of malignancy or evidence of malignancy (except non-melanoma skin cancer or in situ carcinoma of the cervix) within 2 years before screening for this study.
The subject has a diagnosis of uncontrolled diabetes mellitus or has a fasting plasma glucose >160 mg/dL.
The subject is currently receiving anticoagulation with therapeutic doses of warfarin (low-dose warfarin ≦1 mg/day is permitted).
The subject has prothrombin time (PT)/international normalized ratio (INR) or partial thromboplastin time (PTT) test results at screening that are above 1.3× the laboratory upper limit of normal.
The subject has uncontrolled, significant intercurrent illness
The subject has a baseline corrected QT interval ≧470 ms.
The subject is known to be positive for the human immunodeficiency virus (HIV). (Note: Baseline HIV screening is not required.)
The subject is pregnant or breastfeeding.

The subject has a previously identified allergy or hypersensitivity to components of the study treatment formulation.

What is claimed is:

1. A method of polymerase (PARP) in a treating a disease associated with a PTEN deficiency ameliorated by the inhibition of PARP, wherein the disease associated with a PTEN deficiency is endometrial carcinoma, comprising administering to a subject in need of treatment a therapeutically effective amount of a compound of Formula (I):

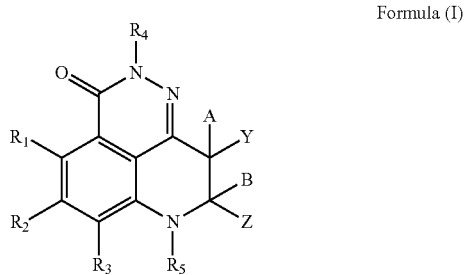

Formula (I)

wherein:

Y and Z are each independently selected from the group consisting of:
a) an aryl group optionally substituted with 1, 2, or 3 $R_6$;
b) a heteroaryl group optionally substituted with 1, 2, or 3 $R_6$; and
c) a substituent independently selected from the group consisting of hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, hetercarylcarbonyl alkylsulfnnyl, arylsulfonyl, heteroarylsulfonyl, $(NR_AR_B)$alkkylene, $(NR_AR_B)$carbonyl, $(NR_AR_B)$carbonylalkylene, $(NR_AR_B)$sulfonyl, and $(NR_AR_B)$sulfonyalkylene;

$R_1$, $R_2$, and $R_3$ are each independently selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl;

A and B are each independently selected from the group consisting of hydrogen, Br, Cl, F, I, OH, $C_1$-$C_6$alkyl, $C_3$-$C_8$cycloalkyl, alkoxy, and alkoxyalkyl, wherein $C_1$-$C_6$alkyl, $C_3$-$C_8$cycloalkyl, alkoxy, and alkoxyalkyl are independently optionally substituted with at least one substituent selected from the group consisting of OH, $NO_2$, CN, Br, Cl, F, I, $C_1$-$C_6$alkyl, and $C_3$-$C_8$cycloalkyl, wherein B is not OH;

$R_A$ and $R_B$ are independently selected from the group consisting of hydrogen, alkyl, cycloalkyl, and alkylcarbonyl; or $R_A$ and $R_B$ taken together with the atom to which they are attached form a 3-10 membered hetrocycle ring optionally having one to three heteroatoms or hetero functionalities selected from the group consisting of —O—, —NH, —N($C_1$-$C_6$-alkyl)-, —N(aryl)-, —NN(aryl-$C_1C_6$alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$—, wherein q is 1 or 2 and the 3-10 membered heterocycle ring is optionally substituted with 1, 2, 3, or 4 substituents independently selected from $C_2$-$C_{10}$-alkenyl, $C_1$-$C_{10}$-alkoxy-$C_1$, -$C_{10}$-alkyl, $C_1$-$C_{10}$-alkoxycarbonyl, $C_1$-$C_{10}$-alkyl, $C_1$-$C_{10}$-alkylcarbonyl, $C_1$-$C_{10}$-alkylcarbonyloxy, $C_1$-$C_{10}$-alkylthio, $C_1$-$C_{10}$-alkylthio-$C_1$-$C_{10-alkyl}$, $C_2$-$C_{10}$alkynyl, carboxy, cyano, formyl, $C_1$-$C_{10}$-haloalkoxy, $C_1$-$C_{10}$-haloalkyl, halogen, hydroxyl, $C_1$-$C_{10}$-hydroxyalkylene, mercapto, nitro, —$NR_AR_B$, and $(NR_AR_B)$carbonyl;

$R_4$ and $R_6$ are each independently selected from the group consisting of hydrogen, alkyl, cycloalkyl, alkoxyalkyl, haloalkyl, hydroxyalkylene, and $(NR_AR_B)$alkylene; and each $R_6$ is selected from the group consisting of OH, $NO_2$, CN, Br, Cl, F, I, $C_1$ $C_6$alkyl, $C_3$-$C_8$cycloalkyl, $C_3$-$C_8$heterocycloalkyl, $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$-cycloalkyalkyl, haloalkoxy, haloakyl, hydroxyalkylene, oxo, heteroaryl, heteroarylalkoxy, heteroaryloxy, heteroaryl thio, heteroarylalkylthio, heterocycloalkoxy, $C_2$-$C_8$heterocycloalkythio, $C_3$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene; or a single isomer, stereoisomer, or enantiomer, or mixture thereof, optionally as a salt, solvate, chemically protected form or prodrug thereof.

2. A method of treating a disease associated with a PTEN deficiency ameliorated by the inhibition of PARP, wherein the disease associated with a PTEN deficiency is eudometrial carcinoma, comprising administering to a subject in need of treatment a therapeutically effective amount of a compound of Formula (II):

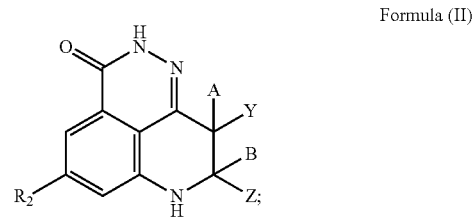

Formula (II)

wherein:

Y is an aryl or heteroaryl group optionally substituted. with 1, 2, or 3 $R_6$;

Z is an aryl group optionally substituted with 1, 2, or 3 $R_6$;

A and B are each independently selected from the group consisting of hydrogen, Br, Cl, F, I, OH, $C_1$-$C_6$alkyl, $C_3$-$C_8$cycloalkyl, alkoxy, and aloxyalkyl, wherein $C_1$-$C_6$alkyl, $C_3$-$C_8$- cycloalkyl, alkoxy, and alkoxyalkyl are optionally substituted with at least one substituent selected from the group consisting of OH, $NO_2$, CN, Br, Cl, F, I, $C_1$-$C_6$alkyl, and $C_3C_8$cycloalkyl, wherein B is not OH;

$R_6$ is selected from the group consisting of OH, $NO_2$, CN, Br, Cl, F, I, $C_1$-$C_6$alkyl, $C_3$-$C_8$cycloalkyl, $C_3$-$C_8$heterocycloalkyl, $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_3$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene;

R$_2$ is selected from the group consisting of hydrogen, Br, Cl, I, and F;

R$_A$ and R$_B$ are independently selected from the group consisting of hydrogen, C$_1$-C$_6$alkyl, C$_3$-C$_8$cycloalkyl, and alkylcarbonyl; or R$_A$ and R$_B$ taken together with the atom to which they are attached form a 3-10 membered heterocycle ring optionally having one to three heteroatoms or hetro functionalities seleted from the group consisting of —O—, —NH, —N(C$_1$-C$_6$alkyl)-, —NCO(C$_1$-C$_6$alkyl)-, —NCO(C$_3$-C$_8$cycloalkyl)- —N(aryl)-, —N(aryl-C$_1$-C$_6$alkyl-)-, —N(substitited-aryl-C$_1$C$_6$alkyl-)-, —N(heteroaryl)-, —N(heteroaryl -C$_1$-C$_6$alkyl-)-, —N(substituted-heteroaryl-C$_{1-C6}$alkyl-)-, and —S— or S(O)$_q$-, wherein q is 1 or 2 and the 3-10 membered heterocycle ring is optionally substituted with 1, 2, 3, or 4 substitnents independently selected from C$_2$-C$_{10}$-alkenyl, C$_1$-C$_{10}$-alkoxy, C$_1$-C$_{10}$alkyl, C$_1$-C$_{10}$-alkoxycarbonyl, C$_1$-C$_{10}$ alkyl, C$_1$-C$_{10}$-alkylcarbonyl, C$_1$-C$_{10}$-alkylcarbonyloxy, C$_1$-C$_{10}$-alkylthio, C$_1$-C$_{10}$-alkylthio-C$_1$C$_{10}$-alkyl, C$_2$-C$_{10}$-alkynyl, carboxy, cyano, formyl, C$_1$C$_{10}$-haloalkoxy, C$_1$-C$_{10}$-haloalkyl, halogen, hydroxyl, C$_1$-C$_{10}$-hydroxyalkylene, mercapto, nitro, —NR$_A$R$_B$, and —(NR$_A$R$_B$)carbonyl; or a single isomer, stereoisomer, or enantiomer, or mixture thereof, optionally as a salt solvate, chemically protected form or prodrug thereof.

3. The method of claim 1 wherein Y is a heteroaryl group optionally substituted with 1, 2, or 3 R$_6$.

4. The method of claim 3 wherein, the heteroaryl group is selected from the group consisting of furan, pyridine, pyrimidine, pyrazine, imidazole, thiazole, isothiazole, pyrazole, triazole, pyrrole, thiophene, oxazole, isoxazole, 1,2,4-oxadiazole, 1,3,4-oxadiazole, 1,2,4-triazine, indole, benzothiophene, benzoimidazole, benzofuran, pyridazine, 1,3,5-triazine, thienothiophene, quinoxaline, quinoline, and isoquinoline; each of which is optionally substituted with 1, 2, or 3 R$_6$.

5. The method of claim 4 wherein the heteroaryl group is substituted with C$_1$-C$_6$alkyl selected from the group consisting of methyl, ethyl n-propyl, iso-propyl, n-butyl, iso-butyl, and tert-butyl.

6. The method of claim 5 wherein C$_1$C$_6$alkyl is methyl.

7. The method of claim 1 wherein Z is an aryl group which is optionally substituted with 1, 2, or 3 R$_6$.

8. The method of claim 7 wherein the aryl group is a phenyl group which is optionally substituted with 1, 2, or 3 R$_6$.

9. The method of any of claim 8 wherein the phenyl group is substituted with 1, 2, or 3 R$_6$ selected from the group consisting of Br, Cl, F, and I.

10. The method of claim 9 wherein R$_6$ is F.

11. The method of claim 1 wherein R$_2$ is selected from the group consisting of F, Cl, Br, and L.

12. The method of cairn 11 wherein R$_2$ is F.

13. A method of treating a disease associated with a PTEN deficiency ameliorated by the inhibition of PARP, wherein the disease associated with a PTEN deficiency is endometrial carcinoma, comprising administering to a subject in need of treatment a therapeutically effective amount of a compound selected from the group consisting of:

8,9-diphenyl-8,9-dihydro-2H-pyrido[4,3,2-de]phtalazin-3(7H)-one,
8,9bis(4-methylamino)methyl)phenyl-8,9-dihydro-2H-pyrido [4,3,2-de]phtalazin-3(7H)-one,
8,9-di(pyridin-4-yl)-8,9-dihydro-2H-pyrido[4,3,2-de]phthalazin-3(7H)-one,
8,9-di(pyridin-3-yl)-8,9-dihydro-2H-pyrido[4,3,2-de]phthalazin-3(7H)-one,
8,9-di(pyridin-2-yl)-8,9-dihydro-2H-pyrido[4,3,2-de]phthalazin-3(7H)-one,
9-isopropyl-8-phenyl-8,9-dihydro-2H-pyrido[4,3,2-de]phthalazin-3(7H)-one,
9-(4-((methylamino)methyl)phenyl)-8-phenyl-8,9-dihydro-2H-pyrido [4,3,2-de]phthalazin-3(7H)-one,
9-(4-((dimethylamino)methyl)phenyl)-8-phenyl-8,9-dihydro-2H-pyrido[4,3,2-de]phthalazin-3(7H)-one,
9-(3-((methylamino)methyl)phenyl)-8-phenyl-8,9-dihydro-2H-pyrido[4,3,2-de]phthalazin-3(7H)-one,
8-(4((methylamino)methyl)phenyl)-9-phenyl-8,9-dihydro-2H- pyrido[4,3,2-de]phthalazin-3(7H)-one,
8,9-bi(3-((methylamino)methyl)phenyl)-8,9-dihydo)-2H-pyrido[4,3,2-de]phthalazin-3(7H)-one,
9-4-(hydroxymethyl)phenyl)-8-phenyl-8,9-dihydro-2H-pyrido[4,3,2-de]phthalazin-3(7H)-one,
9-(3-(4-isobutyrylpiperazine-1-carbonyl)phenyl)-8-phenyl-8,9-dihydro-2H-pyrido[4,3,2-de]phthalazin-3(7H)-one,
8,9-bis(3-(4-(isobutyrylpiperazine-1-carbonyl)phenyl)-8,9-dihydro-2H-pyrido[4,3,2-de]pthalazin-3(7H)-one,
9-(piperidin-3-yl)-8-(pyridin-3-yl)-8,9-dihydro-2H-pyrido[4,3,2-de]phthalazin-3(7H)-one,
9-(piperidin-4-yl)-8-(pyridin-4-yl)-8,9-dihydro-2H-pyrido[4,3,2-de]phthalazin-3(7H)-one,
8,9-bis(4-((dimethylamino)methyl)phenyl)-8,9-dihydro-2H-pyrido[4,3,2-de]phthalazin-3(7H)-one,
9-(4-(4-(cyclopropanecarbonyl)piperazine-1-carbonyl)phenyl)-8(4-((methylamino)methyl)phenyl)-8,9-dihydro-2H-pyrido[4,3,2-de]phthalazin-3(7H)-one,
9-(4-(4-(cyclopropanecarbonyl)piperazine-1-carbonyl)phenyl)-8-(4-((dimethylamino)methyl)phenyl)-8,9-dihydro-2H-pyrido[4,3,2-de]phthalazin-3(7H)-one,
8-(4-(hydromethyl)phenyl)-9-(4-(4-isobutyrylpiperazine-1-carbonyl)phenyl)-8,9-dihydro-2H-pyrido [4,3,2-de]phthalazin-3(7H)-one,
8(4((dimethylamino)methyl)phenyl)-9-(4-(4-isobutyrylpiperazine-1-carbonyl)phenyl)-8,9-dihydro-2H-pyrdio[4,3,2-de]phthalazin-3(7H)-one,
9-(4-(4-(cyclopropanecarbonyl)piperazine-1-carbonyl)phenyl)-8-phenyl-8,9-dihydro-2H-pyrido [4,3,2-de]pthalazin-3(7H)-one,
9(3-(4-(cyclopropanecarbonyl)piprazine-1-carbonyl)phenyl)-8-phenyl-8,9-dihydro-2H-pyrido [4,3,2-de]phthalazin-3(7H)-one,
9-(3-((dimethylamino)methyl)phenyl)-8phenyl-8,9-dihydro-2H-pyrido [4,3,2-de]phthalazin-3(7H)-one,
8-(3-((methylamino)methyl)phenyl)-9-phenyl-8,9-dihydro-2H-pyrido[4,3,2-de]phthalazin-3(7H)-one,
8-(4-((dimethylamino)methyl)phenyl)-9-phenyl-8,9-dihydro-2H-pyrido[4,3,2-de]phthalazin-3(7H)-one,
8-(4-(morpholinomethyl)phenyl)-9-phenyl-8,9-dihydro 2H pyrido[4,3,2 de]phthalazin 3(7H) one,
8-(4-(hydroxymethyl)phenyl)-9-phenyl-8,9-dihydro-2H-pyrido[4,3,2-de]pthalazin-3(7H)-one,
9(3-(4-(cyclopropanecarbonyl)piperazine-1-carbonyl)phenyl)-8-(4-((dimethylamino(methyl)phenyl)-8,9-dihydro-2H-pyrido[4,3,2-de]phthalazin-3(7H)-one,
9-(3-(4-(cyclopropanecarbonyl)piperazine-1-carbonyl)phenyl)-8-(4-(hydroxymethyl)phenyl)-8,9-dihydro-2H-pyrido[4,3,2-de]phthatalin-3(7H)-one,
9-(4-(4-isobutyrylpiperazine-1-carbonyl)phenyl)-8-(4-((methylamino)methyl)phemyl)-8,9-dihydro-2H-pyrido[4,3,2-de]phthalazin-3(7H)-one,
9-(3-(4-isobutyrylpiperazine-1-carbonyl)phenyl)-8-(pyridin-4-yl)-8,9-dihydro-2H-pyrido[4,3,2-de]phthalazin-3(7H-one, 9-(3-((dimethylamino)methyl)phenyl)-8-(pyridin,4-yl)-8,9-dihyro-2H-pyrido[4,3,2-de]phthalazin-3(7H)-one,
9-(3-((methylamino)methyl(phenyl)-8-(pyridin-4-yl)-8,9-dihydro-2H-pyrido[4,3,2-de]phthalazin-3(7H)-one,
9-(4-((dimethylamimo)methyl)phenyl)-8-(pyridin-4-yl)-8,9-dihydro-2H-pyrido[4,3,2-de]phthalazin-3(7H)-one;
9-(3-(hydroxymethyl)phenyl)-8-(pyridin-4-yl)-8,9-dihydro-2H-pyrido[4,3,2-de]phthalazin-3(7H)-one;
9-(4-((methylamino)methyl)phenyl)-8-(pyridin-4-yl)-8,9-dihydro-2H-pyrido[4,3,2-de]phthalazin-3(7H)-one,
9-(3-((dimethylaminio)methyl)phenyl)-8-(pyridin-3-yl)-8,9-dihydro-2H-pyrido [4,3,2-de]phthalazin-3(7H)-one,
9-(3-((methylamino)methyl)phenyl)-8-(pyridin-3-yl)-8,9-dihydro -2H-pyrido[4,3,2-de]phthalazin-3(7H)-one,
9-(4-((dimethylamino)methyl)phenyl)-8-(pyridin-3-yl)-8,9-dihydro-2H-pyrido[4,3,2-de]phthalazin-3(7H)-one,
9-(4-((methylamino)methyl)phenyl)-8-(pyridin-3-yl)-8,9-dihydro-2H-pyrido[4,3,2-de]phthalazin-3(7H)-one,
9-(3-(hydroxymethyl)phenyl)-8-(pyridin-3-yl)-8,9-dihydro-2H-pyrido[4,3,2-de]phthalazin-3(7H)-one,
9-(3-((dimethylamino)methyl)phenyl)-8-(pyridin-2-yl)-8,9-dihydro-2H-pyrido[4,3,2-de]phthalazin-3(7H)-one,
9-(3-((methylamino)methyl)phenyl)-8-(pyridin-2-yl)-8,9-dihydro-2H-pyrido [4,3,2-de]phthalazin-3(7H)-one,
9-(3-(hydroxymethyl)phenyl)-8-(pyridin-2-yl)-8,9-dihydro-2H-pyrido[4,3,2-de]phthalazin-3(7H)-one,
9-(4-((dimethylamino)methyl)phenyl)-8-(pyridin-2-yl)-8,9-dihydro-2H-pyrido[4,3,2-de]phthalazin-3(7H)-one,
9-(4-((methylamino)methyl)phenyl)-8-(pyridin-2-yl)-8,9-dihydro-2H-pyrido[4,3,2-de]phthalazin-3(7H)-one,
9-phenyl-8-(pyridin-2-yl)-8,9-dihydro-2H-pyrido[4,3,2-de]phthalazin-3(7H)-one,
9-phenyl-8-(pyridin-3-yl)-8,9-dihydro-2H-pyrido[4,3,2-de]phthalazin-3(7H)-one,
9-phenyl-8-(pyridin-4-yl)-8,9-dihydro-2H-pyrido[4,3,2-de]phthalazin-3(7H)-one,
5-fluoro-9-phenyl-8-(pyridin-4-yl)-8,9-dihydro-2H-pyrido[4,3,2-de]phthalazin-3(7H)-one,
9-(3((dimethylamino)methyl)phenyl)-5-fluoro-8-(pyridin-4-yl)-8,9-dihydro-2H-pyrido[4,3,2-de]phthalazin-3(7H)-one,
5-fluoru-9-(3-((methylamino)methyl)phenyl)-8-(pyridin-4-yl)-8,9-dihydro-2H-pyrido[4,3,2-de]phthalazin-3(7H)-one,
9-(4-((dimethylamino)methyl)phenyl)-5-fluoro-8-(pyridin-4-yl)- 8,9-dihydro -2H-pyrido[4,3,2-de]phthalazin-3(7H)-one,
5-fluoro-8,9-diphenyl-8,9-dihydro-2H-pyrido[4,3,2-de]phthalazin-3(7H)-one,
9-(4-((dimethylamino)methyl)phenyl)-5-fluoro-8-phenyl-8,9-dihydro-2H-pyrido[4,3,2-de]phthalazin-one,
5-fluoro-9-(4-((methylamino)methyl)phenyl)-8-phenyl-8,9-dihydro-2H-pyrido[4,3,2-de]phthalazin-one,
9-(3-((dimethylamino)methyl)phenyl)-5-fluoro-8-phenyl-8,9-dihydro-2H-pyrido[4,3,2-de]pyiido[4,3,2-de]phthalazin-one,
8-(4-((dimethylamino)methyl)phenyl)-5-fluoro-9-phenyl-8,9-dihydro-2H-pyrido[4,3,2-de]phthalazin-one,
5-fluoro-9-(3-((methylamino)methyl)phenyl)-8-phenyl-,8,9-dihydro-2H-pyrido[4,3,2de]phthalazin-one,
5-fluoro-8-(4-((methylamino)methyl)phenyl)-9-phenyl-8,9-dihydro -2H-pyrido[4,3,2-de]phthalazin-one,
7-methyl-8,9- diphenyl-8,9-dihydro-2H-pyrido[4,3,2-de]phthalazin-3(7H)-one,
7-ethyl-8,9-diphenyl-8,9-dihydro-2H-pyrido[4,3,2-de]phthalazin-3(7H)-one,
5-fluoro-9-(1-methyl-1H-imidazol-2-yl)-8-phenyl-8,9-dihydro-2H-pyrido[4,3,2-de]phthalazin-3(7H)-one,
5-fluoro-8-(4-fluorophenyl)-9-(1-methyl-1H-imidazol-2-yl)-8,9-dihydro-2H-pyrido[4,3,2-de]phthalazin-3(7H)-one,
8-(4-((dimethylamino)methyl)phenyl)-9-(1-methyl-1H-imidazol-2-yl)-8,9-dihydro-2H-pyrido [4,3,2-de]phthalazin-3(7H)-one,
9-(1-isopropyl-1H-imidazol-5-yl)-8-phenyl-8,9-dihydro-2H-pyrido[4,3,2-de]phthalazin-3(7H)-one,
9-(4-methyl-1H-imidazol-2-yl)-8-phenyl-8,9-dihydro-2H-pyrido[4,3,2-de]phthalazin-3(7H) one,
8-phenyl-9-(thiazol-5-yl)-8,9-dihydro-2H-pyrido[4,3,2-de]phthalazin-3(7H)-one,
9-(furan-3-yl)-8,9-dihydro-2H-pyrido[4,3,2de]phthalazin 3(7H)-one,
8-(4-((4-ethylpiperazin-1-yl)methyl)phenyl)-9-phenyl-8,9-dihydro-2H-pyrdo[4,3,2-de]phthalazin-3(7H)-one,
9-phenyl-8-(4-(piperazin-1-ylmethyl)phenyl)-8,9-dihydro-2H-pyrido[4,3,2-de]phthalzin-3(7H)-one,
8-(1-methyl-1H-imidazol-2-yl)-9-phenyl-8,9-dihydro-2H-pyrido[4,3,2-de]phthalazin-3(7H)-one,
9-(1-methyl-1H--imidazol-2-yl)-8-phenyl-8,9-dihydro-2H-pyrido[4,3,2-de]phthalazin-3(7H)-one,
8,9-bis(1-methyl-1H-imidazol-2-yl)-8,9-dihydro-2H-pyrido[4,3,2-de]phthalazin-3(7H)-one,
9-(1H-imidazol-2-yl)-8-phenyl-8,9-dihydro-2H-pyrido[4,3,2-de]phthalazin-3(7H)-one,
9-(1-ethyl-1H-imidazol-2-2yl)-8-phenyl-8,9-dihydro-2H-pyrido[4,3,2-de]phthalazin-3(7H)-one,
8-phenyl-9-(1-propyl-1H-imidazol-2-yl)-8,9-dihydro-2H-pyrido[4,3,2-de]phthalazin-3(7H)-one,
9-(1-methyl-1H-imidazol-5-yl)8-phenyl-8,9-dihydro-2H-pyrido[4,3,2-de]phathalazin-3(7H)-one,
9-(3-((diethylamino)methyl)phenyl)-8-(4-((diethylamino)methyl)phenyl)8,9-dihydro-2H-pyrido [4,3,2-de]phthalazin-3(7H)-one,
9-(3-((4-methylpiperazin-1-yl) methyl)phenyl)-8-phenyl-8,9-dihydro-2H -pyrido[4,3,2-de]phthalazin-3(7H)-one,
8-(4-(4-(cyclopropanecarbonyl)piperazine-1-carbonyl)phenyl)-9-phenyl-8,9-dihydro-2H-pyrido [4,3,2-de]phthalazin-3(7H)-one,
9-phenyl-8-(pyridin-4-yl)-8,9-dihydro-2H-pyrido[4,3,2-de]phthalazin-3(7H)-one,
9-phenyl-8-(piperidin-4-yl)-8,9-dihydro-2H-pyrido[4,3,2-de]phthalazin-3(7H)-one,
9-phenyl-8-(pyridin-2-yl))-8,9-dihydro-2H-pryido[4,3,2-de]phthalazin-3(7H)-one,
8-(4((4-methylpiperazin-1-yl)methyl)phenyl)-9-phenyl-8,9-dihydro-2H-pyrido[4,3,2-de]phthalazin-3(7H)-one,
8,9-bis(4-flurophenyl)-8,9-dihydro-2H-pyrido[4,3,2-de]phthalazin-3(7H)-one,
8-(4-((dimethylamino)methyl)phenyl)-9-(4-fluorophenyl)-8,9-dihydro-2H-pyrido[4,3,2-de]phthalazin-3(7H)-one,
8(4-fluorophenyl)-9-(1-methyl-1H-imidazol-2-yl)-8,9-dihydro-2H-pyrido[4,3,2-de]phthalazin-3(7H)-one,
8,9-bis(3-((dimethylamino)methyl)phenyl)-8,9-dihydro-2H-pyrido[4,3,2-de]phthalazin-3(7H)-one,
9-(3-((cyclopropylamino)methyl)phenyl)-8-phenyl-8,9-dihydro-2H-pyrido[4,3,2-de]phthalazin-3(7H)-one,
8-(3-((dimethylamino)methyl)phenyl)-9-phenyl-8,9-dihydro-2H-pyrido[4,3,2-de]phthalazin-3(7H)-one,
8-(3-(morpholinomethyl)phenyl)-9-phenyl-8,9-dihydro-2H-pyrido[4,3,2-de]phthalazin3(7H)-one, 8-(4-(azetidin-1-ylmethyl)phenyl)-9-(4-fluorophenyl)-8,9-dihydro-2H-pyrido[4,3,2-de]phthalazin-3(7H)-one,
5-fluoro-8-(4-fluorophenyl)-9-(1-methyl-1H-1,2,4-triazol-5-yl)-8,9-dihydro-2H-pyrido[4,3,2-de]phthalazin-3(7H)-one,
9-(1-methyl-1H-1,2,4-triazol-5-yl)-8-phenyl-8,9-dihydro-2H-pyrido[4,3,2-de]phthalazin-3(7H)-one,
8-(4-((dimethylamino)methyl)phenyl)-9-(1-methyl-1H-1,2,4-triazol-5-yl)-8,9-dihydro-2H-pyrido[4,3,2-de]phthalazin-3(7H)-one,
8-(4-((dimethylamino)methyl)phenyl)-5-fluoro-9-(1-methyl-1H-1,2,4-triazol-5-yl)-8,9-dihydro-2H-pyrido[4,3,2-de]phthalazin-3(7H)-one,
8-(4-fluorophenyl)-9-methyl-9-(1-methyl-1H-1,2,4-triazol-5-yl)-8,9-dihydro-2H-pyrido[4,3,2-de]phthalazin-3(7H)-one,
8-(4-fluorophenyl)-9-(1,4,5-trimethyl 1-1H-imidazol-2-yl)-8,9-dihydro-2H-pyrido[4,3,2-de]phthalazin-3(7H)-one,
8-(4-fluorophenyl)-9-(1-methyl-1H-1,2,3-triazol-4-yl)-8,9-dihydro-2H-pyrido[4,3,2-de]phthalazin-3(7H)-one,
9-(4,5-dimethyl-4H-1,2,4-triazol-3-yl)-8-phenyl-8,9-dihydro-2H-pyrido[4,3,2-de]phthalazin-3(7H)-one,
9-(4,5-dimethyl-4H-1,2,4-triazol-3-yl)-8-(4-fluorophenyl)-8,9-dihydro-2H-pyrido[4,3,2-de]phthalazin-3(7H)-one,
8-(4-chlorophenyl)-9-(1-methyl-1H-imidazol-2-yl)-8,9-dihydro-2H-pyrido[4,3,2-de]phthalazin-3(7H)-one,
9-(1-methyl-1H-imidazol-2-yl)-8-(4-(trifluoromethyl)phenyl)-8,9-dihydro-2H-pyrido[4,3,2-de]phthalazin-3(7H)-one,
8-(4-fluorophenyl)-9-(thiazol-2-yl)-8,9-dihydro-2H-pyrido[4,3,2-de]phthalazin-3(7H)-one,
9-(1-ethyl-1H-imidazol-2-yl)-8-(4-fluorophenyl)-8,9-dihydro-2H-pyrido[4,3,2-de]phthalazin-3(7H)-one
8-(4-((4-ethyl-3-methylpiperazin-1-yl)methyl)phenyl)-9-phenyl-8,9-dihydro-2H-pyrido[4,3,2-de]phthalazin-3(7H)-one,
8-(4-((4-methylpiperazin-1-yl)methyl)phenyl)-9-(4-fluorophenyl)-8,9-dihydro-2H-pyrido[4,3,2-de]phthalazin-3(7H)-one,
9-(4-fluorophenyl)-8-(4-((4-methylpiperazin-1-yl)methyl)phenyl)-8,9-dihydro-2H-pyrido[4,3,2-de]phthalazin-3(7H)-one,
9-(4-fluorophenyl)-8-(4-(piperazin-1-ylmethyl)phenyl)-8,9-dihydro-2H-pyrido[4,3,2-de]phthalazin-3(7H)-one,
9-(4-fluorophenyl)-8-(4-((3-methylpiperazin-1-yl)methyl)phenyl)-8,9-dihydro-2H-pyrido[4,3,2-de]phthalazin-3(7H)-one,
9-(4-fluorophenyl)-8-(4-(pyrrolidin-1-ylmethyl)phenyl)-8,9-dihydro-2H-pyrido[4,3,2-de]phthalazin-3(7H)-one,
9-phenyl-8,9-dihydro-2H-pyrido[4,3,2-de]phthalazin-3(7H)-one,
8-(4-Fluorophenyl)-9-(4-methyl-4H-1,2,4-triazol-3-yl)-8,9-dihydro-2H-pyrido[4,3,2-de]phthalazin-3(7H)-one,
8-(4-fluorophenyl)-9-(1-methyl-1H-1,2,4-triazol-5-yl)-8,9-dihydro-2H-pyrido[4,3,2-de]phthalazin-3(7H)-one,
8-(4-fluorophenyl)-9-(1-methyl-1H-imidazo[4,5-c]pyridin-2-yl)-8,9-dihydro-2H-pyrido[4,3,2-de]phthalazin-3(7H)-one,
5-chloro-9-(1-methyl-1H-imidazol-2-yl)-8-phenyl-8,9-dihydro-2H-pyrido[4,3,2-de]phthalazin-3(7H)-one,
8-(4-((dimethylamino)methyl)phenyl)-5-fluoro-9-(4-fluorophenyl)-8,9-dihydro-2H-pyrido[4,3,2-de]phthalazin-3(7H)-one,
8,9-bis(4-((dimethylamino)methyl)phenyl)-5-fluoro-8,9-dihydro-2H-pyrido[4,3,2-de]phthalazin-3(7H)-one,
8-(4-((dimethylamino)methyl)phenyl)-5-fluoro-9-phenyl-8,9-dihydro-2H-pyrido[4,3,2-de]phthalazin-3(7H)-one,
8-(4-((3,4-dimethylpiperazin-1-methyl)phenyl)-9-(4-fluorophenyl)-8,9-dihydro-2H-pyrido[4,3,2-de]phthalazin-3(7H)-one,
8-(4-((3,5-dimethylpiperazin-1-yl)methyl)phenyl)-9-(4-fluorophenyl)-8,9-dihydro-2H-pyrido[4,3,2-de]phthalazin-3(7H)-one,
9-phenyl-8-(4-(pyrrolidin-1-ylmethyl)phenyl)-8,9-dihydro-2H-pyrido[4,3,2-de]phthalazin-3(7H)-one,
9-(1-methyl-1H-imidazol-2-yl)-8-(4-(pyrrolidin-1-ylmethyl)phenyl)-8,9-dihydro-2H-pyrido[4,3,2-de]phthalazin-3(7H)-one,
9-(4-fluorophenyl)-8-(1-methyl-1H-imidazol-2-yl)-8,9-dihydro-2H-pyrido[4,3,2-de]phthalazin-3(7H)-one,
9-(4-fluorophenyl)-8-(quinolin-6-yl)-8,9-dihydro-2H-pyrido[4,3,2-de]phthalazin-3(7H)-one;
8-(4-((dimethylamino)methyl)phenyl)-9-p-tolyl-8,9-dihydro-2H-pyrido[4,3,2-de]phthalazin-3(7H)-one,
9-(4-chlorophenyl)-8-(4-((dimethylamino)methyl)phenyl)-8,9-dihydro-2H-pyrido[4,3,2-de]phthalazin-3(7H)-one,
8-(4-((dimethylamino)methyl)phenyl)-9-(4-methoxyphenyl)-8,9-dihydro-2H-pyrido[4,3,2-de]phthalazin-3(7H)-one,
8-(4-((diethylamino)methyl)phenyl)-9-phenyl-8,9-dihydro-2H-pyrido[4,3,2-de]phthalazin-3(7H)-one,
8-(4-((diethylamino)methyl)phenyl)-9-(4-fluorophenyl)-8,9-dihydro-2H-pyrido[4,3,2-de]phthalazin-3(7H)-one,
9-(4-chlorophenyl)-8-(4-((diethylamino)methyl)phenyl)-8,9-dihydro-2H-pyrido[4,3,2-de]phthalazin-3(7H)-one,
5-fluoro-9-(4-fluorophenyl)-8-(1-methyl-1H-imidazol-2-yl)-8,9-dihydro-2H-pyrido[4,3,2-de]phthalazin-3(7H)-one,
8-(4-((dimethylamino)methyl)phenyl)-9-(4-ethylphenyl)-8,9-dihydro-2H-pyrido[4,3,2-de]phthalazin-3(7H)-one,
8-(4-((dimethylamino)methyl)phenyl)-9-(4-isopropylphenyl)-8,9-dihydro-2H-pyrido[4,3,2-de]phthalazin-3(7H)-one,
8-(4-((dimethylamino)methyl)phenyl)-9-(4-(trifluoromethyl)phenyl)-8,9-dihydro-2H-pyrido[4,3,2-de]phthalazin-3(7H)-one,
8-(4-((diethylamino)methyl)phenyl)-9-p-tolyl-8,9-dihydro-2H-pyrido[4,3,2-de]phthalazin-3(7H)-one,
9-(4-fluorophenyl)-8-(4-(1-methylpyrrolidin-2-yl)phenyl)-8,9-dihydro-2H-pyrido[4,3,2-de]phthalazin-3(7H)-one,
9-(4-fluorophenyl)-8-(4-(pyrrolidin-2-yl)phenyl)-8,9-dihydro-2H-pyrido[4,3,2-de]phthalazin-3(7H)-one,
8-(4-fluorophenyl)-9-methyl-9-(1-methyl-1H-imidazol-2-yl)-8,9-dihydro-2H-pyrido[4,3,2-de]phthalazin-3(7H)-one,
9-(4-fluorophenyl)-8-(1H-imidazol-2-yl)-8,9-dihydro-2H-pyrido[4,3,2-de]phthalazin-3(7H)-one,
5-fluoro-9-(1-methyl-1H-1,2,4-triazol-5-yl)-8-phenyl-8,9-dihydro-2H-pyrido[4,3,2-de]phthalazin-3(7H)-one,
9-(4-fluorophenyl)-9-hydroxy-8-(1-methyl-1H-imidazol-2-yl)-8,9-dihydro-2H-pyrido[4,3,2-de]phthalazin-one,
8-(4-(azetidin-1-ylmethyl)phenyl)-9-phenyl-8,9-dihydro-2H-pyrido[4,3,2-de]phthalazin-3(7H)-one, and 5-fluora-8-(1-methyl-1H-imidazol-2-yl)-9-phenyl-8,9-dihydro-2H-pyrido[4,3,2-de]phthalazin-3(7H)-one;

or a pharmaceutically acceptable salt, solvate or prodrug thereof.

14. A method of treating a disease associated with a PTEN deficiency ameliorated by the inhibition of PARP, wherein the disease associated with a PTEN deficiency is endometrial carcinoma, comprising administering to a subject in need of treatment a therapeutically effective amount of a pharmaceutical composition comprising a compound of Formula (I):

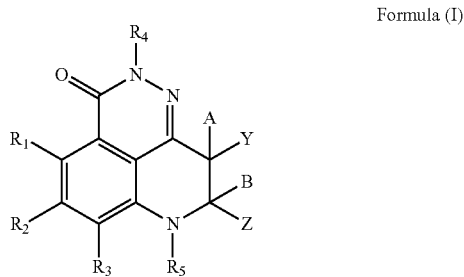

Formula (I)

wherein

Y and Z are each independently selected from the group consisting of:

a) an aryl group optionally substituted with 1, 2, or 3 $R_6$;

b) a heteroaryl group optionally substituted with 1, 2, or 3 $R_5$; and c) a substituent independently selected from the group hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocyloalkylalkyl, alkylcarbonyl, arylcarbonyl, heteroarylcarbonyl, alkylsulfonyl, arylsulfonyl, heteroarylsulfonyl, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene;

$R_1$, $R_2$, and $R_3$ are each independently selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl;

A and B are each independently selected from the group consisting of hydrogen, Br, Cl, F, I, OH, $C_1$-$C_6$alkyl, $C_3$-$C_8$cyclcoalkyl, alkoxy, and alkoxyalkyl, wherein $C_1$-$C_6$alkyl, $C_3$-$C_8$cycloalkyl, alkoxy, and alkoxyalkyl are independently optionally substituted with at least one substituent selected from the group consisting of OH, $NO_2$, CN, Br, Cl, F, I, $C_1$-$C_6$alkyl, and $C_3$-$C_8$cycloalkyl, wherein B is not OH;

$R_A$ and $R_B$ an independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$alkyl)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$—, wherein q is 1 or 2 and the 3-10 membered heterocycle ring is optionally substituted with 1, 2, 3, or 4 substituents independently selected from $C_2$-$C_{10}$-alkenyl, $C_1$-$C_{10}$-alkoxy, $C_1C_{10}$-alkoxy-$C_1$-$C_{10}$-alkyl, $C_1$-$C_{10}$-alkoxycarbonyl, $C_1$-$C_{10}$-alkyl, $C_1$-$C_{10}$alkylcarbonyl, $C_1$-$C_{10}$-alkylcarbonyloxy, $C_1$-$C_{10}$-alkylthio, $C_1$-$C_{10}$-alkylthio-$C_1$-$C_{10}$-alkyl, $C_2$-$C_{10}$-alkynyl, carboxy, cyano, formyl, $C_1C_{10}$-haloalkoxy, $C_1$-$C_{10}$-haloalkyl, halogen, hydroxyl, $C_1$-$C_{10}$-hydroxyalkylene, mercapto, nitro, —$NR_AR_B$, and $(NR_AR_B)$carbonyl;

$R_4$ and $R_5$ are each independently selected from the group consisting of hydrogen, alkyl, cycloalkyl, alkoxyalkyl, haloalkyl, hydroxyalkylene, and $(NR_AR_B)$alkylene; and each $R_6$ is selected from the group consisting of OH, $NO_2$, CN, Br, Cl, F, I, $C_1$-$C_6$alkyl, $C_3$-$C_8$cycloalkyl, $C_3$-$C_8$heterocycloalkyl, $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_3$-$C_8$heterocycloalkylthio, heterocyclooxy, heterocyclothio, $NR_AR_B$, $(NR_AR_B)C_1$-$C_6$alkylene, $(NR_A,R_B)$carbonyl, $(NR_AR_B)$carbonylalkylene, $(NR_AR_B)$sulfonyl, and $(NR_AR_B)$sulfonylalkylene; or a single isomer, stereoiosomer, or enantiomer, or mixture thereof;

or a pharmaceutically acceptable salt pharmaceutically acceptable solvate, or pharmaceutically acceptable prodrug, and a pharmaceutically acceptable carrier, excipient, binder or diluent thereof.

15. The method of claim 1, wherein said administration is in combination with ionizing radiation, one or more chemotherapeutic agents, or a combination thereof.

16. The method of claim 15, wherein the compound wherein with 1, 2, or 3 $R_6$;

alkoxy, and the group consisting of OH, wherein selected from $C_2$-$C_{10}$ or a single isomer, stereoisomer, or is administered simultaneously with ionizing radiation, one or more chemotherapeutic agents, or a combination thereof.

17. The method of claim 15, wherein the compound is administered sequentially with ionizing radiation, one or more chemotherapeutic agents, or a combination thereof.

18. A method of treating a cancer associated with a PTEN deficiency, wherein the cancer associated with a PTEN deficiency endometrial carcinoma, wherein said endometrial carcinoma is deficient in Homologous Recombination (HR) dependent DNA double strand break (DSD) repair pathway, comprising administering to a subject in need of treatment a therapeutically effective amount of a compound of Formula (I);

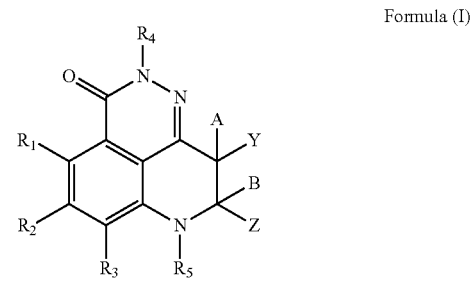

Formula (I)

wherein:
Y and Z are each independently selected from the group consisting of:
  a) an aryl group optionally substituted with 1, 2, or 3 $R_6$;
  b) a heteroaryl group optionally substituted with 1, 2, or 3 $R_6$; and
  c) a substituent independently selected from the group consisting of hydrogen, alkenyl, alkoxy, alkoxyalkyl, alkoxycarbonyl, alkoxycarboaylalkyl, alkyl, alkalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl alkylsulfonyl, arylsulfonyl, heteroarylsulfonyl, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene;

$R_1$, $R_2$, and $R_3$ are each independently selected from the group consisting of hydrogen, halogen, alkenyl, akkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl;

A and B are each independently selected from the group consisting of hydrogen, Br, Cl, F, I, OH, $C_1$-$C_6$alkyl, $C_3$-$C_8$cycloalkyl, alkoxy, and alkoxyalkyl, wherein $C_1$-$C_6$alkyl, $C_3$-$C_8$cycloalkyl, alkoxy, and alkoxyalkyl are independently optionally substituted with at least one substituent selected from the group consisting of OH, $NO_2$, CN, Br, Cl, F, I, $C_1$-$C_6$alkyl, and $C_3$-$C_8$cycloalkyl, wherein B is not OH;

$R_A$ and $R_B$ are independently selected from the group of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$-alkyl)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$-, wherein q is 1 or 2 and the 3-10 membered heterocycle ring is optionally substituted with 1, 2, 3, or 4 substituents independently selected from $C_2$-$C_{10}$-alkenyl, $C_1$-$C_{10\text{-}alkoxy}$, $C_1$-$C_{10}$-alkoxy-$C_{1\text{-}C10}$alkyl, $C_1$-$C_{10}$alkoxycarbonyl, $C_1$-$C_{10}$-alkyl, $C_1$-$C_{10}$-alkylcarbonyl, $C_1$-$C_{10}$-alkycarbonyloxy, $C_1$-$C_{10}$-alkylthio, $C_1$-$C_{10}$-alkyl, $C_2$-$C_{10}$-alkynyl, carboxy, cyano, formyl, $C_1$-$C_{10}$-haloalkoxy, $C_1$-$C_{10}$-haloalkyl, halogen, hydroxyl, $C_1$-$C_{10}$-hydroxyalkylene, mercapto, nitro, —$NR_AR_B$, and $(NR_AR_B)$carbonyl;

$R_4$ and $R_5$ are each independently selected from the group consisting of hydrogen, alkyl, cycloalkyl, alkoxyalkyl, haloalkyl, hydroxyalkylene, and $(NR_AR_B)$alkylene; and each $R_6$ is selected from the group consisting of OH, $NO_2$, CN, Br, Cl, F, I, $C_1$-$C_6$alkyl, $C_3$-$C_8$cycloalkyl, $C_3$-$C_8$heterocycloalkyl, $C_2$-$C_6$alkenyl, alkoxy, alkoxyalkyl, alkexycarbonyl, alkoxycarbonylalkyl, $C_2$-$C_6$alkynyl, aryl, arylalkyl, $C_3$-$C_8$cycloalkylalkyl, haloalkoxy, halolkyl, hydroxyalkylene, oxo, heteroaryl, heteroarylalkoxy, heteroaryloxy, heteroarylthio, heteroarylalkylthio, heterocycloalkoxy. $C_3$-$C_8$heterocycloalkylthio, heterocyclooxy, heterecyclothio, $NH_AR_B$, $(NR_AR_B)C_1$-$C_6$alkylene, $(NR_AR_B)$carbonyl, $(NR_AR_B)$carbonylalkylene, $(NR_ARB)$sulfonyl, and $(NR_AR_B)$sulfonylalkylene or a single isomer, stereoisomer, or enantiomer, or mixture thereof, optionally as a salt, solvate, chemically protected form or prodrug thereof.

19. The method of claim 18, wherein the endometrial carcinoma comprises one or more cancer cells having a reduced or abrogated ability to repair DNA DSB by HR relative to cancer cells.

20. The method of claim 19, wherein the endometrial carcinoma cancer cells have a PTEN deficient phenotype.

21. The method of claim 19, wherein the endometrial carcinoma cancer cells are deficient in PTEN.

22. The method of claim 18, wherein the endometrial carcinoma comprises one or more cancer cells deficient in protects involved in DNA DSB repair by HR.

23. The method of claim 22, wherein the endometrial carcinoma cancel cells are deficient in ATM, Rad51, Rad52, Rad54, Rad50, MRE11, NBS1, XRCC2, XRCC3, cABL, RPA, CtIP, or MBC.

24. The method of claim 23, wherein the endometrial carcinoma cancer cells are deficient in Rad51.

25. The method of claim 18 wherein a subject is heterozygous for a mutation in a gene encoding a component of the HR dependent DNA PSB repair pathway.

26. The method of claim 18 wherein the subject is heterozygous for a mutation in PTEN.

27. The method of claim 18 wherein the treatment further comprises administration of ionizing radiation or a chemotherapeutic agent.

28. A method of treating a disease associated with a PTEN deficiency, wherein the disease associated with a PTEN deficiency is endometrial carcinoma, wherein said endometrial carcinoma is associated with an abrogated or reduced ability to control the phosphoinositide 3-kinase signaling pathway comprising administering to a subject in need of treatment a therapeutically effective amount of a compound of Formula (I):

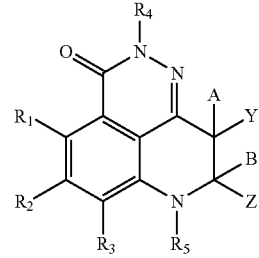

Formula (I)

wherein:
Y and Z arc each independently selected from the group consisting of:
  a) an aryl group optionally substituted with 1, 2, or 3 $R_6$;
  b) a heteroaryl group optionally substituted with 1, 2, or 3 $R_6$; and
  c) a substituent independently selected from the group consisting of hydrogen, alkenyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl, alkylsulfonyl, arylsulfonyl, heteroarylsulfonyl, $(NH_AR_B)$alkylene, $(NR_AR_B)$carbonyl, $(NR_AR_B)$carbonylalkylene, $(NR_AR_B)$sulfonyl, and $(NR_AR_B)$sulfonylalkylene;

$R_1$, $R_2$, and $R_3$ are each independently selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl;

A and B are each independently selected from the group consisting of hydrogen, Br, Cl, F, I, OH, $C_1$-$C_6$alkyl, $C_3$-$C_8$cycloalkyl, alkoxy, and alkoxyalkyl, wherein $C_1$-$C_6$alkyl, $C_3$-$C_8$cycloalkyl, alkoxy, and alkoxyalkyl are independently optionally substituted with at least one substituent selected from the group consisting of OH, $NO_2$, CN, Br, Cl, F, I, $C_1$-$C_6$alkyl, and $C_3$-$C_8$cycloalkyl, wherein B is not OH;

$R_A$ and $R_B$ are independently selected from the group consisting of hydrogen, alkyl, cycloalkyl, and alkylcabbonyl, or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1C_6$-alkyl)-, —N(aryl)- —N(aryl-$C_1$-$C_6$-alkly-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$-, wherein q is 1 or 2 and the 3-10 membered heterocycle ring is optionally substituted with 1, 2, 3, or 4 substituents independently selected from $C_2$-$C_{10}$-alkenyl, $C_1$-$C_{10}$-alkoxy, $C_1$-$C_{10}$alkoxy-$C_1$-$C_{10}$-alkyl, $C_1$-$C_{10}$-alkoxycarbonyl, $C_1$-$C_{10}$-alkyl, $C_1$-$C_{10}$-alkylcarbonyl, $C_1$-$C_{10}$-alkylcarbonyloxy, $C_1$-$C_{10}$-alkylthio, $C_1$-$C_{10}$-alkylthio-$C_1$-$C_{10}$-alkyl, $C_2$-$C_{10}$-alkynyl, carboxy, cyano, formyl, $C_1$-$C_{10}$-haloalkoxy, $C_1$-$C_{10}$-haloalkyl, halogen, hydroxyl, $C_1$-$C_{10}$- hydroxyalkylene, mercapto, nitro, —$NR_AR_B$ and $(NR_AR_B)$carbonyl;

$R_4$ and $R_5$ are each independently selected from the group consisting of hydrogen, alkyl, cycloalkyl, alkoxyalkyl, haloalkyl, hydroxyalkylene and $(NR_AR_B)$alkylene; and each $R_6$ is selected from the group consisting of CH, $NO_2$, CN, Br, Cl, F, I, $C_1$-$C_6$alkyl, $C_3$-$C_8$cycloalkyl, $C_3$-$C_8$heterocycloalkyl, $C_2$-$C_{,6}$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylalkylthio, heterocycloalkoxy, $C_3$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene; or a single isomer, stereoisomer, or enantiomer, or mixture thereof, optionally as a salt, solvate, chemically protected form or prodrug thereof.

29. A method of treating a disease associated with a PTEN deficiency, wherein the disease associated with a PTEN deficiency is endometrial carcinoma, wherein said endometrial carcinoma is due to abnormal regulation of centromere stability comprising administering to a subject in need of treatment a therapeutically effective amount of a compound of Formula. (I):

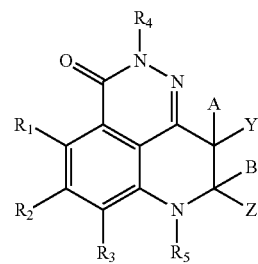

Formula (I)

wherein:
Y and Z are each independently selected from the group consisting of:
a) an aryl group optionally substituted with 1, 2, or 3 $R_6$;
b) a heteroaryl group optionally substituted with 1, 2, or 3 $R_6$; and
c) a substituent independently selected from the group consisting of hydrogen, alkenyl, alkoxy, alkoxyalkyl, alkoxycarbonyl, alkoxyearbonylalkyl, alkyl, alkynyl, arylalkyl, cycloalkyl, cycloalkylalkyl, haloalkyl, hydroxyalkylene, oxo, heterocycloalkyl, heterocycloalkylakyl, alkylcarbonyl, arylcarbonyl, heteroarylcarbonyl alkylsulfonyl, arylsulfonyl, heteroarylsulfonyl, $(NR_AR_B)$alkylene, $(NR_AR_B)$carbonyl, $(NR_AR_B)$carbonylalkylene, $(NR_AR_B)$sulfonyl, and $(NR_AR_B)$sulfonylalkylene;

$R_1$,$R_2$, and $R_3$ are each independently selected from the group consisting of hydrogen, halogen, alkenyl, alkomy, aloxycarbonyl, alkyl, cycloalkyl, alknyl, cyano, haloalkoxy, haloalkyl, hydroxyl, hydroxyalkylene, nitro, $NR_AR_B$, $NR_AR_B$alkylene, and $(NR_AR_B)$carbonyl;

A and B are each independently selected from the group consisting of hydrogen, Br, Cl, F, I, OH, $C_1$-$C_6$alkyl, $C_3$-$C_8$cycloalkyl, alkoxy, and alkoxyalkyl, wherein $C_1$-$C_6$alkyl, $C_3$-$C_8$cycloalkyl, alkoxy, and alkoxyalkyl are independently optionally substituted with at least one substituent selected from the group consisting of OH, $NO_2$, CN, Br, Cl, F, I, $C_1$-$C_6$alkyl, and $C_3$-$C_8$cycloalkyl, wherein B is not OH;

$R_A$ and $R_B$ are independently selected from the group consisting of hydrogen, alkyl, cycloalkyl, and alkylcarbonyl; or $R_A$ and $R_B$ taken together with the atom to which they are attached form a 3-10 membered heterocycle ring optionally having one to three heteroatoms or hetero functionalities selected from the group consisting of —O—, —NH, —N($C_1$-$C_6$-alkyl)-, —NCO($C_1$-$C_6$-alkyl)-, —N(aryl)-, —N(aryl-$C_1$-$C_6$-alkyl-)-, —N(substituted-aryl-$C_1$-$C_6$-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$-, wherein q is 1 or 2 and the 3-10 membered heterocycle ring is optionally substituted with 1, 2, 3, or 4 substituents independently selected from $C_2$-$C_{10}$alkenyl, $C_1$-$C_{10}$alkoxy, $C_1$-$C_{10}$-alkoxy-$C_1$-$C_{10\text{-}alkyl}$, $C_1$-$C_{10}$-alkoxycarbonyl, $C_1$-$C_{10}$-alkyl, $C_1$-$C_{10}$-alkylcarbonyl, $C_1$-$C_{10}$-alkylcarbonyloxy, $C_1$-$C_{10}$-alkylthio, $C_1$-$C_{10}$-alkylthio-$C_1$-$C_{10}$alkyl, $C_2$-$C_{10}$-alkynyl, carboxy, cyano, fomyl, $C_1$-$C_{10}$-haloalkoxy, $C_1$-$C_{10}$-haloalkyl, halogen, hydroxyl, $C_1$-$C_{10}$-hydroxyalkylene, mercapto, nitro, —$NR_AR_B$, and $(NR_AR_B)$carbonyl;

$R_4$ and $R_5$ are each independently selected from the group consisting of hydrogen, alkyl, cycloalkyl, alkoxyalkyl, haloalkyl, hydroxyalkylene, and $(NR_AR_B)$alkylene; and each R₆ is selected from the group consisting of OH, NO₂, CN, Br, Cl, F, I, $C_1$-$C_6$alkyl, $C_3$-$C_8$cycloalkyl, $C_3$-$C_8$heterocycloalkyl, $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylalkyl, haloalkoxy, haloalkyl, hydroxyalkylene, oxo, heteroaryl, heteroarylalkoxy, heteroaryloxy, heteroarylthio, heteroarylthio, heterocycloalkoxy, $C_3$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene; or a single isomer, stereoisomer, or enantiomer, or mixture thereof, optionally as a salt, solvate, chemically protected form or prodrug thereof.

30. The method of claim 1 where Y and Z are each independently selected from the group consisting of:
   a) a phenyl group optionally substituted with 1, 2, or 3 $R_6$; and
   b) an imidazole group optionally substituted with 1, 2, or 3 $R_6$;
   or a single isomer, stereoisomer, or enantiomer, or mixture thereof, optionally as a salt, or chemically protected form thereof.

31. The method of claim 1 where Y and Z are each independently selected tram the group consisting of:
   a) a phenyl group optionally substituted with 1, 2, or 3 $R_6$; and
   b) a triazole group optionally substituted with 1, 2, or 3 $R_6$;
   or a single isomer, stereoisomer, or enantiomer, or mixture thereof, optionally as a salt, or chemically protected form thereof.

32. A method of treating a disease associated with a PTEN deficiency ameliorated by the inhibition of PARP, wherein the disease associated with a PTEN deficiency is endometrial carcinoma, comprising administering to a subject in need of treatment a therapeutically effective amount of a compound selected from the group consisting of:
   (8S,9R)-5-fluoro-9-(1-methyl-1H-imidazol-2-yl)-8-phenyl-8,9-dihydro-2H-pyrido[1,3,2de]phthalazin-3(7H)-one,
   (8R,9S)-5-fluoro-9-(1-methyl-1H-imidazol-2-yl)-8-phenyl-8,9-dihydro-2H-pyrido[1,3,2de]phthalazin-3(7H)-one,
   (8S,9R)-5-fluoro-9-(1-methyl-1H-1,2,4-triazol-5-yl)-8-phenyl-8,9-dihydro-2H-pyrido[4,3,2-de]phthatazn-3(7H)-one,
   (8S,9S)-5-fluoro-9-(1-methyl-1H-1,2,4-triazol-5-yl)-8-phenyl-,9-dihydro-2H-pyrido[4,3,2-de]phthalazin-3(7H)-one,
   (8R,9S)-8-(4-fluorophenyl)-9-(1-methyl-1H-imidzol-2-yl)-8,9-dihydro-2H-pyrido[4,3,2-de]phthalazin-3(7H)-one,
   (8S,9R)-8-(4-fluorophenyl)-9-(1-methyl-1H-imidazol-2-yl)-8,9-dihydro-2H-pyrido-[4,3,2-de]phthalazin-3-(7H)-one,
   (8R,9S)-5-fluoro-8-(1-fluorophenyl)-9-(1-methyl-1H-1,2,4-triazol-5-yl)-8,9-dihydro-2H-pyrido [4,3,2-de]phthalazin-3(7H)-one,
   (8S,9R)-5-fluoro-8-(4-fluorophenyl)-9-(1-methyl-1H-1,2,4-triazol-5-yl)-8,9-dihydro-2H-pyrido [4,3,2-de]phthalazin-3(7H)-one,
   (8R,9S)-5-fluoro-8-(4-fluorophenyl)-9-(1-methyl-1H-imidazol-2-yl)-8,9-dihydro-2H -pyrido[4,3,2-de]phthalazin-3(7H)-one,
   (8S,9S)-5-fluoro-8-(4-fluorophenyl)-9-(1-methyl-1H-imidazol-2-yl)-8,9-dihydro-2H -pyrido[4,3,2-de]phthalazin-3(7H)-one,
   (8R,9S)-8-(4-fluorophenyl)-9-(1-methyl-1H-1,2,4-triazol-5-yl)-8,9-dihydro-2H-pyrido[4,3,2-de]phthalazin-3 (7H)-one,
   (8S,9R)-8-(4-fluorophenyl)-9-(1-methyl-1H-1,2,4-triazol-5-yl)-8,9-dihydro-2H-pyrido[4,3,2-de]phthalazin-3 (7H)-one,
   (8R,9S)-8-(4-((dimethylamino)methyl)phenyl)-5-fluoro-9-(1-triazol-5-yl)-8,9-dihydro-H-pyrido[4,3,2-de]phthalazin-3(7H)-one,
   (8S,9R)-8-(4-((dimethylamino)methyl)phenyl)-5-fluoro-9-(1-methyl-1H-1,2,4-triazol-5-yl)8,9-dihydro-2H-pyrido[4,3,2-de]phthalazin-3(7H)-one,
   (8R,9S)-8-(4-(azetidin-1-ylmethyl)phenyl)-9-(4-fluorophenyl)-8,9-dihydro-2H-pyrido[4,3,2-de]phthalazin-3(7H)-one, and
   (8S,9R)-8-(4-(azetidin-1-ylmethyl)phenyl)-9-4-fluorophenyl)-8,9-dihydro-2H-pyridoi[4,3,2-de]phthalazin-3(7H)-one, or a pharmaceutically acceptable salt, solvate or prodrug thereof.

33. A method of treating a disease associated with a PTEN deficiency ameliorated by the inhibition of PARP, wherein the disease associated with a PTEN deficiency is endometrial carcinoma, comprising administering to a subject in need of treatment a therapeutically effective amount of 5-fluoro-8-(4-fluorophenyl)-9-(1-methyl-1H-1,2,4-triazol-5-yl)8,9-dihydro-2H-pyrido[4,3,2-de]phthalazin-3(7H)-one or a single isomer, stereoisomer, or enantiomer, or mixture thereof, optionally as a pharmaceutically acceptable salt.

34. A method of treating astrocytoma; endometroid serous adenocarcinoma, endometroid clear cell adenocarcinoma, endometroid adenosquamous carcinoma, or mixed histology; and small cell comprising administering to a subject in need of treatment a therapeutically effective amount of a compound of Formula (I):

Formula (I)

wherein:
Y and Z are each independently selected from the group consisting of:
   a) an aryl group optionally substituted with 1, 2, or 3 $R_6$;
   b) a heteroaryl group optionally substituted with 1, 2, or 3 $R_6$; and
   c) a substituent independently selected from the group consisting of hydrogen, alkonyl, alkoxy, alkoxyalkyl, alkoxycarbonyl, alkoxycarbonylalkyl, alkyl, alkynyl, arylalkyl, cycloalkyl, cycloalkylalkyl, haloalkyl, hydroxyalkylene, oxo, heterocycloalkyl, heterocycloalkylalkyl, alkylcarbonyl, arylcarbonyl, heteroarylcarbonyl alkylsulfonyl, arylsulfonyl, heteroarylsulfonyl, $(NR_AR_B)$alkylene, $(NR_AR_B)$carbonyl, $(NR_AR_B)$carbonaylkylene, $(NR_AR_B)$sulfonyl, and $(NR_AR_B$sulfonylalkylene;

$R_1$, $R_2$, and $R_3$ are each independently selected from the group consisting of hydrogen, halogen, alkenyl, alkoxy, aloxycarbonyl, alkyl, cycloalkyl, alkynyl, cyano, haloalkoxy, haloalkyl, hydroxyl, hydroxyalkylene, nitro, $NR_AR_B$, $NR_AR_B$alkylene, and $(NR_AR_B)$carbonyl;

A and B are each independently selected from the group consisting of hydrogen, Br, Cl, F, I, OH, $C_1$-$C_6$alkyl, $C_3$-$C_8$cycloalkyl, alkoxy, and alkoxyalkyl, wherein $C_1$-$C_6$alkyl, $C_3$-$C_8$cycloalkyl, alkoxy, and alkoxyalkyl are independently optionally substituted with at least one substituent selected from the group consisting of OH, $NO_2$, CN, Br, Cl, F, I, $C_1$-$C_6$alkyl, and $C_3$-$C_8$cycloalkyl, wherein B is not OH;

$R_A$ and $R_B$ are indepepdently selected from the group consisting of hydrogen, alkyl, cycloalkyl, and alkylcarbonyl; or $R_A$ and $R_B$ taken together with the atom to which they are attached from a 3-10 membered heterocycle ring optionally haviug one to three heteroatoms or hetero functionalities seleted from the group consisting of —O—, —NH, —N($C_1$-$C_6$alkyl)-, —NCO($C_1$-$C_6$-alkyl)-, —N(arly)-, —N(aryl-$C_1$-$C_6$-alkyl-)-, —(substituted-aryl-$C_1C_6$alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(O)_q$-, wherein q is 1 or 2 and the 3-10 membered heterocycle ring is optionally substituted with 0, 1, 2, 3, or 4 substituents independently selected from $C_2$-$C_{10}$alkenyl, $C_1$-$C_{10}$-alkoxy, $C_1$-$C_{10}$-alkoxy-$C_1$-$C_{10}$-alkyl, $C_1$-$C_{10}$-alkoxycarbonyl, $C_1$-$C_{10}$-alkyl, $C_1$-$C_{10}$-alkylcarbonyl, $C_1$-$C_{10}$-alkylthio, $C_1$-$C_{10}$alkylthio-$C_1$-$C_{10}$alkyl, $C_2$-$C_{10}$-alkynyl, carboxy, cyano, formyl, $C_1$-$C_{10}$-haloalkoxy, $C_1$-$C_{10}$-haloalkyl, halogen, hydroxyl, $C_1$-$C_{10}$-hydroxyalkylene, mercapto, nitro, —$NR_AR_B$, and $(NR_AR_B)$carbonyl;

$R_4$ and $R_5$ are each independently selected from the group consisting of hydrogen, alkyl, cycloalkyl, alkoxyalkyl, haloalkyl, hydroxyalkylene, and $(NR_AR_B)$alkylene: and each $R_6$ is selected from the group consisting of OR, $NO_2$, CN, Br, Cl, F, I, $C_1$-$C_6$alkyl, $C_3$-$C_8$cycloalkyl, $C_3$-$C_8$hetercoyeloalkyl, $C_2$-$C_6$alkenyl, alkoxy, alkoxyalkyl, alkoxycarbonyl, alkoxycarbonylalkyl, $C_2$-$C_6$alkynyl, aryl, arylalkyl, $C_3$-$C_8$cycloalkylakyl, haloalkoxy, haloalkyl, hydroxyalkylene, oxo, hetetoaryl, heteroarylalkoxy, heteroaryloxy, heteroaryl thio, heteroarylalkylthio, heterocycloalkoxy, $C_3$-$C_8$heterocycloalkylthio, heterocyclooxy, heterocyclothio, $NR_AR_B$, $(NR_AR_B)C_1$-$C_6$alkylene, $(NR_AR_B)$carbonyl, $(NR_AR_B)$carbonylalkylene, $(NR_AR_B)$sulfonyl, and $(NR_AR_B)$sulfonylalkylene; or a single isomer, stereoisomer, or enantionier, or mixture thereof, optionally as a salt, solvate, chemically protected form or prodrug thereof.

35. The method of claim 34 where Y and Z are each independently selected from the group consisting of:

a) a phenyl group optionally substituted with 1, 2, or 3 $R_6$; and b) an imidazole group optionally substituted with 1, 2, or 3 $R_6$;

or a single isomer, stereoisomer, enantiomer, or mixture thereof, optionally as a salt, or chemically protected form thereof.

36. The method of claim 34 where Y and Z are each independently selected from the group consisting of:

a) a phenyl group optionally substituted with 1, 2, or 3 $R_6$; and b) a triazole group optionally substituted with 1, 2, or 3 $R_6$;

or a single isoimer, stereoisomer, or enantiomer, or mixture thereof, optionally as a salt, or chemically protected form thereof.

37. The method of claim 34 comprising administering to the subject a therapeutically effective amount of 5-fluoro-8-(4-fluorophenyl)-9-(1-methyl-1H-1,2,4-triazol-5-yl)-8,9-dihydro-2H-pyrido[4,3,2-de]phthalazin-3(7H)-one or a single isomer, stereoisomer, or enantiomer, or mixture thereof, optionally as a pharmaceutically acceptable salt.

38. A method of treating a disease associated with a PTEN deficiency wherein the disease associated with a PTEN deficiency is endometrial carcinoma, comprising administering to a subject in need of treatment a therapeutically effective amount of a compound of 5-fluoro-8-(4-fluorophettyl)-9-(1-methyl-1H-1,2,4-triazol-5yl)-8,9-dihydro-2H-pyrido[4,3,2-de]phthalazin-3(7H)-one or a single isomer, stereoisomer, or enantiomer, or mixture thereof, optionally as a pharmaceutically acceptable salt.

* * * * *